(12) United States Patent
Mbiya et al.

(10) Patent No.: US 11,712,404 B2
(45) Date of Patent: Aug. 1, 2023

(54) METHACRYLAMIDE ADHESIVE SYSTEMS

(71) Applicant: OREGON HEALTH & SCIENCE UNIVERSITY, Portland, OR (US)

(72) Inventors: Wilbes Mbiya, Portland, OR (US); Carmem Silvia Costa Pfeifer, Portland, OR (US); Jack Liborio Ferracane, Portland, OR (US)

( * ) Notice: Subject to any disclaimer, the term of this patent is extended or adjusted under 35 U.S.C. 154(b) by 187 days.

(21) Appl. No.: 16/978,750

(22) PCT Filed: Feb. 26, 2019

(86) PCT No.: PCT/US2019/019540
§ 371 (c)(1),
(2) Date: Sep. 7, 2020

(87) PCT Pub. No.: WO2019/173080
PCT Pub. Date: Sep. 12, 2019

(65) Prior Publication Data
US 2021/0047450 A1    Feb. 18, 2021

Related U.S. Application Data

(60) Provisional application No. 62/640,492, filed on Mar. 8, 2018.

(51) Int. Cl.
| A61K 6/30 | (2020.01) |
| A61K 6/887 | (2020.01) |
| A61K 6/60 | (2020.01) |
| C08F 222/10 | (2006.01) |

(52) U.S. Cl.
CPC ............. *A61K 6/30* (2020.01); *A61K 6/60* (2020.01); *A61K 6/887* (2020.01); *C08F 222/102* (2020.02)

(58) Field of Classification Search
CPC ........................................ A61K 6/30
See application file for complete search history.

(56) References Cited

U.S. PATENT DOCUMENTS

| 6,018,033 A | 1/2000 | Chen et al. |
| 6,750,268 B2 | 6/2004 | Hino |
| 9,682,019 B2 | 6/2017 | Klee et al. |
| 2011/0098375 A1 | 4/2011 | Gyakushi et al. |
| 2017/0020791 A1 | 1/2017 | Moszner et al. |

FOREIGN PATENT DOCUMENTS

| JP | 2011148747 A | * | 8/2011 | |
| WO | WO-2014202176 A1 | * | 12/2014 | ............. A61K 6/083 |
| WO | WO-2015190100 A1 | * | 12/2015 | ............... A61K 6/00 |

OTHER PUBLICATIONS

English machine translation (JP 2011-148747) (Year: 2011).*
Koyama, E.; Sanda, F.; Endo, T. Macromol. Chem. Phys. 1997, 198, 3669 (Year: 1997).*

\* cited by examiner

*Primary Examiner* — Michael F Pepitone

(57) ABSTRACT

Provided are compositions useful as dental adhesives comprising an acrylamide compound, a methacrylate base monomer, a polymerization initiator, and a polymerization inhibitor or a polymerization stabilizer.

18 Claims, 40 Drawing Sheets

METHACRYLAMIDE ADHESIVE SYSTEMS

CROSS REFERENCE TO RELATED APPLICATIONS

The present application is a U.S. national application pursuant to 35 U.S.C. 371 from PCT Application No. PCT/US19/019540 filed Feb. 26, 2019, which claims the benefit of U.S. Provisional Patent Application number 62/640,492 filed Mar. 8, 2018.

STATEMENT OF GOVERNMENT SUPPORT

This invention was made with government support under U01 DE023756 awarded by the National Institutes of Health. The government has certain rights in the invention.

The present invention concerns methacrylamide monomers useful in adhesive systems, particularly including dental adhesives with increased microtensile bond strength to dentin.

BACKGROUND OF THE INVENTION

Methacrylates are widely used in dentistry to create bonding between dental substrate and restorative material. The combination of hydrophilic monomers, such as 2-hydroxyethyl methacrylate (HEMA), with mainly hydrophobic dimethacrylate monomers allowed for the hybridization of the collagen on the dentin substrate [1, see bibliography below], as well as co-polymerization with the restorative composite material [2]. However, the incorporation of high concentrations of hydrophilic and/or ionic monomers increases water sorption of the system [3, 4], and the adhesive interfaces behave as permeable membranes [5]. In the presence of water, the ester linkage of the methacrylate backbone may undergo hydrolytic cleavage, yielding methacrylic acid and alcohol-bearing residues. In conjunction with the degradation of the collagen, this causes the bonding to progressively degrade over time due to the action of water and enzymes [6].

Acrylamides and methacrylamides, with more stable amide bonds, have been postulated as alternative monomers for the design of more hydrolytically stable adhesive systems [7, 8] with the rationale of increasing the longevity of the bonded interface. These monomers have been used in at least one commercial product for a number of years, with conflicting results, especially in clinical trials, with some studies showing similar clinical performance compared to methacrylate controls and others showing worse performance [9, 10]. Less than ideal results may be a function of the somewhat increased water sorption for some methacrylamides [11], as well as to their potential lower reactivity [12], which has been reported specifically for tertiary methacrylamides [13]. In fact, in depth, systematic analyses of the reaction kinetics of tertiary methacrylamides in co-polymerizations with monomers leading to the formation of glassy networks are lacking. In addition, past concerns over the cytotoxicity of acrylamides have precluded their use in biological applications, but more recently, non-cytotoxic alternatives have been reported [14]. These factors justify the current use of (meth)acrylamides in commercial preparations in combination with other monomers. Even for pure methacrylates, a mixture of monomers is typically employed to harness the advantages of each individual compound. For example, the basic composition of fifth generation adhesives contains a relatively viscous crosslinking base monomer, such as BisGMA, which is added to improve both the reactivity and the mechanical properties of the adhesive layer. A low-viscosity, hydrophilic co-monomer, such as HEMA is added to decrease the viscosity and improve spreading, but mainly to allow diffusion into the dentin substrate [7, 15]. This implies that all compounds need to be miscible with each other, as well as with the solvent of choice, as this affects both the interaction with the substrate and the reaction kinetics. In addition, the copolymerization of the monomers included in the mixture also needs to be considered. For example, it is well known that acrylates present much higher reactivity than their methacrylate counterparts, resulting in the formation of two independently polymerizing networks [16]. In summary, monomer reactivity and copolymerization ability are critical screening tools for monomer selection and adhesive design. Previous studies have tested the compatibility and co-polymerization of (meth)acrylamides with other commonly used monomers in dental adhesive applications [8, 17], with reported improvements in bond strength [8, 18, 19]. Others have demonstrated lower reactivity of certain methacrylamides [15].

Since the presence of water in the hybrid layer is inevitable, several strategies have been proposed to improve the resistance of the adhesive layer to degradation. One attempt has been the elimination or reduction of the ester groups on the polymeric network, such as with the use of (meth)acrylamide-based adhesives systems. The presence of a nitrogen atom in amides, as compared to the oxygen atom in acrylates, leads to steric and electronic effects that reduce the susceptibility to hydrolysis. Nitrogen is less electronegative than oxygen, which makes it more likely to donate non-bonded electrons to the carbonyl carbon, shortening and strengthening the bond, ultimately decreasing the susceptibility to nucleophilic attack [20]. Tertiary methacrylamides present significant lower reactivity, while tertiary acrylamides and secondary methacrylamides present similar or higher reactivity compared to methacrylates [21].

Commercially available self-etching dental adhesives are methacrylates having either have a phosphate or carboxyl acidic group, a portion of which becomes dissociated in a self-etching primer solution, creating an acidic composition that degrades before application/in storage. The acidic hydrolysis of the methacrylate adhesive monomers in aqueous environment remains a problem to be addressed.

SUMMARY OF THE INVENTION

Provided here are hydrolytically stable dental adhesive secondary methacrylamides, with polar terminals (—OH) and self-etching terminals (phosphoric acid and carboxylic acid). They are useful, for example, in adhesive compositions comprising:
  i) an alpha-substituted secondary acrylamide compound comprising at least an organic non-acidic (OH) group or an acidic group selected from:
    a) an organic acidic functional group (—COOH); and
    b) an inorganic acidic functional group (—PO$_3$H$_2$);
  ii) a polymerizable bifunctionalized methacrylate base monomer;
  iii) a polymerization initiator;
  iv) a polymerization inhibitor or a polymerization stabilizer.

Examples of polymerizable bifunctionalized methacrylate base monomers for use in the compositions above are Bisphenol A glycerolate dimethacrylate (BisGMA), urethane dimethacrylate (UDMA), and (ethane-1,2-diylbis(oxy))bis(ethane-2,1-diyl) bis(2-methylacrylate) (TEGDMA).

In one embodiment is provided a dental adhesive composition comprising:
a) from about 50 wt % to about 70 wt % of a polymerizable bifunctionalized methacrylate base monomer;
b) from about 30 wt % to about 50 wt % of an alpha-substituted secondary methacrylamide compound comprising at least an organic non-acidic (OH) group or an acidic group selected from:
  i. an organic acidic functional group (—COOH); and
  ii. an inorganic acidic functional group (—PO$_3$H$_2$);
c) a polymerization initiator; and
d) a polymerization inhibitor or a polymerization stabilizer.

Another embodiment provides a dental adhesive composition comprising:
a) from about 55 wt % to about 65 wt % of a polymerizable bifunctionalized methacrylate base monomer;
b) from about 35 wt % to about 45 wt % of an alpha-substituted secondary methacrylamide compound comprising at least an organic non-acidic (OH) group or an acidic group selected from:
  i. an organic acidic functional group (—COOH); and
  ii. an inorganic acidic functional group (—PO$_3$H$_2$);
c) a polymerization initiator; and
d) a polymerization inhibitor or a polymerization stabilizer.

Optionally, the adhesive compositions herein further comprise a dental filler material. Also optionally, the adhesive compositions may comprise a solvent, such as selected from water, ethanol, acetone, or combinations thereof.

DETAILED DESCRIPTION OF THE INVENTION

Methacrylamide Monomers

Figure 1A:
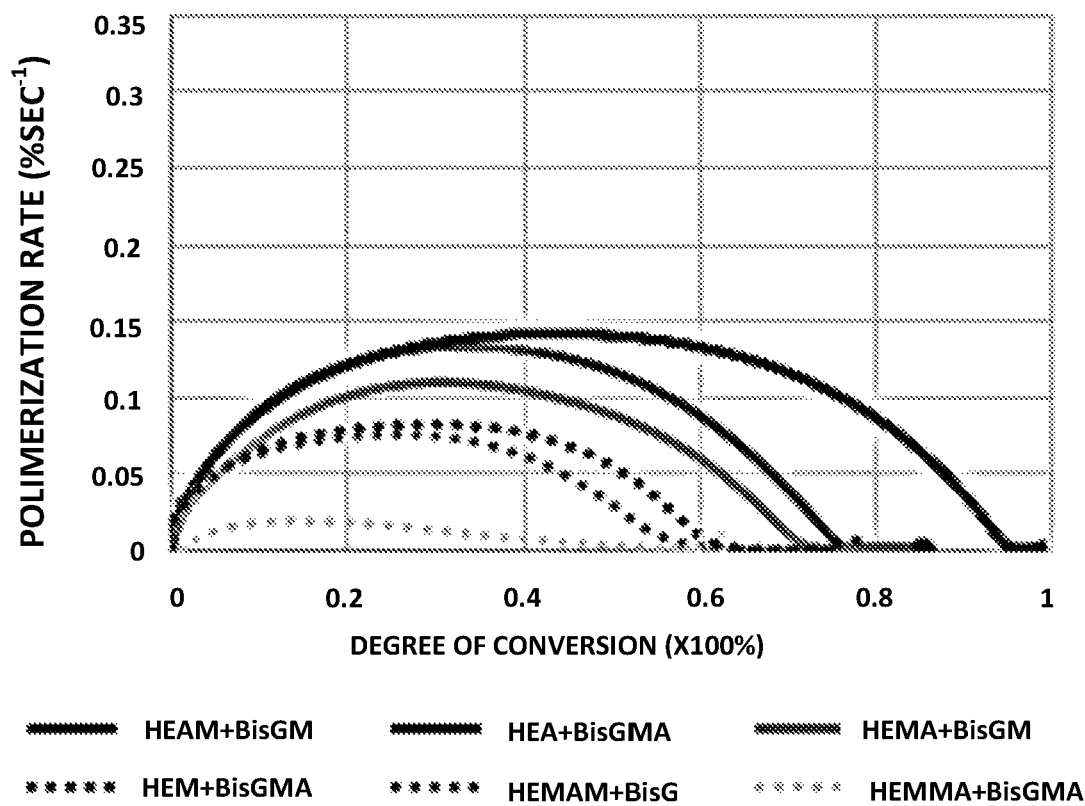
FIGS. 1A, 1B, and 1C depict the degree of conversion for BisGMA-containing resin combinations tested.

Provided are dental adhesives comprising methacrylamide compounds of Formula (I):

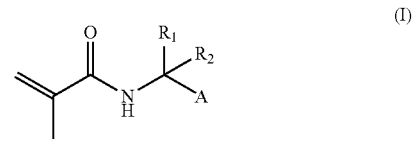

wherein:

A is selected from —R$_3$—OH; —CO$_2$R$_4$, —R$_3$—CO$_2$R$_4$, and a group of the formula:

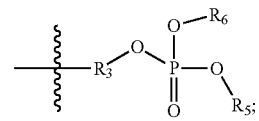

R$_1$ is selected from:
a) C$_1$-C$_6$ alkyl;
b) C$_3$-C$_6$ cycloalkyl;
c) —CH$_2$—C$_3$-C$_6$ cycloalkyl;
d) C$_3$-C$_6$ cycloalkenyl substituted by 0, 1, 2, 3, or 4 C$_1$-C$_4$ alkyl substituents;
e) —CH$_2$—C$_3$-C$_6$ cycloalkenyl substituted by 0, 1, 2, 3, or 4 C$_1$-C$_4$ alkyl substituents;
f) phenyl substituted by 0, 1, 2, 3, or 4 C$_1$-C$_4$ alkyl substituents; and
g) benzyl substituted by 0, 1, 2, 3, or 4 C$_1$-C$_4$ alkyl substituents;

$R_2$ is selected from H and $C_1$-$C_6$ alkyl; and
$R_3$ is selected from the group of:
a) $C_1$-$C_{16}$ linear or branched alkylene;
b) $C_2$-$C_{16}$ linear or branched alkenylene;

c)

d)

e)

f)

$A^1$ and $A^2$ in each instance is independently a $C_1$-$C_{12}$ alkylene chain optionally substituted by 1, 2, 3, or 4 $C_1$-$C_4$ alkyl substituents;

$B^1$ and $B^2$ in each instance is independently a $C_2$-$C_{12}$ alkenylene optionally substituted by 1, 2, 3, or 4 $C_1$-$C_4$ alkyl substituents;

each wavy line (\{)

represents a bond through which the indicated $A^1$ or $A^2$ alkylene chain or $B^1$ or $B^2$ alkenylene chain is attached;

with the proviso that the combined number of carbon atoms in the alkylene and/or alkenylene chains of the pairings $A^1$-$A^2$, $B^1$-$B^2$, $A^1$-$B^1$, and $B^1$-$A^1$ does not exceed 16;

$R_4$, $R_5$ and $R_6$ are each independently selected from H, $C_1$-$C_6$ alkyl, $C_3$-$C_6$ cycloalkyl, $C_3$-$C_6$ cycloalkenyl, —($CH_2$)q-cycloalkyl, —($CH_2$)q-cycloalkenyl, phenyl, benzyl, and naphthyl;

q is an integer selected from 1, 2, 3, and 4.

Also provided are dental adhesives comprising methacrylamide compounds of Formula (I):

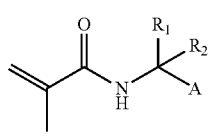

(I)

wherein:
A is selected from —$R_3$—OH; —$CO_2R_4$, —$R_3$—$CO_2R_4$ and a group of the formula:

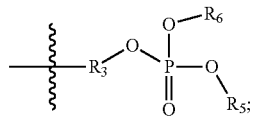

$R_1$ is selected from:
a) $C_1$-$C_6$ alkyl;
b) $C_3$-$C_6$ cycloalkyl;
c) —$CH_2$—$C_3$-$C_6$ cycloalkyl;
d) $C_3$-$C_6$ cycloalkenyl substituted by 0, 1, 2, 3, or 4 $C_1$-$C_4$ alkyl substituents;
e) —$CH_2$—$C_3$-$C_6$ cycloalkenyl substituted by 0, 1, 2, 3, or 4 $C_1$-$C_4$ alkyl substituents;
f) phenyl substituted by 0, 1, 2, 3, or 4 $C_1$-$C_4$ alkyl substituents; and
g) benzyl substituted by 0, 1, 2, 3, or 4 $C_1$-$C_4$ alkyl substituents;

$R_2$ is selected from H and $C_1$-$C_6$ alkyl; and
$R_3$ is selected from the group of:
h) $C_1$-$C_{10}$ linear or branched alkylene;
i) $C_2$-$C_{10}$ linear or branched alkenylene;

j)
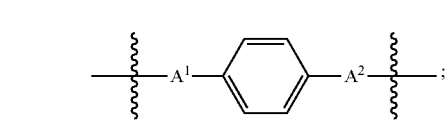

k)
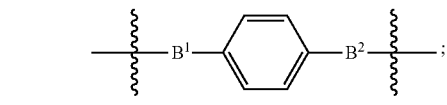

l)
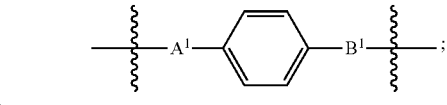

m)
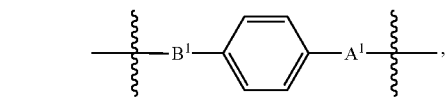

$A^1$ and $A^2$ in each instance is independently a $C_1$-$C_8$ alkylene chain optionally substituted by 1, 2, 3, or 4 $C_1$-$C_4$ alkyl substituents;

$B^1$ and $B^2$ in each instance is independently a $C_2$-$C_8$ alkenylene optionally substituted by 1, 2, 3, or 4 $C_1$-$C_4$ alkyl substituents;

each wavy line ( ∿∿ ) represents a bond through which the indicated $A^1$ or $A^2$ alkylene chain or $B^1$ or $B^2$ alkenylene chain is attached;

with the proviso that the combined number of carbon atoms in the alkylene and/or alkenylene chains of the pairings $A^1$-$A^2$, $B^1$-$B^2$, $A^1$-$B^1$, and $B^1$-$A^1$ does not exceed 10;

$R_4$, $R_5$ and $R_6$ are each independently selected from H, $C_1$-$C_6$ alkyl, $C_3$-$C_6$ cycloalkyl, $C_3$-$C_6$ cycloalkenyl, —(CH$_2$)q-cycloalkyl, —(CH$_2$)q-cycloalkenyl, phenyl, benzyl, and naphthyl;

q is an integer selected from 1, 2, 3, and 4.

Another embodiment provides dental adhesives comprising methacrylamide compounds of Formula (I) in which $R_1$, $R_2$, A, $R_4$, $R_5$, and $R_6$ are as defined immediately above and $R_3$ is selected from the group of:

a) $C_{10}$-$C_{16}$ linear or branched alkylene;

b) $C_{10}$-$C_{16}$ linear or branched alkenylene;

c) 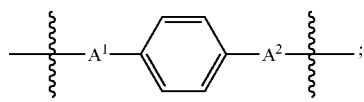

d) 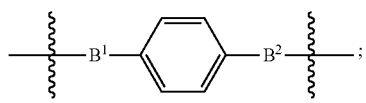

d) 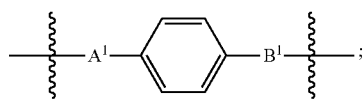

f) 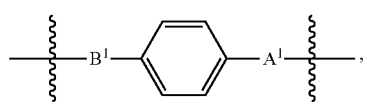

$A^1$ and $A^2$ in each instance is independently a $C_1$-$C_{12}$ alkylene chain optionally substituted by 1, 2, 3, or 4 $C_1$-$C_4$ alkyl substituents;

$B^1$ and $B^2$ in each instance is independently a $C_2$-$C_{12}$ alkenylene optionally substituted by 1, 2, 3, or 4 $C_1$-$C_4$ alkyl substituents;

each wavy line $$\{\!\{\!\{$$

represents a bond through which the indicated $A^1$ or $A^2$ alkylene chain or $B^1$ or $B^2$ alkenylene chain is attached;

with the proviso that the combined number of carbon atoms in the alkylene and/or alkenylene chains of the pairings $A^1$-$A^2$, $B^1$-$B^2$, $A^1$-$B^1$, and $B^1$-$A^1$ is an integer of from 10-16.

As an example of determining the number of carbon atoms in the alkylene and/or alkenylene chains of the pairings $A^1$-$A^2$, $B^1$-$B^2$, $A^{1'}$-$B^1$, and $B^1$-$A^1$, consider the structure below. While it has an isopropyl and two methyl substituents, the linear propylene and butenyl chains to which they are bound comprise a chain having seven combined carbon atoms.

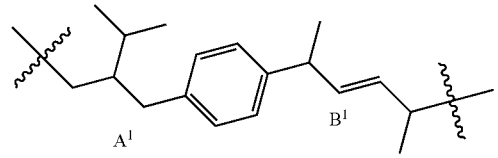

Another embodiment provides compounds of Formula (I) wherein $R_1$, $R_2$, A, $R_4$, $R_5$, and $R_6$ are as defined above and $R_3$ is —(CH$_2$)$_m$-phenyl-(CH$_2$)$_n$—;

m is an integer selected from 1, 2, 3, 4, 5, 6, 7, 8, 9, 10, 11, and 12; and n is an integer selected from 1, 2, 3, 4, 5, 6, 7, 8, 9, 10, 11, and 12;

with the proviso that the sum of m+n is not greater than 16.

A further embodiment provides compounds of Formula (I) wherein $R_1$, $R_2$, A, $R_4$, $R_5$, and $R_6$ are as defined above and $R_3$ is —(CH$_2$)$_m$-phenyl-(CH$_2$)$_n$—;

m is an integer selected from 1, 2, 3, 4, 5, 6, 7, and 8; and n is an integer selected from 1, 2, 3, 4, 5, 6, 7, and 8;

with the proviso that the sum of m+n is not greater than 10.

Another embodiment provides compounds of Formula (I) wherein $R_1$, $R_2$, A, $R_4$, $R_5$, and $R_6$ are as defined above and $R_3$ is —(CH$_2$)$_m$-phenyl-(CH$_2$)$_n$—;

m is an integer selected from 1, 2, 3, 4, 5, 6, 7, 8, 9, 10, 11, and 12; and n is an integer selected from 1, 2, 3, 4, 5, 6, 7, 8, 9, 10, 11, and 12;

with the proviso that the sum of m+n is an integer from 10-16.

Provided as well are dental adhesives comprising methacrylamide monomers of Formula (I):

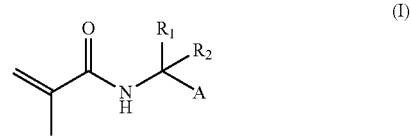

wherein:

A is selected from —$R_3$—OH; —$CO_2R_4$, —$R_3$—$CO_2R_4$ and a group of the formula:

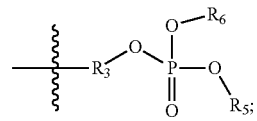

$R_1$ is selected from $C_1$-$C_6$ alkyl; $C_3$-$C_6$ cycloalkyl substituted by 0, 1, 2, 3, or 4 $C_1$-$C_4$ alkyl substituents; —CH$_2$—$C_3$-$C_6$ cycloalkyl substituted by 0, 1, 2, 3, or 4 $C_1$-$C_4$ alkyl substituents; phenyl substituted by 0, 1, 2, 3, or 4 $C_1$-$C_4$ alkyl substituents; and benzyl substituted by 0, 1, 2, 3, or 4 $C_1$-$C_4$ alkyl substituents;

$R_2$ is selected from H and $C_1$-$C_4$ alkyl;

$R_3$ is selected from $C_1$-$C_{16}$ linear or branched alkylene and $C_3$-$C_{16}$ linear or branched alkenylene;

$R_4$, $R_5$ and $R_6$ are each independently selected from H, $C_1$-$C_6$ alkyl, $C_3$-$C_6$ cycloalkyl, $C_3$-$C_6$ cycloalkenyl, —(CH$_2$)q-cycloalkyl, —(CH$_2$)q-cycloalkenyl, phenyl, benzyl, and naphthyl; and q is an integer selected from 1, 2, 3, and 4.

Another embodiment provides dental adhesives comprising methacrylamide monomers of Formula (I) wherein $R_1$, $R_2$, A, $R_4$, $R_5$, and $R_6$ are as defined immediately above and $R_3$ is selected from $C_1$-$C_{10}$ linear or branched alkylene and $C_3$-$C_{10}$ linear or branched alkenylene.

Another embodiment provides dental adhesives comprising methacrylamide monomers of Formula (I) wherein $R_1$, $R_2$, A, $R_4$, $R_5$, and $R_6$ are as defined immediately above and $R_3$ is selected from $C_{10}$-$C_{16}$ linear or branched alkylene and $C_{10}$-$C_{16}$ linear or branched alkenylene.

Also provided are dental adhesives comprising methacrylamide monomers of Formula (I) wherein:

A is selected from —$R_3$—OH; —$CO_2R_4$, —$R_3$—$CO_2R_4$ and a group of the formula:

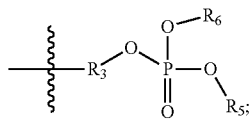

$R_1$ is selected from $C_1$-$C_6$ alkyl; phenyl substituted by 0, 1, 2, 3, or 4 $C_1$-$C_4$ alkyl substituents; and benzyl substituted by 0, 1, 2, 3, or 4 $C_1$-$C_4$ alkyl substituents;

$R_2$ is selected from H and $CH_3$; and $R_3$ is $C_1$-$C_{16}$ linear or branched alkylene $R_4$, $R_5$ and $R_6$ are each independently selected from H, $C_1$-$C_6$ alkyl, $C_3$-$C_6$ cycloalkyl, $C_3$-$C_6$ cycloalkenyl, —($CH_2$)q-cycloalkyl, —($CH_2$)q-cycloalkenyl, phenyl, benzyl, and naphthyl;

q is an integer selected from 1, 2, 3, and 4.

Another embodiment provides dental adhesives comprising methacrylamide monomers of Formula (I) wherein $R_1$, $R_2$, $R_4$, $R_5$, $R_6$, and A are as defined immediately above and $R_3$ is $C_1$-$C_{10}$ linear or branched alkylene.

Another embodiment provides dental adhesives comprising methacrylamide monomers of Formula (I) wherein $R_1$, $R_2$, $R_4$, $R_5$, $R_6$, and A are as defined immediately above and $R_3$ is $C_{10}$-$C_{16}$ linear or branched alkylene.

Also provided for use in compositions herein are methacrylamide monomers of Formula (I) wherein:
A, $R_4$, $R_5$, and $R_6$ are as defined above;
$R_1$ is selected from $C_1$-$C_6$ alkyl and phenyl;
$R_2$ is selected from H and $CH_3$; and
$R_3$ is $C_1$-$C_{16}$ alkylene.

Also provided for use in compositions herein are methacrylamide monomers of Formula (I) wherein:
A, $R_4$, $R_5$, and $R_6$ are as defined above;
$R_1$ is selected from $C_1$-$C_6$ alkyl and phenyl;
$R_2$ is selected from H and $CH_3$; and
$R_3$ is $C_1$-$C_{10}$ alkylene.

Also provided for use in compositions herein are methacrylamide monomers of Formula (I) wherein:
A, $R_4$, $R_5$, and $R_6$ are as defined above;
$R_1$ is selected from $C_1$-$C_6$ alkyl and phenyl;
$R_2$ is selected from H and $CH_3$; and
$R_3$ is $C_{10}$-$C_{16}$ alkylene.

Other compounds comprise those of Formula (I) wherein:
A, $R_4$, $R_5$, and $R_6$ are as defined above;
$R_1$ is $C_1$-$C_6$ alkyl;
$R_2$ is selected from H and $CH_3$; and
$R_3$ is $C_1$-$C_{16}$ alkylene.

Other compounds comprise those of Formula (I) wherein:
A, $R_4$, $R_5$, and $R_6$ are as defined above;
$R_1$ is $C_1$-$C_6$ alkyl;
$R_2$ is selected from H and $CH_3$; and
$R_3$ is $C_1$-$C_{10}$ alkylene.

Other compounds comprise those of Formula (I) wherein:
A, $R_4$, $R_5$, and $R_6$ are as defined above;
$R_1$ is $C_1$-$C_6$ alkyl;
$R_2$ is selected from H and $CH_3$; and
$R_3$ is $C_{10}$-$C_{16}$ alkylene.

Additional compounds comprise those of Formula (I) wherein:
A, $R_4$, $R_5$, and $R_6$ are as defined above;
$R_1$ is $C_1$-$C_6$ alkyl;
$R_2$ is H; and
$R_3$ is $C_1$-$C_{16}$ alkylene.

Additional compounds comprise those of Formula (I) wherein:
A, $R_4$, $R_5$, and $R_6$ are as defined above;
$R_1$ is $C_1$-$C_6$ alkyl;
$R_2$ is H; and
$R_3$ is $C_1$-$C_{10}$ alkylene.

Additional compounds comprise those of Formula (I) wherein:
A, $R_4$, $R_5$, and $R_6$ are as defined above;
$R_1$ is $C_1$-$C_6$ alkyl;
$R_2$ is H; and
$R_3$ is $C_{10}$-$C_{16}$ alkylene.

Also provided are compounds of Formula (I) wherein:
A, $R_4$, $R_5$, and $R_6$ are as defined above;
$R_1$ is $C_1$-$C_4$ alkyl;
$R_2$ is H; and
$R_3$ is $C_{10}$-$C_{16}$ alkylene.

Also provided are compounds of Formula (I) wherein:
A, $R_4$, $R_5$, and $R_6$ are as defined above;
$R_1$ is $C_1$-$C_4$ alkyl;
$R_2$ is H; and
$R_3$ is $C_1$-$C_{10}$ alkylene.

Also provided are compounds of Formula (I) wherein:
A, $R_4$, $R_5$, and $R_6$ are as defined above;
$R_1$ is $C_1$-$C_4$ alkyl;
$R_2$ is H; and
$R_3$ is $C_{10}$-$C_{16}$ alkylene.

Further compounds comprise those of Formula (I) wherein:
A, $R_4$, $R_5$, and $R_6$ are as defined above;
$R_1$ is phenyl;
$R_2$ is H; and
$R_3$ is $C_1$-$C_{16}$ alkylene.

Further compounds comprise those of Formula (I) wherein:
A, $R_4$, $R_5$, and $R_6$ are as defined above;
$R_1$ is phenyl;
$R_2$ is H; and
$R_3$ is $C_1$-$C_{10}$ alkylene.

Further compounds comprise those of Formula (I) wherein:
A, $R_4$, $R_5$, and $R_6$ are as defined above;
$R_1$ is phenyl;
$R_2$ is H; and
$R_3$ is $C_{10}$-$C_{16}$ alkylene.

Further compounds comprise those of Formula (I) wherein:
A, $R_4$, $R_5$, and $R_6$ are as defined above;
$R_1$ is $C_3$-$C_6$ cycloalkenyl substituted by 0, 1, 2, 3, or 4 $C_1$-$C_4$ alkyl substituents;
$R_2$ is H; and
$R_3$ is $C_1$-$C_{16}$ alkylene.

Further compounds comprise those of Formula (I) wherein:

A, R₄, R₅, and R₆ are as defined above;
R₁ is $C_3$-$C_6$cycloalkenyl substituted by 0, 1, 2, 3, or 4 $C_1$-$C_4$ alkyl substituents;
R₂ is H; and
R₃ is $C_1$-$C_{10}$ alkylene.

Further compounds comprise those of Formula (I) wherein:
A, R₄, R₅, and R₆ are as defined above;
R₁ is $C_3$-$C_6$cycloalkenyl substituted by 0, 1, 2, 3, or 4 $C_1$-$C_4$ alkyl substituents;
R₂ is H; and
R₃ is $C_{10}$-$C_{16}$ alkylene.

Further compounds comprise those of Formula (I) wherein:
A, R₄, R₅, and R₆ are as defined above;
R₁ is —$CH_2$—$C_3$-$C_6$cycloalkenyl substituted by 0, 1, 2, 3, or 4 $C_1$-$C_4$ alkyl substituents;
R₂ is H; and
R₃ is $C_1$-$C_6$ alkylene.

Further compounds comprise those of Formula (I) wherein:
A, R₄, R₅, and R₆ are as defined above;
R₁ is —$CH_2$—$C_3$-$C_6$cycloalkenyl substituted by 0, 1, 2, 3, or 4 $C_1$-$C_4$ alkyl substituents;
R₂ is H; and
R₃ is $C_1$-$C_{10}$ alkylene.

Further compounds comprise those of Formula (I) wherein:
A, R₄, R₅, and R₆ are as defined above;
R₁ is —$CH_2$—$C_3$-$C_6$cycloalkenyl substituted by 0, 1, 2, 3, or 4 $C_1$-$C_4$ alkyl substituents;
R₂ is H; and
R₃ is $C_{10}$-$C_{16}$ alkylene.

Also provided are six additional distinct sets of compounds of Formulas (II) through (VII), below, in each of which A is as defined above for Formula (I):

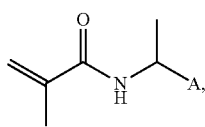  (II)

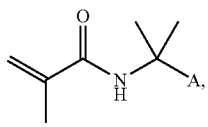  (III)

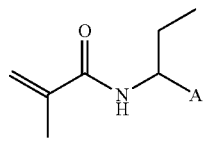  (IV)

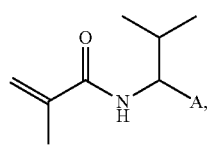  (V)

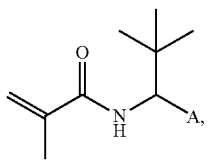  (VI)

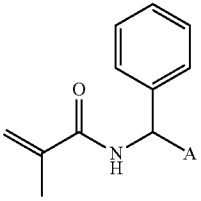  (VII)

Also provided are six additional distinct sets of compounds of Formulas (II) through (VII), above, in each of which A is as defined above and R₃ comprises a $C_1$-$C_{16}$ alkylene group.

Also provided are six additional distinct sets of compounds of Formulas (II) through (VII), above, in each of which A is as defined above and R₃ comprises a $C_1$-$C_{10}$ alkylene group.

Also provided are six additional distinct sets of compounds of Formulas (II) through (VII), above, in each of which A is as defined above and R₃ comprises a $C_{10}$-$C_{16}$ alkylene group.

Within each of the descriptions of compounds above comprising a compound of any of Formulas (I), (II), (III), (IV), (V), (VI), and (VII), there is a further embodiment of compounds wherein A is as defined above and R₃ is $C_1$-$C_8$ alkylene and each other variable is as described.

Within each of the descriptions of compounds above comprising a compound of any of Formulas (I), (II), (III), (IV), (V), (VI), and (VII), there is a further embodiment of compounds wherein A is as defined above and R₃ is $C_1$-$C_6$ alkylene and each other variable is as described.

Within each of the descriptions of compounds above comprising a compound of any of Formulas (I), (II), (III), (IV), (V), (VI), and (VII), there is a further embodiment of compounds wherein A is as defined above and R₃ is $C_1$-$C_4$ alkylene and each other variable is as described.

Within each of the descriptions of compounds above comprising a compound of any of Formulas (I), (II), (III), (IV), (V), (VI), and (VII), there is a further embodiment of compounds wherein A is as defined above and R₃ is $C_1$-$C_3$ alkylene and each other variable is as described.

Within each of the descriptions of compounds above comprising a compound of any of Formulas (I), (II), (III), (IV), (V), (VI), and (VII), there is a further embodiment of compounds wherein A is as defined above and R₃ is methylene (—$CH_2$—) and each other variable is as described.

Within each embodiment or group of acrylamide compounds described herein using Formula (I), there is a further embodiment in which A is —R₃—OH.

Within each embodiment or group of acrylamide compounds described herein using Formula (I), there is a further embodiment in which A is —$CO_2R_4$ and R₄ is as defined above.

Within each embodiment or group of acrylamide compounds described herein using Formula (I), there is a further embodiment in which A is —R₃—$CO_2R_4$ wherein R₃ is as defined for the embodiment and R₄ is as defined above.

Within each embodiment or group of acrylamide compounds described herein using Formula (I), there is a further embodiment in which A is the moiety:

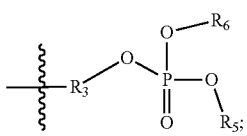

R₃ is as defined for the embodiment and R₅ and R₆ are as defined above.

Also provided herein is the use of a compound as described herein in the preparation of an adhesive. Separate embodiments are understood for the use of each compound or group of compounds described herein, including those of Formulas (I), (II), (Ill), (IV), (V), (VI), (VII), and the subgroups therein described herein.

Methacrylamide compounds with a terminal hydroxyl group disclosed herein may be prepared by the synthesis scheme below.

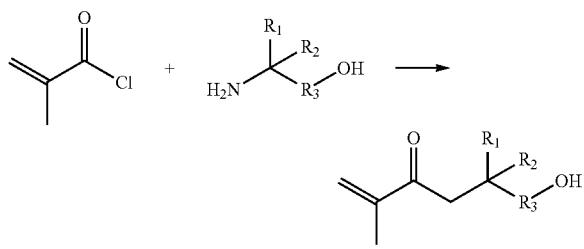

Definitions

The term "alkyl" refers to a straight or branched hydrocarbon. For example, an alkyl group can have 1 to 10 carbon atoms (i.e, $C_1$-$C_{10}$ alkyl or $C_{1-10}$ alkyl), 1 to 8 carbon atoms (i.e., $C_1$-$C_8$ alkyl or $C_{1-8}$ alkyl), or 1 to 6 carbon atoms (i.e., $C_1$-$C_6$ alkyl or $C_{1-6}$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkylene" refers to a bivalent saturated straight or branched aliphatic radical, including methylene, ethylene The term "initiator" or "polymerization initiator" herein refers to thermal initiating, redox-initiating, and/or photoinitiating compounds capable of inducing polymerization throughout a significant depth of composite material, such as camphorquinone (CQ); trimethylbenzoyl-diphenyl-phosphine oxide (TPO); Ethyl-4-dimethylamino benzoate (EDMAB); 2,2-Dimethoxy-2-phenylacetophenone (DMPA); Bisacylphosphine oxide (BAPO); 1-Phenyl-1,2-propanedione (PPD); phosphine oxide compounds, including naphthacene (APO), 9-anthracene (APO), and bisacylphosphine oxide (BAPO); 1-phenyl-1,2-propanedione (PPD); thioxanthone (TX) and its derivatives; dibenzoyl germanium derivatives, such as benzoyltrimethylgermane (BTG) and dibenzoyldiethylgermane; hexaarylbiimidazole derivatives; silane based derivatives; (diethylgermanediyl) bis((4-methoxyphenyl)methanone) (Ivocerin); benzenesulfinic acid sodium salt (BS); diaryliodonium salts (such as diphenyliodonium chloride or iodonium salt [diphenyliodonium hexafluorophosphate (DPIHP or DPI-PF6))], bromide, iodide, or hexafluorophosphate; and benzoyl peroxide (BPO). It is understood that in the compositions herein, one initiator material may be used or 2 or more may be used, such as the combination of camphorquinone with a co-initiator, such as a tertiary amine initiator (such as ethyl-4-(dimethylamino) benzoate (EDMAB) and/or 2-(dimethylamino)ethyl methacrylate (DMAEMA)), or a combination of DMPA/DPI-PF6, CQ/PPD, CQ/DMAEMA, CQ/EDMAB, CQ/DMAEMA/PDIHP, or CQ/EDMAB/DPIHP.

In ranges given herein it is understood that each whole number member of the range or group is included. For example, an alkylene chain for which the range of carbon atoms is described as from "10-16", "10 to 16", or "$C_{10}$-$C_{16}$" refers to an alkylene chain having 10, 11, 12, 12, 14, 15, or 16 carbon atoms.

It is understood herein that, in reference to or description of a subset or subgeneric group, aside from the specific variables noted (such as $R_1$, $R_2$, $R_3$, A, etc.), all other variables are as defined for the main or generic group. For instance, for a subset or subgeneric group referring to initial Formula (I) that defines only a set of entities from which $R_1$ may be chosen, the remaining variables of Formula (I) ($R_2$, $R_3$, A, etc.) are as defined in the broadest group or genus for Formula (I).

Commercially available photoinitiators for use with the present compositions include monoacylphoshine oxide (MAPO, available from Lucirin TPO, BASF), bisacylphosphine oxide (BAPO, Irgacure 819, Ciba Geigy), phenylpropanedione (PPD, Aldrich), and camphorquinone (CQ, Aldrich).

The terms "inhibitor" and "stabilizer" for use in the dental composites herein include butylated hydroxytoluene, butylhydroxytoluene, or 2,6-di(tert-butyl)-4-methylphenol (BHT); tert-butyl hydroquinone (TBHQ); 2,5-di-tert-butylhydroquinone (DTBHQ); monomethyl ether hydroquinone (MEHQ); 3,5-di-tert-butyl-4-hydroxyanisole (2,6-di-tert-butyl-4-ethoxyphenol); 2,5-di-tert-butyl hydroquinone; 2-(2'-hydroxy-5'-methylphenyl)-2H-benzotriazole; 2-(2'-hydroxy-5'-t-octylphenyl)-2H-benzotriazole; 2-hydroxy4-methoxybenzophenone (UV-9); 2-(2'-hydroxy-4',6'-di-tert-pentylphenyl)-2H-benzotriazole; 2-hydroxy-4-n-octoxybenzophenone; and 2-(2'-hydroxy-5'-methacryloxyethylphenyl)-2H-benzotriazole.

The terms "filler" or "dental filler" herein refer to glass filler particles useful as dental fillers in composites, including silica materials, glass fillers, alkaline glass fillers, metal oxides, and prepolymerized fillers. Conventional and commercially available fillers for use in the present compositions include silica oxides (silicon dioxide), aluminum oxide, titanium dioxide, zinc oxide, zirconium oxide, calcium oxide, phosphorus oxides, barium glass, strontium glass, quartz, barium aluminum silicate glass, barium borosilicate, lithium aluminum silicate, strontium aluminum silicate glass, and silicon dioxide.

The term "polymer" herein refers to a substance having a molecular structure consisting substantially or entirely of a number of similar chemical or molecular units bonded together, such as those of synthetic organic materials, including plastics and resins. The term "monomer" refers to an individual chemical or molecular unit that may be bonded together to form a polymer.

A "polymer network" is a three-dimensional configuration of polymers formed as a result of chemical interactions between linear polymer chains or the build-up of monomeric chain reactants.

An "interpenetrating polymer network" is a polymer comprising two or more networks that are at least partially interlaced on a polymer scale. The two or more networks of the interpenetrating polymer network are not covalently bonded to each other, but cannot be separated without breaking chemical bonds.

A "homogeneous polymer network" refers to a polymer network comprising substantially or purely of the same monomer units and relatively even formation of the polymers comprising the network. Homogenous polymer networks are generally obtained when a uniform distribution of functional groups reacts or polymerizes uniformly, producing an absence of structural defects. In contrast, a "heterogeneous polymer network" concerns a network formed by uneven development of molecular weight among the polymers forming the network. Heterogeneous polymer networks are often formed by rapid, uncontrolled polymerization kinetics. Network homogeneity or heterogeneity can be described using values obtained from dynamic mechanical analysis.

N-(2-(dimethylamino)ethyl)-N-methylmethacrylamide was prepared by using freshly distilled methacryloyl chloride (2 cm$^3$, 20.4 mmol) was dissolved in anhydrous dry chloroform (15 cm$^3$) and added dropwise under inert gas to a solution of 2-amino-2-methylpropan-1-ol (3.19 cm$^3$, 40.8 mmol) at 0° C. in anhydrous chloroform (20 cm$^3$). The reaction was stirred for a further 2 hrs at 0° C., and continued at room temperature for overnight. After filtrating the salt of acidified 1-hydroxy-2-methylpropan-2-aminium chloride, the filtrate was concentrated under reduced pressure to give impure colorless oil which was further chromatographed on silica gel (Merck Kieselgel 60 Å (0.035-0.070 mm mesh)), with methanol/ethyl acetate/hexanes as eluent, to afford the white powder N-(1-hydroxy-2-methylpropan-2-yl)methacrylamide (Structure 2dMM, below). The product was stored with monomethyl ether of hydroquinone (MEHQ) at 500 ppm in order to prevent unwanted polymerization. Percentage yield for this group of monomers was 45-63%.

Methacrylamide compounds with terminal carboxylic acid groups, including those below:

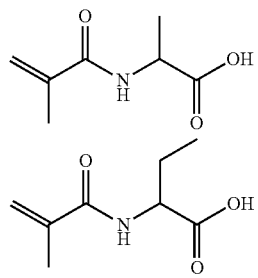
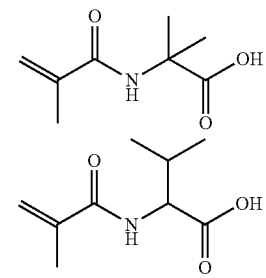

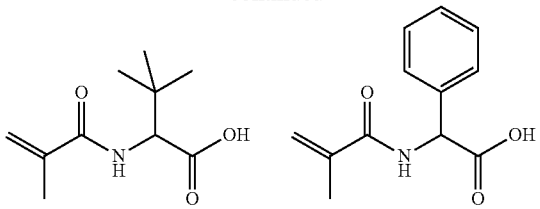

may be prepared by the reaction scheme:

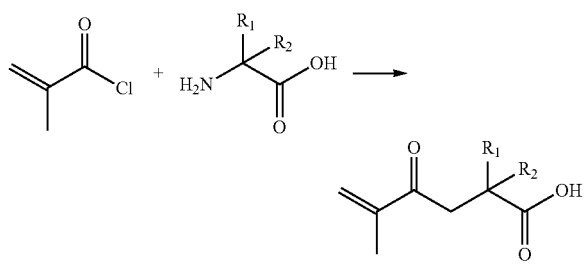

To a three-neck flask containing 12.0 g (0.3 mol) of NaOH, 13.4 g (0.15 mol) of alanine in 20 mL of water was added and cooled to 0-5° C. in an ice bath. Methacryloyl chloride (15.7 g, 0.15 mol) was added dropwise with vigorous stirring over a 15-min period. The reaction mixture was stirred for 30 min and then pH adjusted to 3 with 1M hydrochloric acid, whereupon a light oil separated. The reaction mixture was immediately filtered by vacuum to remove suspension with addition of 20 mL chloroform to extract the oily product and to reduce viscosity. The two layers were separated and the aqueous layer was again extracted with 3 portions of 15 mL chloroform. The chloroform layers were combined, dried over Na$_2$SO$_4$, and concentrated on a rotary evaporator. Careful addition of hexane caused precipitation of the product to give 17.6 g (75%) of crude solid. 14 g were obtained after recrystallization using benzene.

Methacrylamide compounds with terminal phosphoric acid groups, including the six groups below, wherein in each R$_3$ is independently C$_1$-C$_{16}$ alkylene:

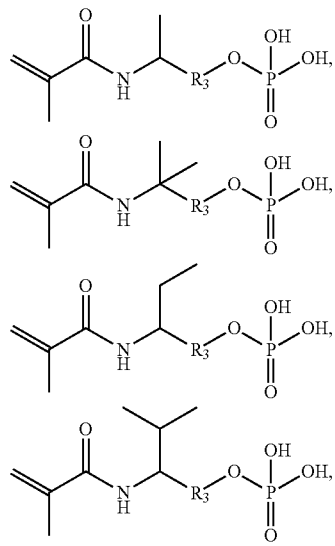

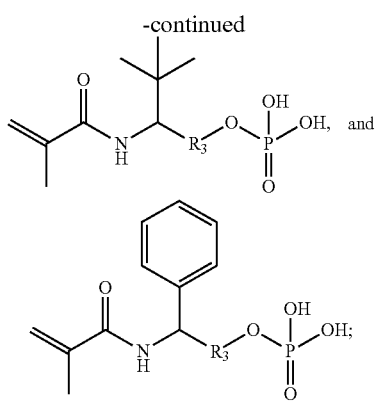

may be prepared by the synthetic scheme:

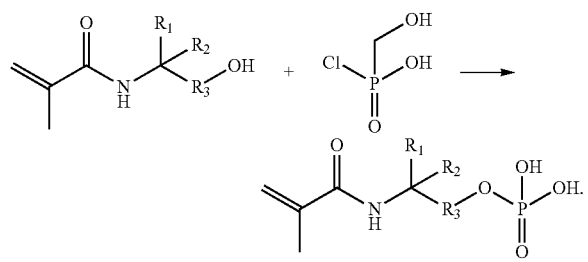

A 250 mL round bottom vessel in an ice bath was charged with 150 mL of cold acetone. Phosphorus pentoxide ($P_4O_{10}$) (5 mmol) was added and the slurry was vigorously stirred with a magnetic bar. 5 mmol methacrylamide monomer (synthesized using A1 method above) dissolved 10 mL acetone was added slowly drop wise using dropping funnel. The reaction was maintained at 0° C. for further 2 hours. The ice bath was removed and the reaction was continued at room temperature for another 2 hrs. The product was filtered, 0.004 g of 4-methoxyphenol (MEHQ) added and acetone evaporated in a rotatory evaporator.

Experimental adhesive resins were formulated with 60 wt % BisGMA (Bisphenol A glycerolate dimethacrylate) or UDMA (urethane dimethacrylate), both from ESSTECH (Essington, Pa., USA) and 40 wt % of one of the monofunctional monomers listed in Table 1 (synthesis procedures and characterization of monomers, including 1H-NMR spectra and log P calculations obtained with Chem Draw software are detailed for the novel monomers). In all formulations, the photoinitiator system was composed by 0.2 wt. % of the alpha-cleavage type single component 2,2-Dimethoxy-2-phenylacetophenone (DMPA) and 0.4 wt % Diphenyl Iodonium Hexafluorophosphate (DPI-PF6). This initiator composition was determined in a pilot study as providing the best compromise between adequate reactivity and high final conversion for the monomers tested. 0.1 wt % butylated hydroxytoluene (BHT) was used as an inhibitor for shelf life. 40 vol % ethanol was added only for the materials to be used for microtensile bond strength tests.

TABLE 1

Monofunctional monomers comprising 40 wt % of the adhesive formulation. Monomer acronyms, IUPAC names, classification, chemical structure and molecular weight are depicted for commercial products (marked with *), as well as newly synthesized compounds.

| Monomer | Classification | Chemical Structure | Molecular Weight (MW) |
|---|---|---|---|
| HEMA * 2-Hydroxyethyl methacrylate | Methacrylate | 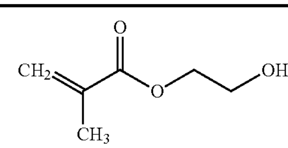 | 130.14 |
| HEA * 2-Hydroxyethyl acrylate | Acrylate | 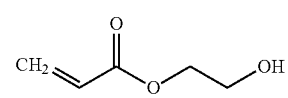 | 116.11 |
| HEMAM * N-Hydroxyethyl methacrylamide | Secondary methacrylamide | 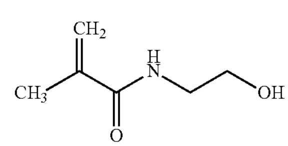 | 129.15 |
| HEAM * N-Hydroxyethyl acrylamide | Secondary acrylamide | 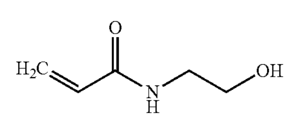 | 115.13 |
| HEM N-(2-hydroxyethyl)-N-methylacrylamide | Tertiary acrylamide | 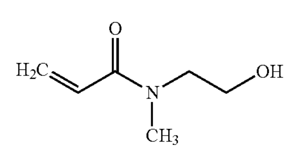 | 129.07 |

TABLE 1-continued

Monofunctional monomers comprising 40 wt % of the adhesive formulation. Monomer acronyms, IUPAC names, classification, chemical structure and molecular weight are depicted for commercial products (marked with *), as well as newly synthesized compounds.

| Monomer | Classification | Chemical Structure | Molecular Weight (MW) |
|---|---|---|---|
| HEMMA N-(2-hydroxyethyl)-N-methylmethacrylamide | Tertiary methacrylamide | 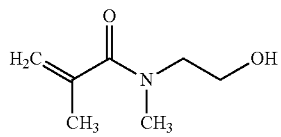 | 143.18 |
| DMAM * N,N-Dimethylacrylamide | Tertiary Acrylamide | | 99.13 |
| 2EM N-(1-hydroxybutan-2-yl)methacrylamide | Secondary alpha-substituted methacrylamide | 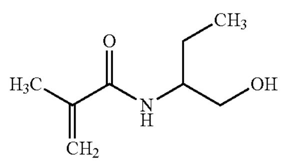 | 157.11 |
| 2dMM N-(1-hydroxy-2-methylpropan-2-yl)methacrylamide | Secondary alpha-substitute methacrylamide | 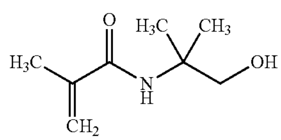 | 157.21 |

A

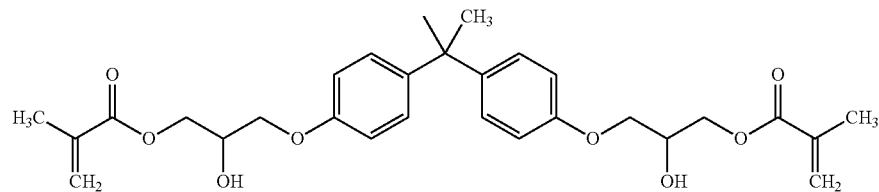 [SMILES: C=C(C)C(=O)OCC(O)COc1ccc(C(C)(C)c2ccc(OCC(O)COC(=O)C(=C)C)cc2)cc1]

MW=512.24 and log P=5.09

B

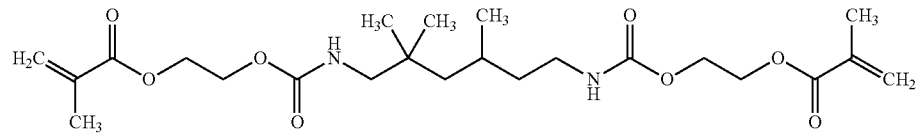 [SMILES: C=C(C)C(=O)OCCOC(=O)NCCC(C)CC(C)(C)CNC(=O)OCCOC(=O)C(=C)C]

MW=470.55 and log P=3.64

Base monomers used for copolymerization, above. (A) BisGMA (bisphenol A and glycidyl methacrylate) and (B) UDMA (urethane dimethacrylate).

Synthesis Procedures for the Monofunctional Monomers:

General considerations: Unless otherwise stated, all reagents and solvents were purchased from commercial suppliers (Sigma-Aldrich, Fisher Scientific) and used without further purification. All reactions were conducted in standard, dry glassware and under an inert atmosphere of nitrogen. $^{13}$C-NMR and $^{1}$H-NMR spectra were recorded at room temperature on a Bruker AMX-400 MHz spectrometer using acetone-$d_6$ or CDCl$_3$. Chemical shifts are reported as δ values in parts per million (ppm) and coupling constants (J) are reported in Hertz. When required, a Buchi Reveleris X2 flash chromatography system was used with 20 μm particle size, 40 g silica cartridges at a flow rate of 40 mL/min, with peak detection programmed to 254 nm.

N-(2-hydroxyethyl)-N-methylmethacrylamide (MEMA): Freshly distilled methacryloyl chloride (20.5 mmol, 1 equiv.) in anhydrous DCM (10 mL) was added dropwise to a stirred solution of 2-methylaminoethanol (21.25 mmol, 1.05 equiv.), trimethylamine (20.5 mmol, 1 equiv.) and 2 mg of 4-methoxyphenol in anhydrous DCM (20 mL) at −10° C. After the addition was complete, the mixture was allowed to stir at to room temperature at for 36 h. The mixture was then filtered and the liquid portion was washed with 0.1 M HCl solution. The organic layer was dried over MgSO$_4$, filtered and the solvent removed vacuo to give the title compound as pale yellow oil (31% yield). $^1$H NMR (400 MHz, acetone-d$_6$) δ 5.12 (b, 1H), 5.02-4.96 (m, 1H), 4.22-3.94 (m, 1H), 3.67 (t, J=5.6 Hz, 2H), 3.50 (m, 2H), 3.00 (d, J=77.1 Hz, 3H), 1.92-1.87 (m, 3H). $^{13}$C NMR (101 MHz, CDCl$_3$): δ 173.1, 142.4, 114.8, 60.2, 51.9, 35.3, 20.7.

N-(2-hydroxyethyl)-N-methylacrylamide (HEM): Freshly distilled acryloyl chloride (24.7 mmol, 1 equiv.) in anhydrous DCM (10 mL) was added dropwise to a stirred solution of 2-methylaminoethanol (25.94 mmol, 1.05 equiv.), trimethylamine (24.7 mmol, 1 equiv.) and 2 mg of 4-methoxyphenol in anhydrous DCM (20 mL) at −10° C. After the addition was complete, the mixture was allowed to stir at to room temperature at for 36 h. The mixture was then filtered and the liquid portion was washed with 0.1 M HCl solution. The organic layer was dried over MgSO$_4$, filtered and the solvent removed vacuo to give the title compound as pale yellow oil (20% yield). $^1$H NMR (400 MHz, acetone-d$_6$) δ 6.68-6.86 (m, 1H), 6.12-6.22 (m, 1H), 5.54-5.68 (m, 1H), 3.96-4.40 (m, 2H), 3.68 (dt, J=10.1, 5.7 Hz, 2H), 3.52 (dt, J=6.9, 5.7 Hz, 2H), 2.91-3.22 (m, 3H). $^{13}$C NMR (101 MHz, CDCl$_3$): δ 166.8, 129.4, 126.8, 60.6, 51.9, 35.5.

N-(1-hydroxy-2-methylpropan-2-yl)methacrylamide (2dMM): Freshly distilled methacryloyl chloride (51.2 mmol, 1 equiv.) in anhydrous DCM (40 mL) was added dropwise to a stirred solution of 2-amino-2-methyl-1-propanol (53.55 mmol, 1.05 equiv.), trimethylamine (51.2 mmol, 1 equiv.) and 5 mg of 4-methoxyphenol in anhydrous DCM (80 mL) at −10° C. After the addition was complete, the mixture was allowed to stir at to room temperature at for 36 h. The mixture was then filtered and the liquid portion was washed in turn with 60 mL of 0.1 M HCl solution, 5% NaHCO$_3$, and brine. The organic layer was dried over MgSO$_4$, filtered and reduced in vacuo to give the crude product as pale yellow oil. The crude product was purified using a Buchi Reveleris X2 flash chromatography system (mobile phase A was hexanes and mobile phase B (MPB) was EtOAc, with a gradient program of 11% MPB for 1 min, 11% MPB to 47% MPB over 14.3 min and hold at 47% for 7.2 min). The fractions were collected and the solvent removed in vacuo, yielding the final product as a colorless oil (30% yield). $^1$H NMR (400 MHz, CDCl$_3$): δ 6.03 (s, 1H), 5.62-5.58 (m, 1H), 5.30-5.24 (m, 1H), 4.96 (t, J=6.0 Hz, 1H), 3.53 (d, J=5.9 Hz, 2H), 1.89 (s, J=1.2 Hz, 1H), 1.28 (s, 6H). $^{13}$C NMR (101 MHz, CDCl$_3$): δ 169.5, 140.2, 119.8, 70.6, 56.0, 24.4, 18.7.

N-(1-hydroxybutan-2-yl)methacrylamide (2EM): Under a N$_2$ atmosphere, freshly distilled methacryloyl chloride (51.2 mmol, 1 equiv.) in anhydrous DCM (40 mL) was added dropwise to a stirred solution of 2-amino-1-butananol (53.55 mmol, 1.05 equiv.), trimethylamine (51.2 mmol, 1 equiv.) and 5 mg of 4-methoxyphenol in anhydrous DCM (80 mL) at −10° C. under inert atmosphere (nitrogen gas). After the addition was complete, the mixture was allowed to stir at to room temperature at for 36 h. The mixture was then filtered and the liquid portion was washed in turn with 60 mL of 0.1 M HCl solution, 5% NaHCO$_3$, and brine. The organic layer was dried over MgSO$_4$, filtered and reduced in vacuo to give the crude product as pale yellow oil. The crude product was purified using a Buchi Reveleris X2 flash chromatography system (mobile phase A was hexanes and mobile phase B (MPB) was EtOAc, with a gradient program of 29% MPB for 1 min, 29% MPB to 74% MPB over 14.3 min, hold at 74% for 7.3 min). The fractions were collected and the solvent removed in vacuo, yielding the final product as a colorless oil (12% yield). $^1$H NMR (400 MHz, CDCl$_3$): δ 6.07 (s, 1H), 5.70 (s, 1H), 5.33 (s, 1H), 3.96-3.82 (m, 1H), 3.75-3.55 (m, 2H), 3.23 (s, 1H), 1.95 (s, 3H), 1.73-1.42 (m, 2H), 0.95 (t, J=7.5 Hz, 3H). $^{13}$C NMR (101 MHz, CDCl$_3$) δ 169.4, 140.0, 120.0, 65.2, 53.5, 24.3, 18.8, 10.7.

Additional methacrylate base monomers used in enamel and dentin bonding agents useful in the present compositions include the following monomers with surface active and/or adhesive functional groups:
2-hydroxyethyl methacrylate (HEMA);
2-hydroxyethyl methacrylate phosphate (HEMA-phosphate);
2-methacryloyloxyethylphenyl hydrogen phosphate (Phenyl-P);
10-(phosphonooxy)decyl methacrylate (10-MDP);
4-((2-(methacryloyloxy)ethoxy)carbonyl)phthalic acid (4-MET);
4-(2-methacryloyloxyethyl)trimellitic anhydride (4-META);
2-[10-[(2-methyl-1-oxo-2-propen-1-yl)oxy]decyl]-propanedioic acid (MAC-10); and
N-(2-hydroxy-3-(methacryloyloxy)propyl)-N-(p-tolyl)glycine (NPG-GMA).

Additional useful monomers with crosslinking and copolymerizing functions include:
((propane-2,2-diylbis(4,1-phenylene))bis(oxy))bis(2-hydroxypropane-3,1-diyl) bis(2-methylacrylate) (BisGMA);
7,7,9-trimethyl-4,13-dioxo-3,14-dioxa-5,12-diazahexadecane-1,16-diyl bis(2-methylacrylate) (UDMA); and
(ethane-1,2-diylbis(oxy))bis(ethane-2,1-diyl) bis(2-methylacrylate) (TEGDMA).

Polymerization Kinetics

Disk samples (10 mm diameter, 0.6 mm thick) sandwiched between two glass slides were placed in the chamber of an infra-red spectrometer (Nicolet 6700, ThermoScientific, USA) and irradiated with a mercury arc lamp (Acticure, EXFO Acticure 4000 UV Cure; Mississauga, Ontario, Canada) filtered to 320-500 nm at 630 mW/cm$^2$, for 300 s, delivering 630 mW/cm$^2$ directly to the specimen. Spectra were collected in real-time during photoactivation, with 2 scans per spectrum at 4 cm$^{-1}$ resolution. The degree of conversion was calculated based on the area of the vinyl overtone in near-IR at 6165 cm$^{-1}$ for methacrylates and around 6130 cm$^{-1}$ for (meth)acrylamides. Clear, distinct separation of the peaks was only possible for one group (BisGMA-HEMMA), whereas in the other groups the peaks were more severely convoluted. For BisGMA-HEMMA, the conversion of each peak was calculated as previously described (Rueggeberg et al., J Dental Res., 1988; 67:932-7; and Rueggeberg et al., Calibration of FTIR conversion analysis of contemporary dental resin composites, Dental Materials: Official publication of the Academy of Dental Materials, 1990; 6:241-249). The rate of polymerization was calculated as the first derivative of the conversion vs. time curve (Stansbury and Dickens, Dental Materials, 2001, 17, pp. 71-79).

Water Sorption and Solubility

The same samples used in the polymerization kinetics test were stored dry at room temperature for 24 hs, then used for the water sorption (WS) and solubility (SL) test, according to ISO 4049 (REF). The initial mass (M1) was recorded and the volume calculated following the equation:

$$V = h \times \pi r^2$$

where h (mm) is the sample height and r (mm) is the sample radius.

Each sample was placed in a tight-close glass vial with 5 glass beads on the bottom to ensure the whole surface of the sample was exposed to water, and then the vial was filled by 5 ml of double-distilled water and kept closed for one week. The samples were then removed from water, patted dry and weighed again (M2) and placed in a desiccator until mass stabilization (M3) was observed. Water sorption (WS) and solubility (SL) were calculated according to the equations:

$$WS = \left(\frac{M2 - M3}{V}\right) \text{ and } SL = \left(\frac{M1 - M3}{V}\right)$$

and the results were converted into $\mu m/mm^3$, where V is the volume of the specimen.

Dentin Microtensile Bond Strength

For the bonding procedures, forty-eight caries-free extracted human third molars (n=6) were collected from patients after informed consent. This study was cleared by the Oregon Health and Science University IRB. Teeth were cleaned and kept in 0.5% chloramine and used within 3 months after extraction. The enamel was removed to exposure a flat dentin surface which was wet polished with 600-grit silicon-carbide paper for 30 s to standardize the smear layer. The dentin surface was etched with 37% phosphoric acid for 15 s, water rinsed for 15 s and carefully dried with cotton pellets in order to maintain the surface slightly wet. The first adhesive coat was vigorously applied for 20 s, the solvent evaporated by a gentle air stream for 10 s, a second adhesive coat was a applied for 10 s and photocured for 60 s at 630 mW/cm² (Acticure). Single Bond Universal Adhesive and CLEARFIL™ SE Bond were applied following the manufacturer's instructions and photoactivation procedures were carried out with DEMI™ Plus Dental Curing Light (Kerr Dental) at 800 mW/cm². Resin blocks (FILTEK™ Supreme, shade body A2) were built on the bonded surfaces in 2 increments, with 2.0 mm thickness each, and photocured for 20 seconds (DEMI™ Plus) at 800 mW/cm². The teeth were immersed in distilled water and kept at 37° C. for 24 h.

Specimens were sectioned perpendicular to the interface using an automated precision water-cooled diamond saw (Accutom-50) to obtain rectangular slabs which were then further sectioned perpendicularly to produce bonded sticks approximately 1.0 mm² in cross section. The sticks were immersed in distilled water at 37° C. and half of them was tested after 24 hours and the other half after 3 weeks.

The tensile testing was performed to failure in a universal testing machine (model machine) at a crosshead speed of 0.05 mm/min. The bonded surface area was calculated after measuring each stick with a digital caliper (Mitutoyo, Tokyo, Japan). Each stick was attached to the grips of a microtensile device (Odeme Equipamentos, Brazil) with a cyanoacrylate adhesive (Super Glue; Henkel/Loctite, Westlake, Ohio, USA). The results were recorded in MPa and sticks for each tooth were averaged to provide one value per tooth. These values were then averaged for each group (n=6) and reported as the MTBS in MPa.

Mechanical Properties

Figure 5A:
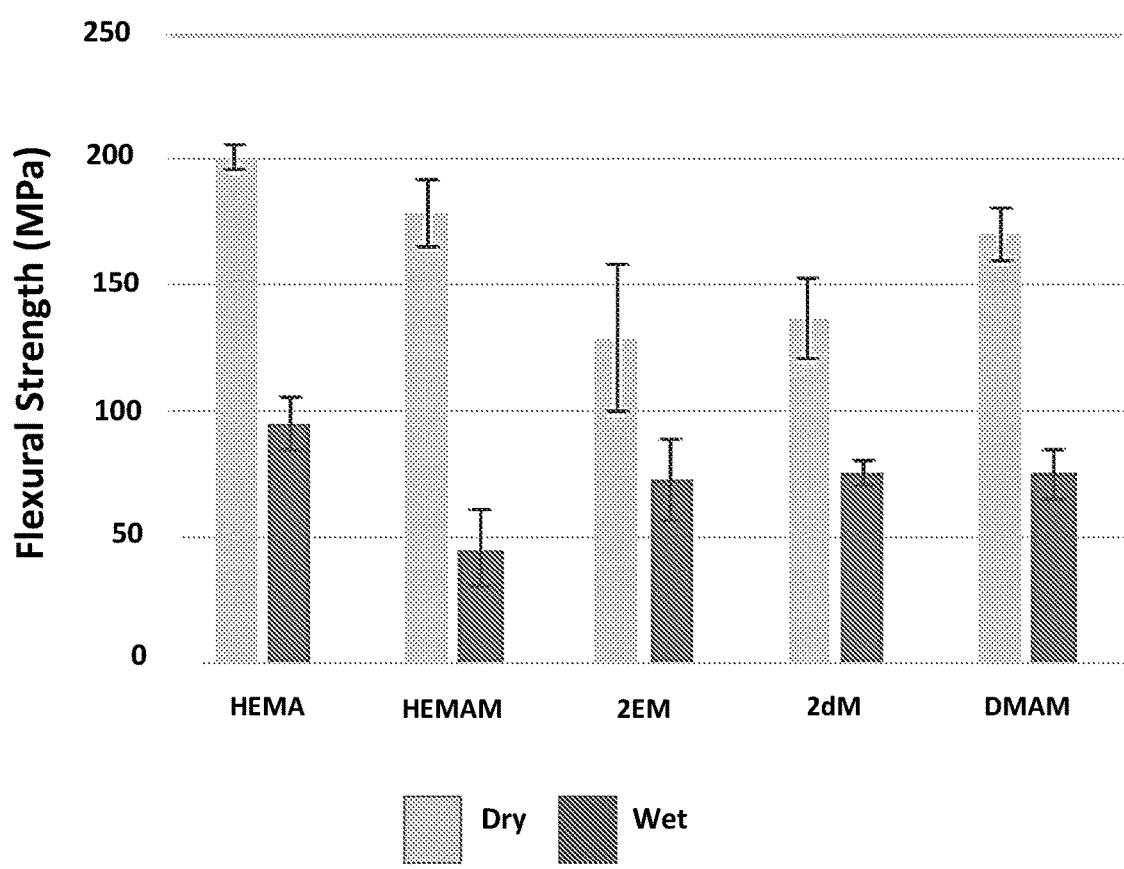
FIGS. 5A, 5B, and 5C depict flexural strength (FS), elastic modulus (E), and yield strength (YS) determined for HEMMA, HEMAM, 2Dmm, and DMAM in combination with BisGMA.
Figure 5B:
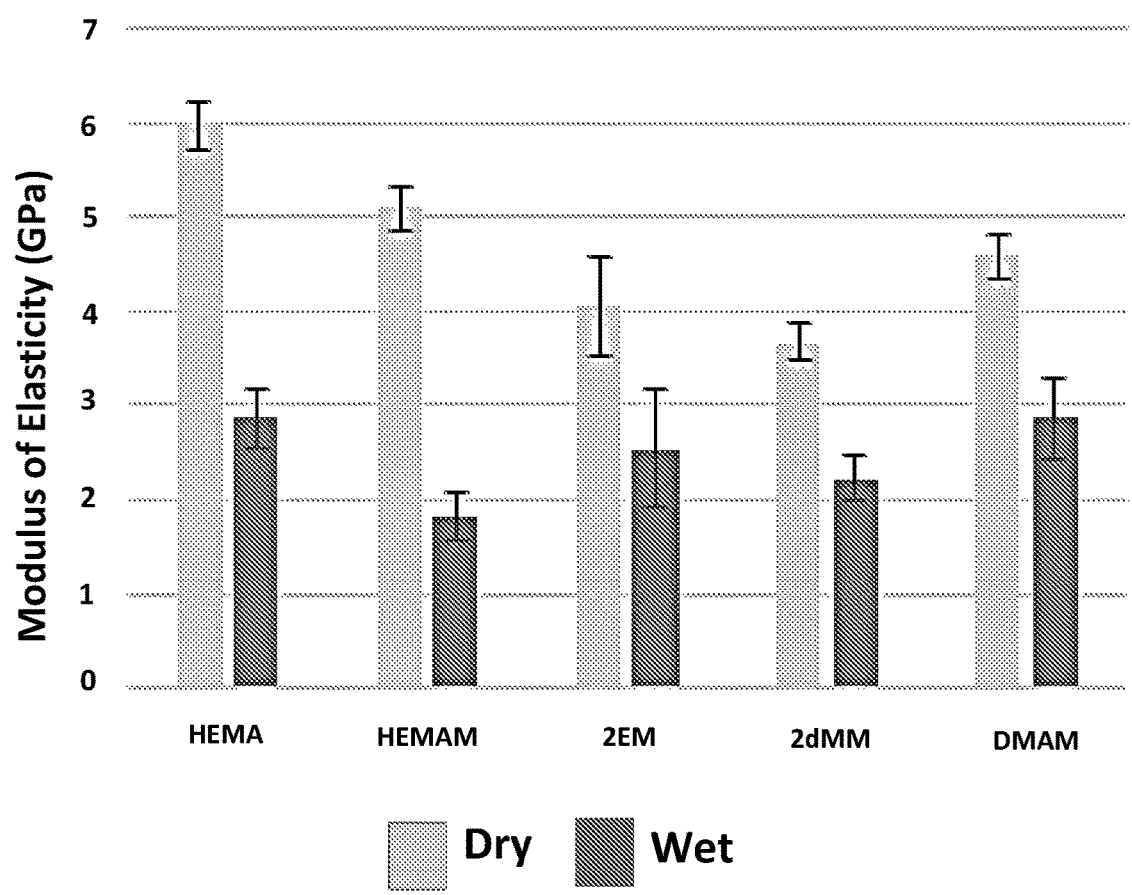
Figure 5C:
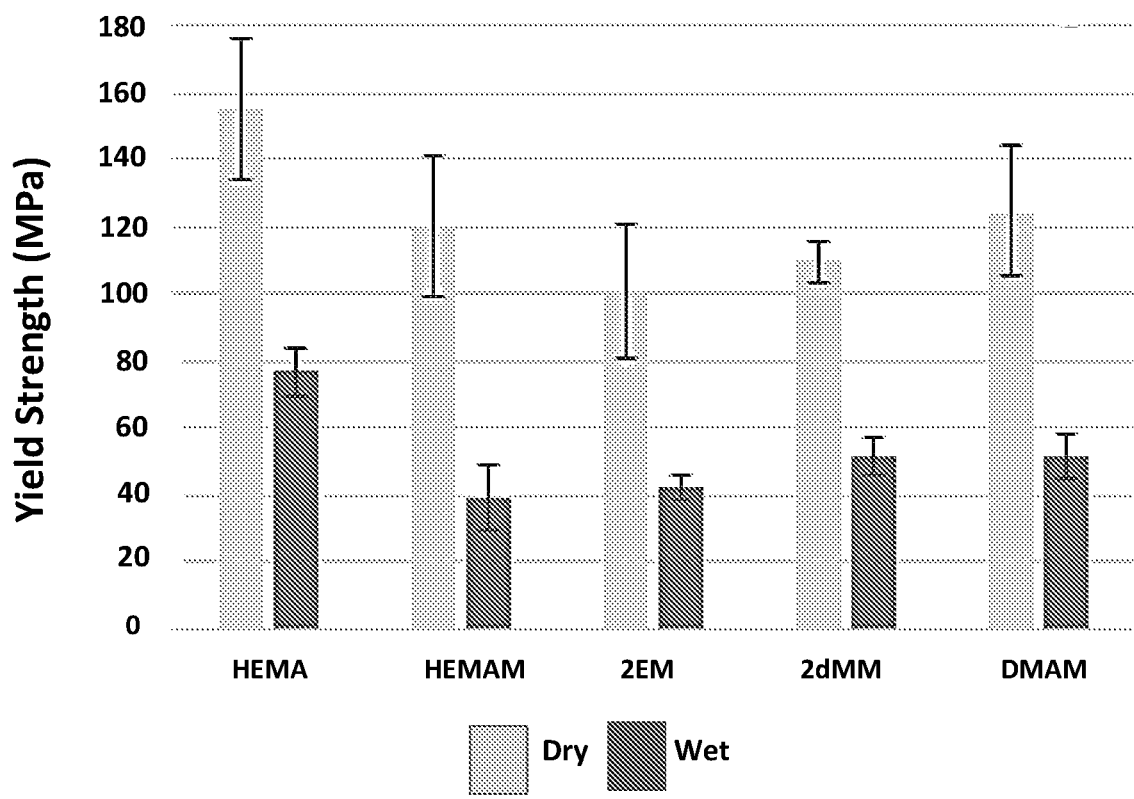
Figure 6A:
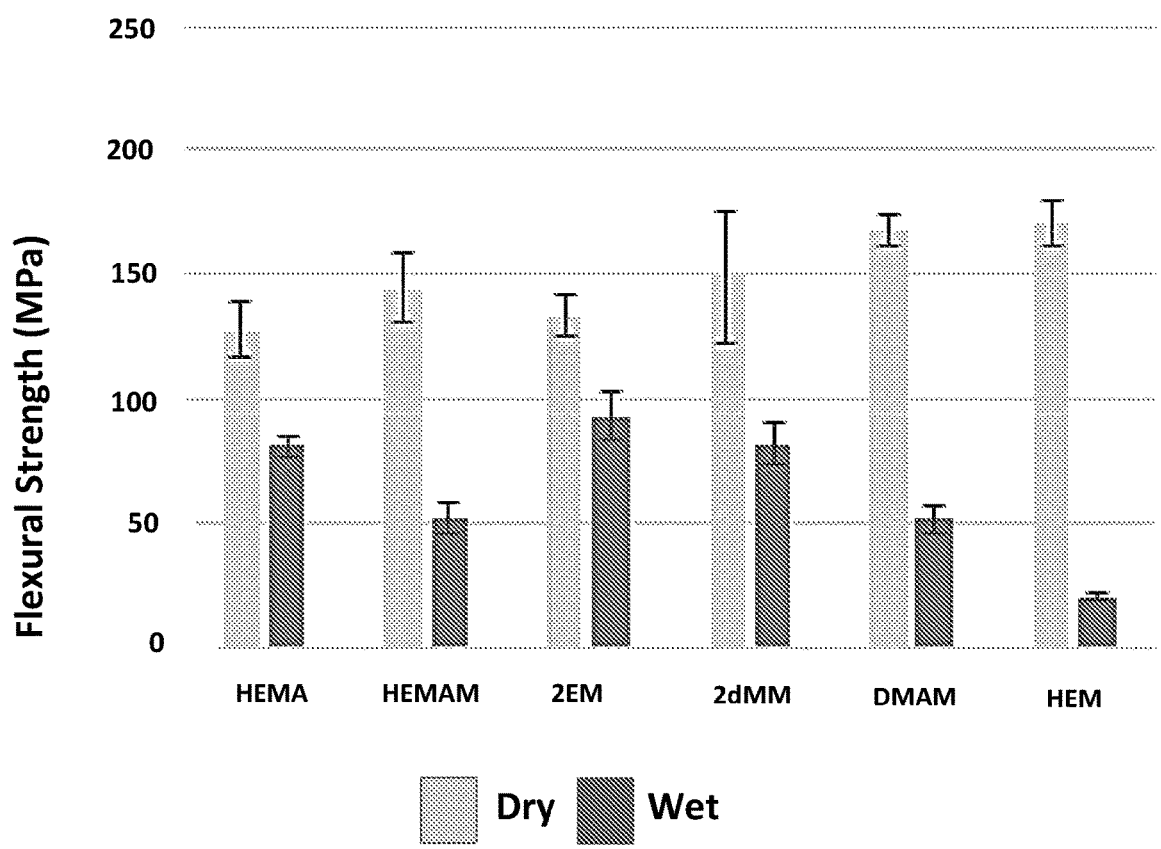
FIGS. 6A, 6B, and 6C depict flexural strength (FS), elastic modulus (E), and yield strength (YS) determined for HEMMA, HEMAM, 2Dmm, and DMAM in combination with UDMA.
Figure 6B:
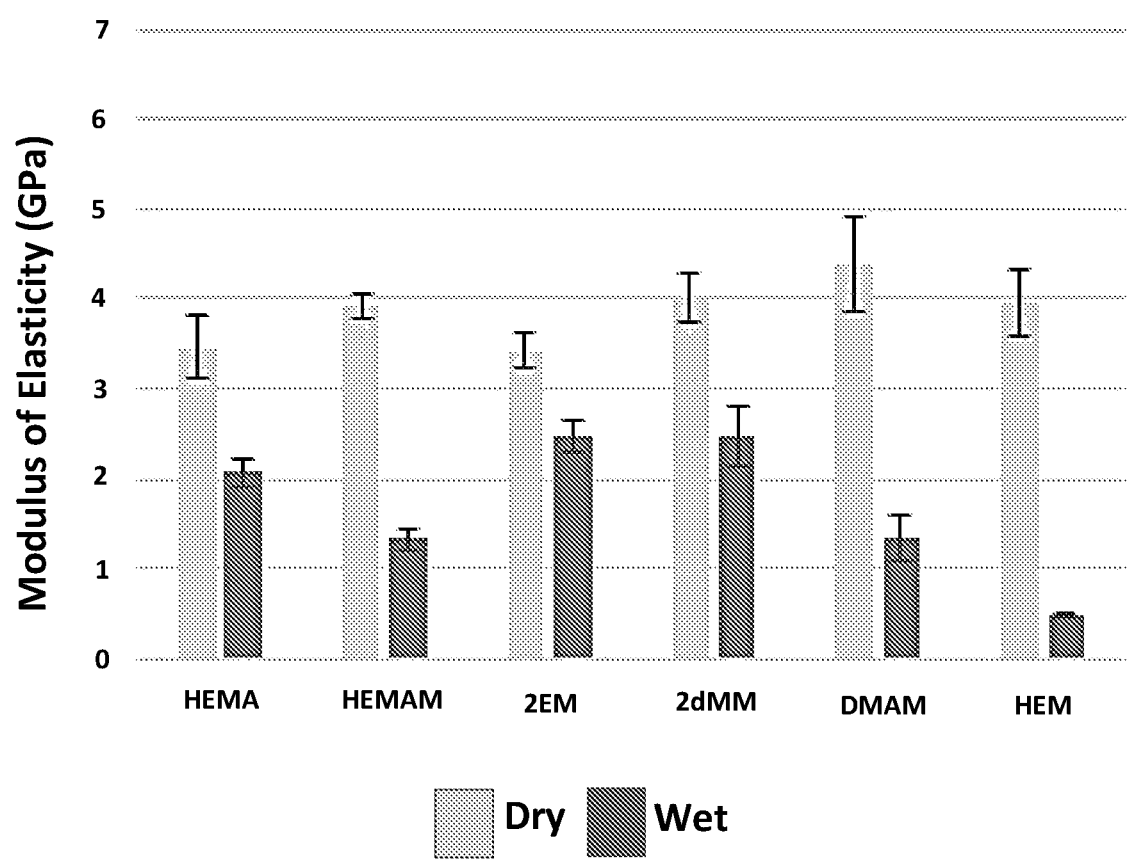
Figure 6C:
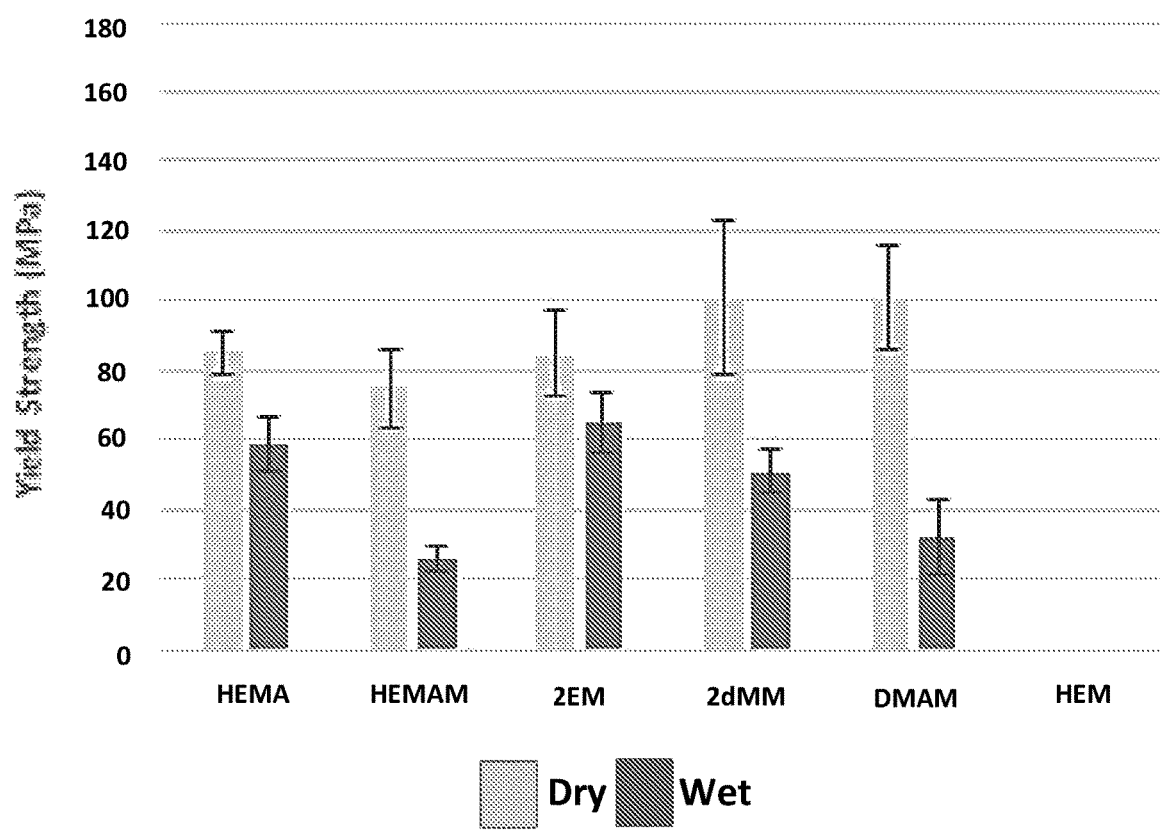
Figure 7:
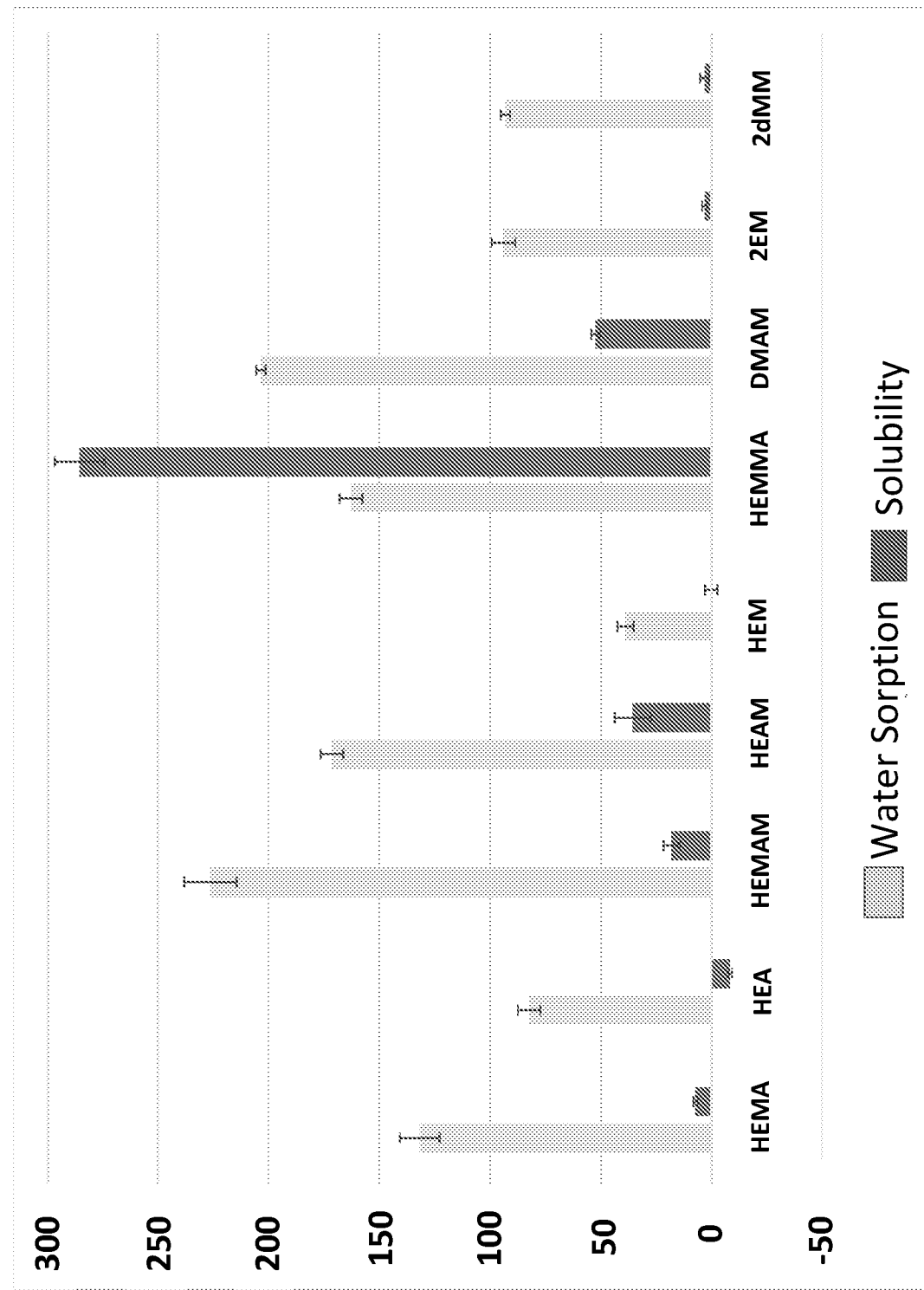
FIG. 7 depicts water sorption and solubility reading determined with HEMA, HEA, HEMAM, HEAM, HEM, HEMMA, DMAM, 2EM, AND 2dMM combined with BisGMA.
Figure 8:
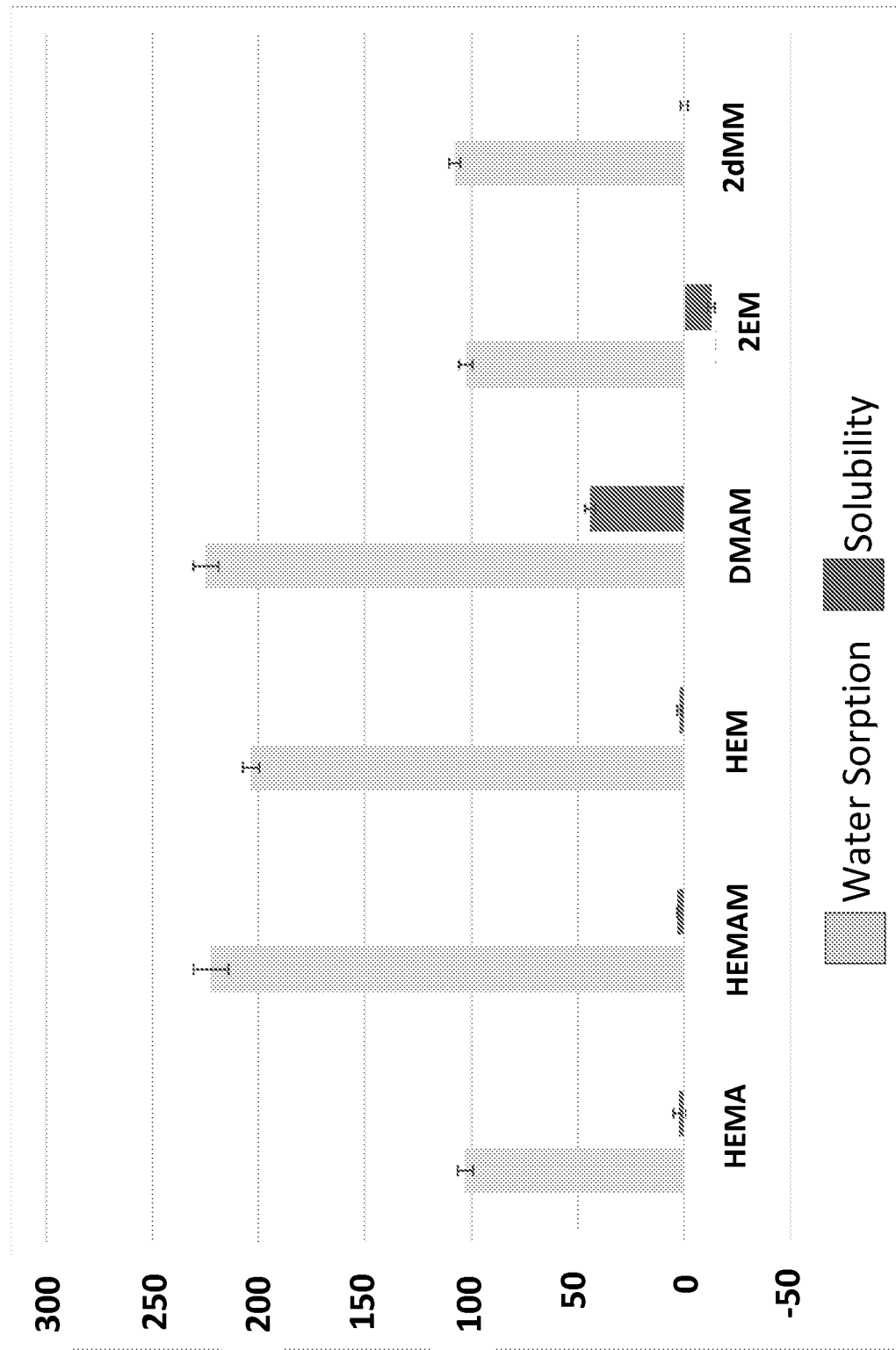
FIG. 8 depicts water sorption and solubility reading determined with HEMA, HEMAM, HEM, DMAM, 2EM, and 2dMM combined with UDMA.

The flexural strength (FS), elastic modulus (E), and yield strength (YS) were analyzed using three-point bending, according to ISO 4049, and are depicted in FIG. 5. Twelve rectangular bars (2.0×2.0×25.0 mm) per group were obtained from silicone molds placed between two glass slides. Half were submitted to the test after 24 hours dry storage, and the other half after 7 days water storage at room temperature. Specimens were tested at 0.5 mm/min of cross-head speed, with 20 mm between supports. Elastic modulus (GPa) was calculated according to equation (1):

$$E = \frac{L \times D^3}{4 \times w \times h^3 \times d} \times 10^{-3} \quad (1)$$

where L is the maximum load (N), D the span between the supports (mm), w the specimen width (mm), h the specimen height (mm), and d the deflection corresponding to L (mm).

Flexural Strength (MPa) was calculated according to equation (2):

$$FS = \frac{3 \times F \times L}{2 \times w \times h^2} \quad (2)$$

Yield strength values (MPa) were obtained for all materials for accurate comparisons of material strength before any plastic deformation occurred. This was achieved by applying a 0.2% offset from the initial elastic region on a stress-strain curve.

Statistical Analysis

After normality and homoscedasticity tests, the data was analyzed with one-way ANOVA and Tukey's test for comparisons among means. The confidence level was set at 95%.

Polymerization Kinetics

Figure 1B:
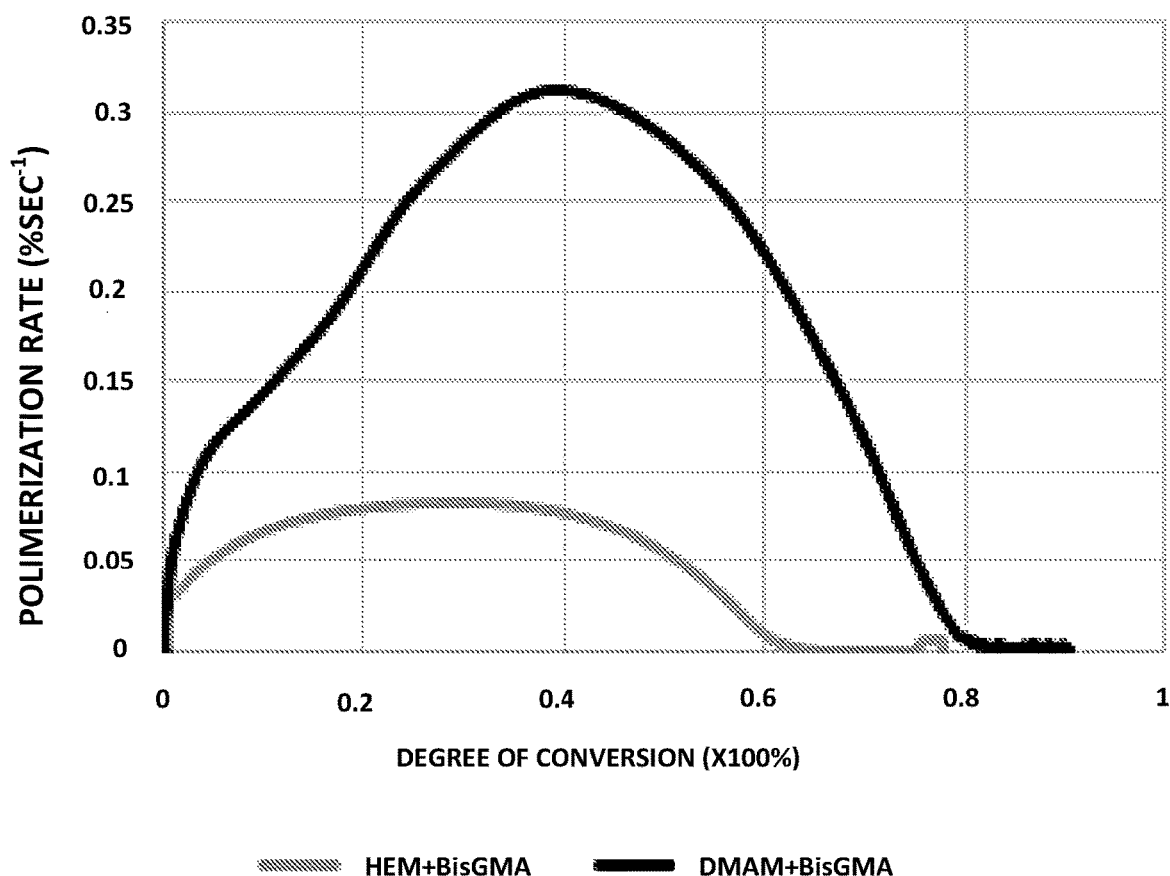
Figure 1C:
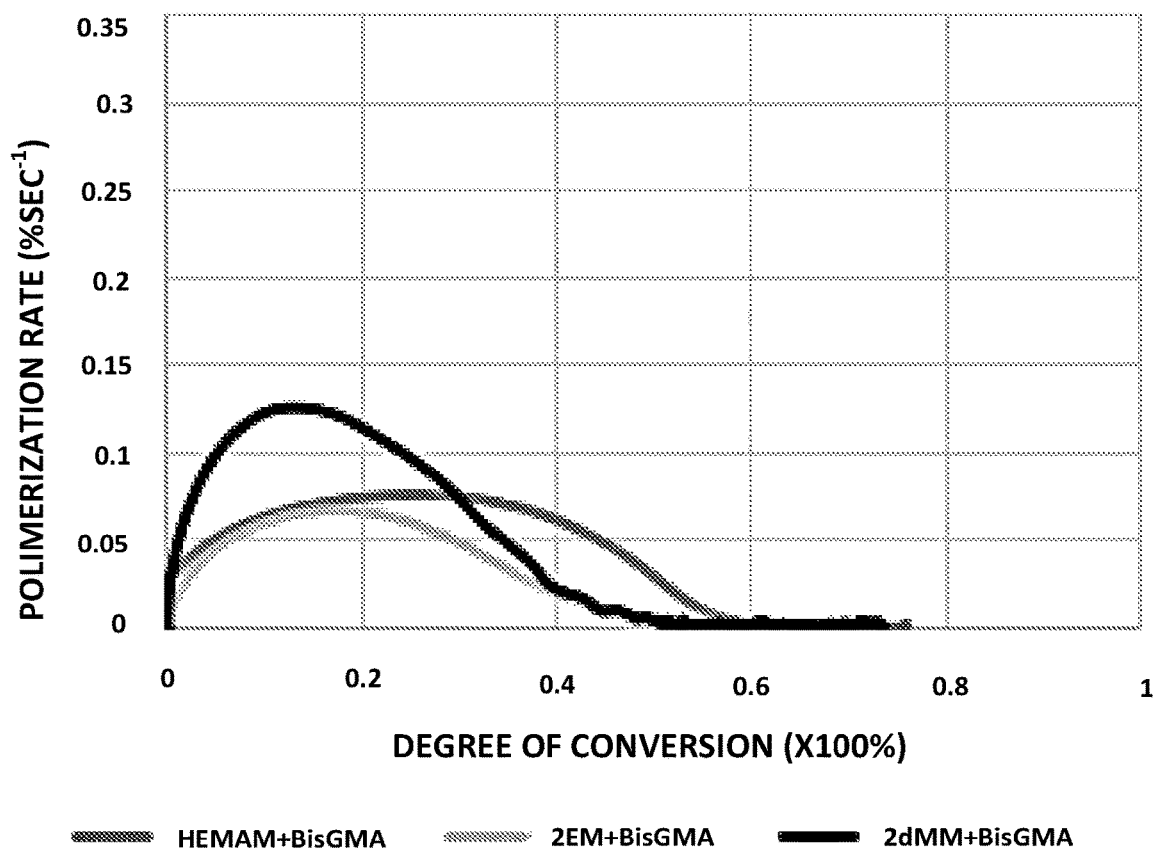
Figure 2A:
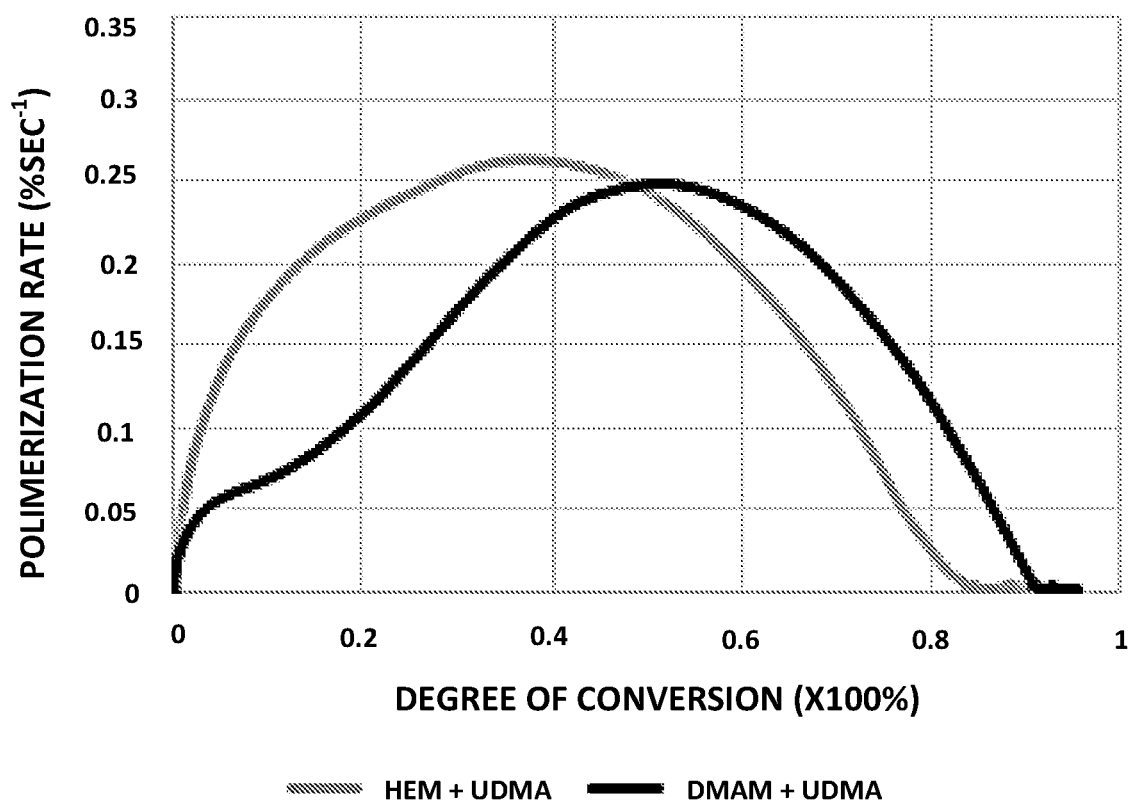
FIGS. 2A, 2B, and 2C depict the degree of conversion for UDMA-containing resin combinations tested.
Figure 2B:
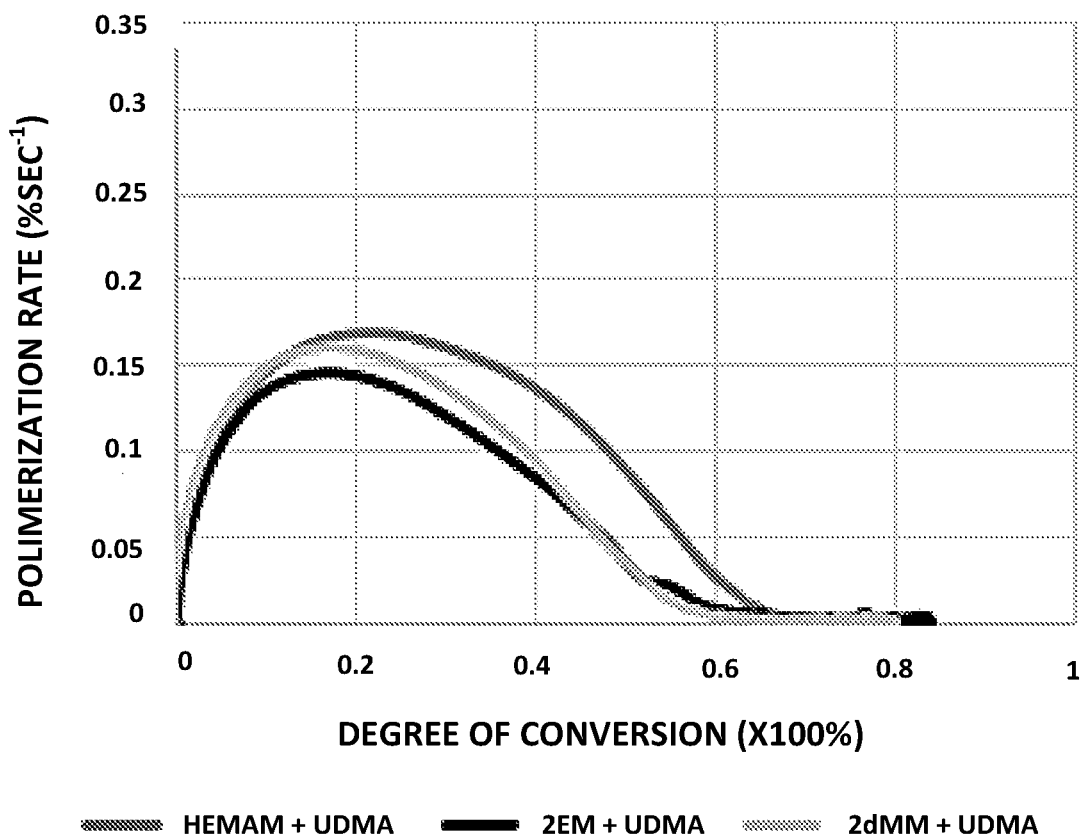
Figure 2C:
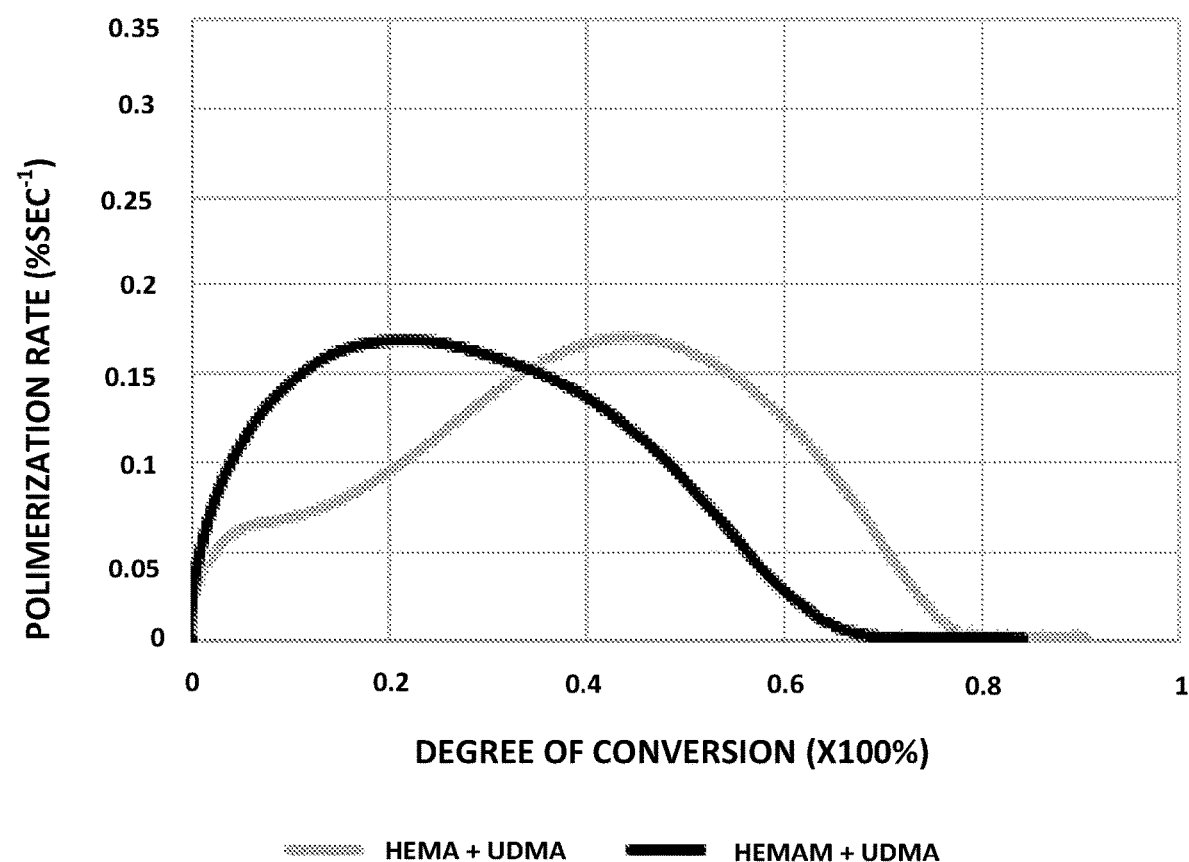
Figure 3A:
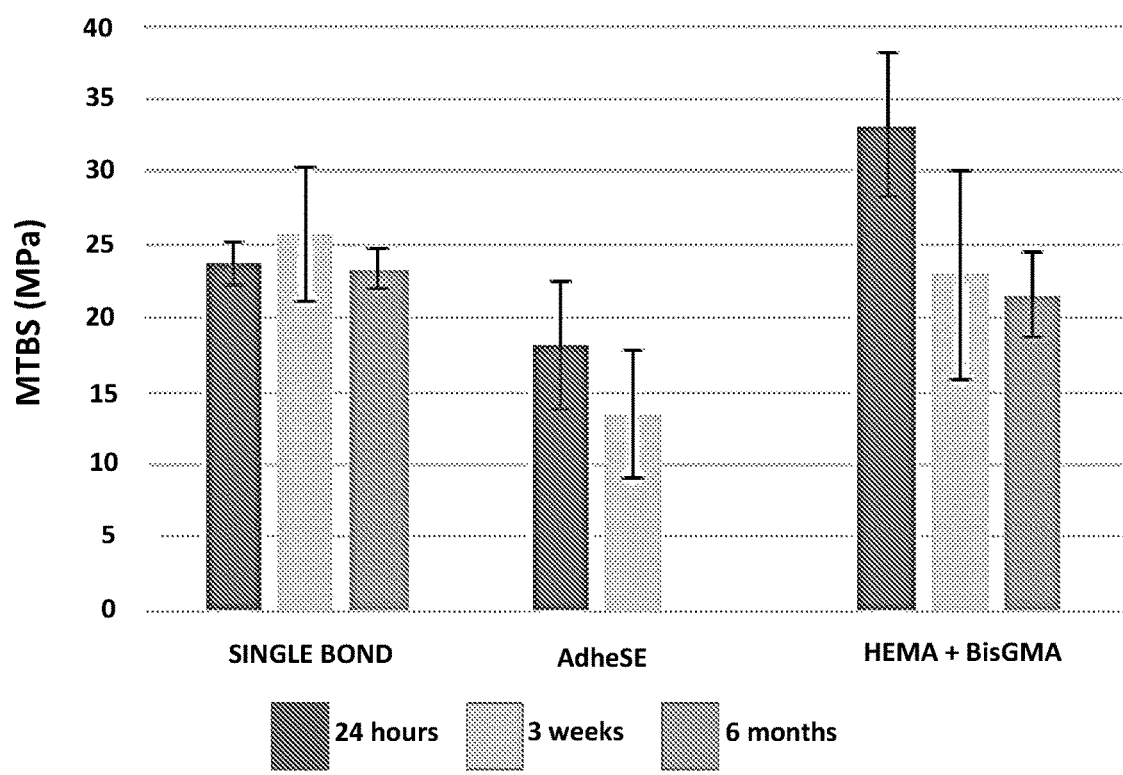
FIGS. 3A, 3B, 3C, and 3D depict dentin microtensile bond strength (MPa) comparisons for adhesives and control groups after 24 hours, 3 weeks, and 6 months of water storage.
Figure 3B:
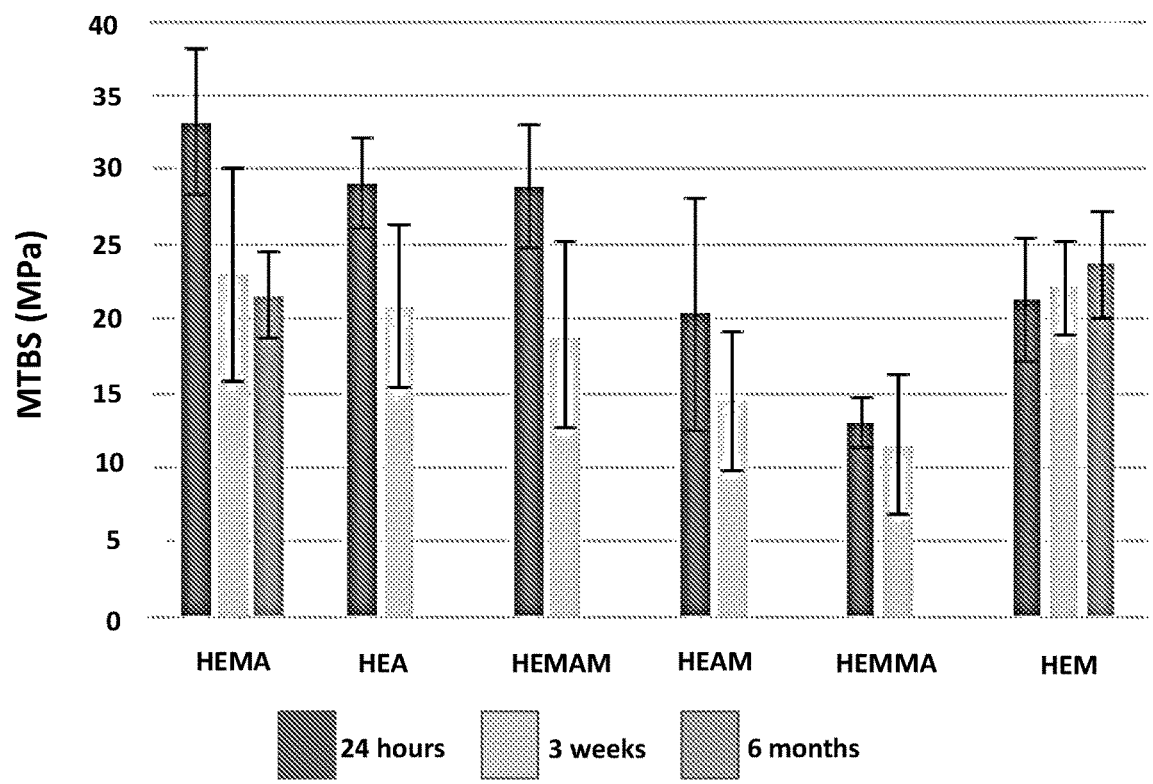
Figure 3C:
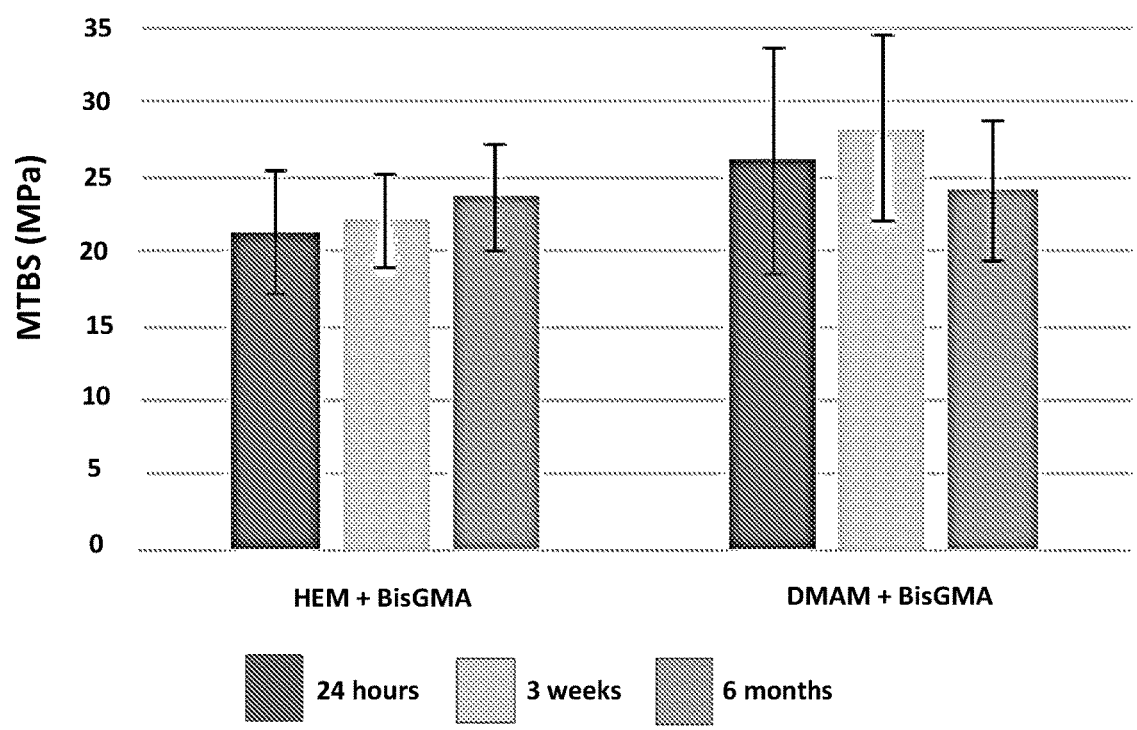
Figure 3D:
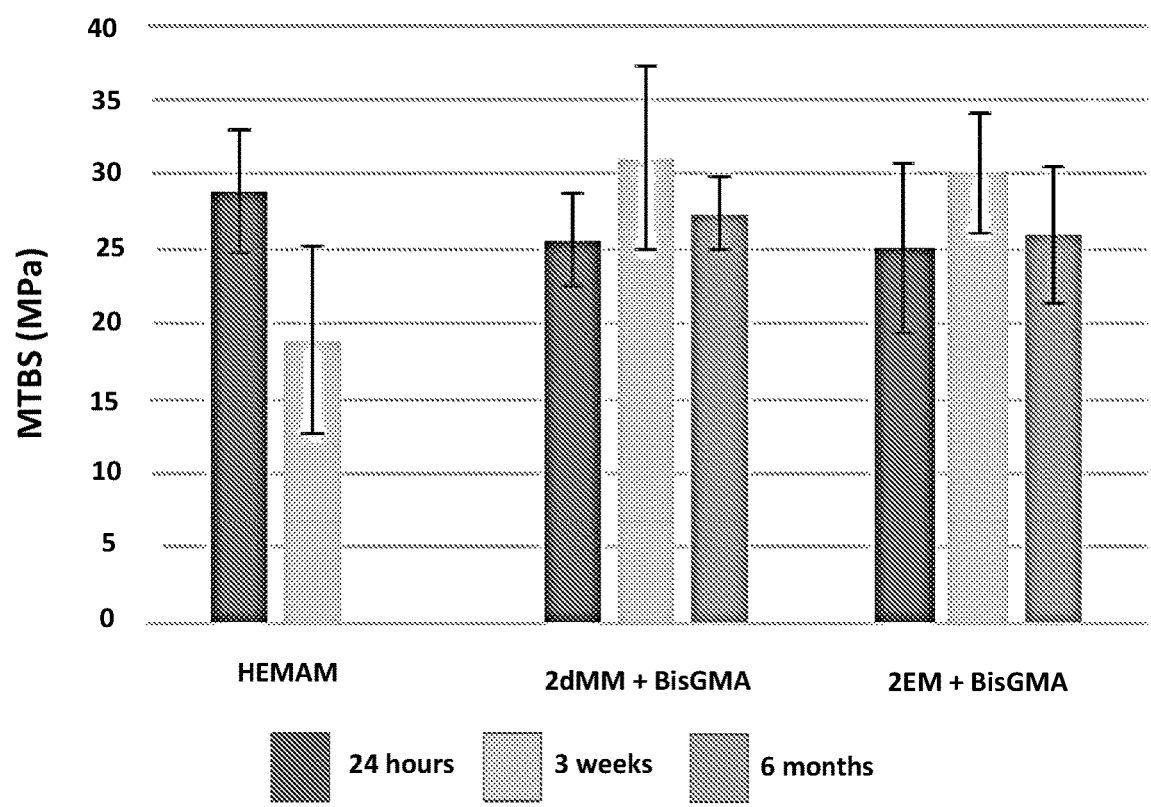
Figure 4A:
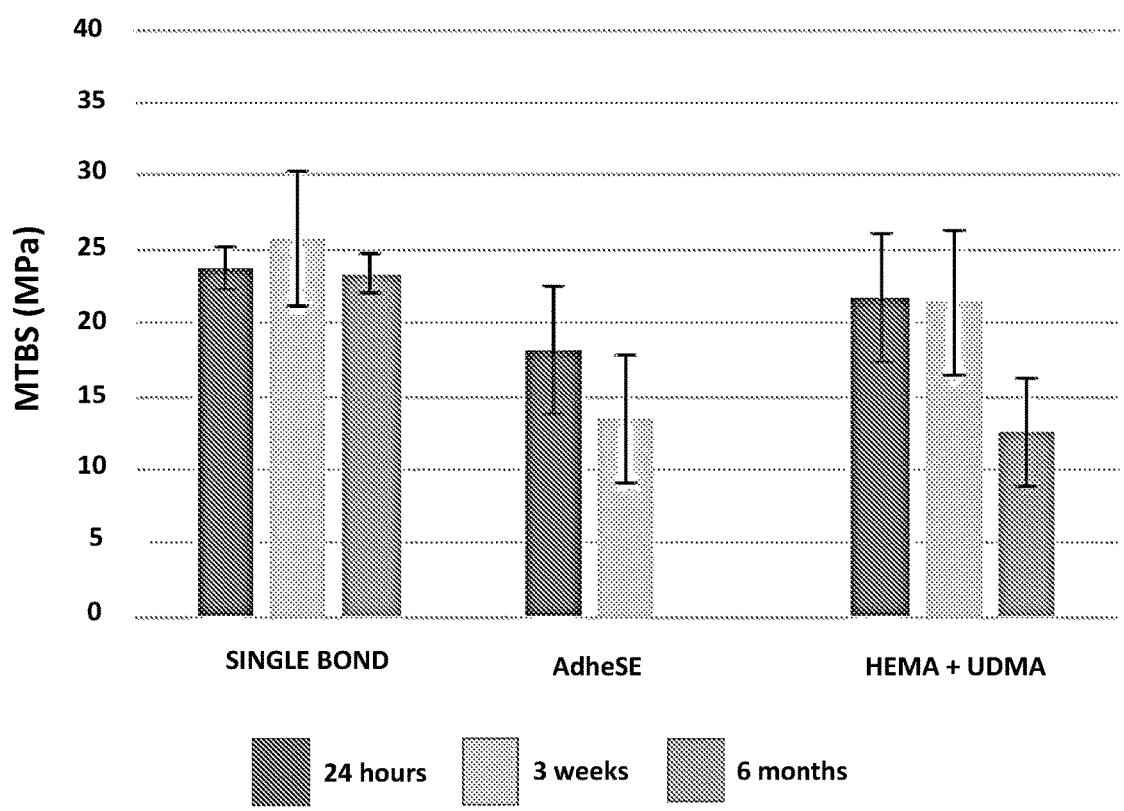
FIGS. 4A, 4B, 4C, and 4D depicts dentin microtensile bond strength (MPa) comparisons for adhesives and control groups after 24 hours, 3 weeks, and 6 months of water storage.
Figure 4B:
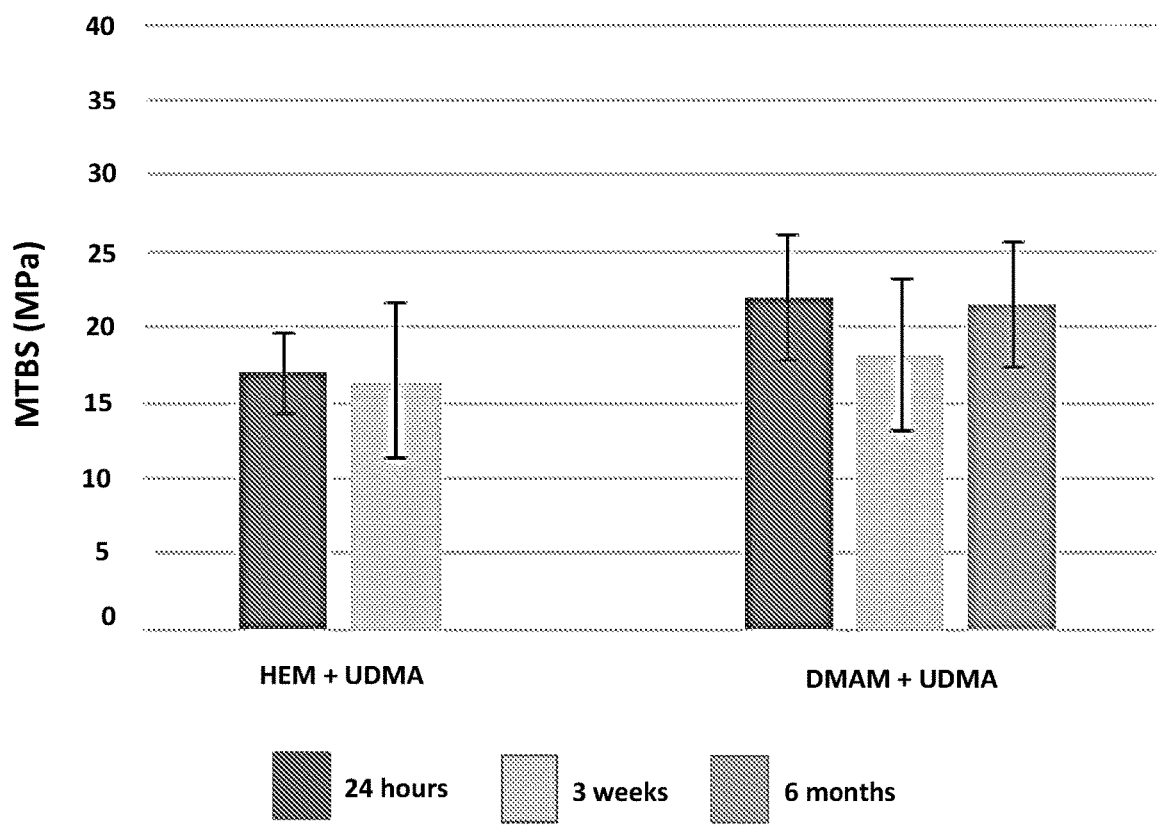
Figure 4C:
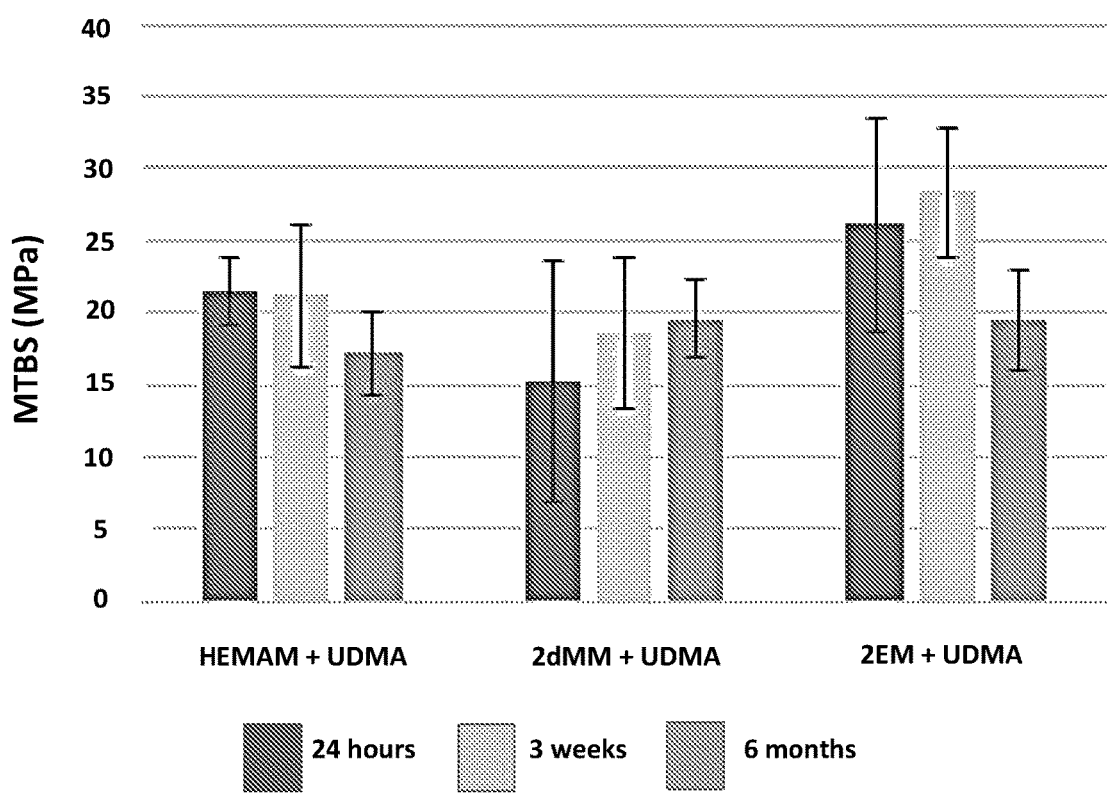
Figure 4D:
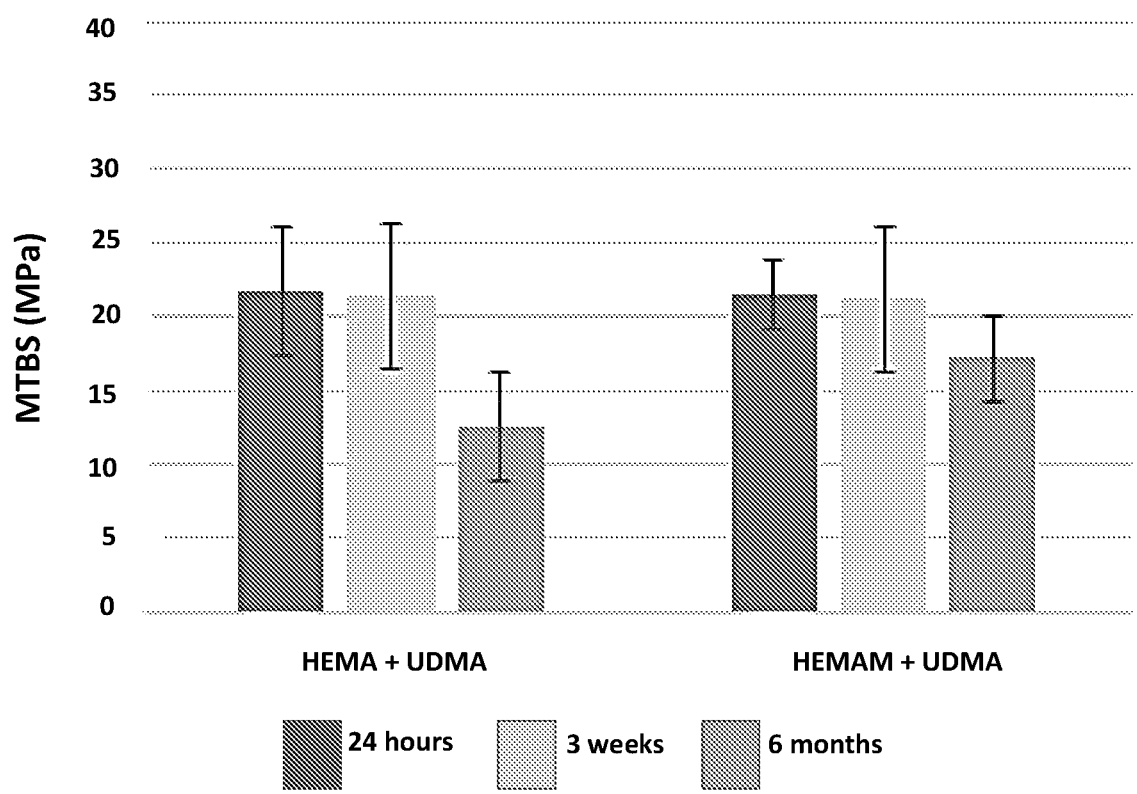

Kinetic curves for all experimental materials combined with BisGMA are presented in FIG. 1 and with UDMA in FIG. 2.

Referencing FIG. 1, polymerization rate (%.s$^{-1}$) as a function of conversion (%) for non-solvated adhesives was based on BisGMA. Vinyl conversion was followed in real-time as the materials were photocured with 630 mW/cm² for 300 seconds. (A) Meth- and acryl-secondary and tertiary amides are presented. (B) Comparison between the two tertiary acrylamides tested. (C) Comparison between secondary methacrylamides tested.

The highest polymerization rates are shown by the acrylate and the lowest by the tertiary methacrylamide. DMAM presented polymerization rate almost 4 times higher than HEM (31.3 versus 8.3%.sec$^{-1}$, respectively) and 13% higher final degree of conversion (Table 2). The alpha-substituted version 2dMM presented the highest polymerization rate (2 dMM=12.4, HEMAM=6.9, and 2EM=8.3%.sec$^{-1}$) (Table 2). The final degree of conversion was similar between them (73.7, 74.9, and 72.6%, respectively) (Table 2).

TABLE 2

Average (SD) of maximum rate of polymerization (Rp max) (% · s$^{-1}$) and degree of conversion at Rp$_{max}$ (DC at Rp$_{max}$) (%) for BisGMA and UDMA mixed at 60 wt % with the different mono-functional monomers tested. Values followed by the same upper case letter within the same column are statistically similar ($\alpha$ = 5%).

| | BisGMA | | UDMA | |
|---|---|---|---|---|
| Monomers | Rp$_{max}$ | DC at Rp$_{max}$ | Rp$_{max}$ | DC at Rp$_{max}$ |
| HEMA | 10.9 (0.6) C | 29.8 (1.9) CD | 17.1 (0.1) B | 44.7 (1.0) B |
| HEA | 14.2 (0.4) B | 43.8 (4.7) A | NA | NA |
| HEMAM | 6.9 (0.9) D | 26.1 (0.2) D | 16.9 (0.2) B | 22.7 (0.9) D |
| HEAM | 11.4 (0.4) C | 35.3 (0.9) BC | NA | NA |
| HEMMA | 1.9 (0.3) E | 19.0 (1.1) E | NA | NA |
| HEM | 8.3 (1.4) D | 29.6 (0.6) CD | 26.2 (0.5) A | 36.5 (2.3) C |
| DMAM | 31.3 (0.6) A | 39.1 (2.9) AB | 24.6 (2.0) A | 54.0 (0.9) A |
| 2dMM | 12.4 (0.6) BC | 14.5 (3.0) E | 15.9 (0.2) B | 18.6 (1.6) DE |
| 2EM | 6.8 (0.1) D | 18.5 (0.7) E | 14.7 (0.6) B | 16.5 (2.7) E |
| p | <0.001 | <0.001 | <0.001 | <0.001 |

Tertiary acrylamides showed similar polymerization rate and final degree of conversion (DMAM=24.6%.sec$^{-1}$ and 95.5%, and HEM=26.2%.sec$^{-1}$ and 93.2%, respectively) (Tables 2 and 3). DMAM presented a shoulder at the beginning of the curve. Secondary methacrylamides HEMAM, 2dMM, and 2EM showed similar polymerization rate and final degree of conversion (16.9 and 84.0, 15.9 and 80.1, and 14.7%.sec$^{-1}$ and 84.1%, respectively) (Table 2). Methacrylate and methacrylamide showed similar polymerization rate (17.1 and 16.9%.sec$^{-1}$, respectively) (Table 2) but HEMA obtained higher final degree of conversion than HEMAM (90.3% versus 84.0%, respectively) (Table 2). HEMA showed higher onset of vitrification and a shoulder at the beginning of the curve.

Referencing FIG. 2, polymerization rate (%.s$^{-1}$) as a function of conversion (%) for non-solvated adhesives based on UDMA. Vinyl conversion was followed in real time as the materials were photocured with 630 mW/cm$^2$ for 300 seconds. (A) Tertiary acrylamides. (B) Secondary methacrylamides HEMAM, 2dMM and 2EM. (C) HEMA and HEMMAM (methacrylate and tertiary methacrylamide). Tertiary acrylamides showed similar polymerization rate and final degree of conversion (DMAM=23.0%.sec$^{-1}$ and 95.5%, and HEM=25.0%.sec$^{-1}$ and 93.2%, respectively). DMAM presented a shoulder at the beginning of the curve. Secondary methacrylamides HEMAM, 2dMM and 2EM showed similar polymerization rate and final degree of conversion (17.0 and 84.0, 15.0 and 80.1, and 14.0%.sec$^{-1}$ and 84.1%, respectively). Methacrylate and methacrylamide showed similar polymerization rate (17.0 and 16.0%.sec$^{-1}$, respectively) but HEMA obtained higher final degree of conversion than HEMAM (90.3% versus 84.0%, respectively). Also, HEMA showed higher onset of vitrification and a shoulder at the beginning of the curve.

Most current commercially available adhesives systems are based on ester-containing methacrylate products, which makes the material more susceptible to hydrolysis and enzymatic degradation (Finer & Santerre, 2003). The adhesive layer is in contact with dentin fluid via transudation (Prati et al. 2005), constantly risking the degradation of ester bonds into carboxylic acid and alcohol molecules. In addition, dentin enzymes are known to be activated after acid etching, with some evidence of deleterious effects not only to the collagen substrate but also to the adhesive material (REF). Finally, esterases found in saliva can also contribute to the degradation of the adhesive layer at the margins in contact with the oral cavity (Finer, Jourenal of Biomaterials Science, Polymer Ed. 14(8):837-849). This process translates into bond strength reduction over time (Hashimoto et al. J Dent Res 2000, vol 70-pages 1385-91) and/or restoration debonding, as well as secondary decay. Considering that (meth)acrylamides are hydrolytically stable and more resistant to enzymatic degradation (Xu et al. Polymer Science 2007, vol 45—pages 99-110), the use of such monomers for adhesive applications has the potential to overcome some of these issues.

Figure 9:
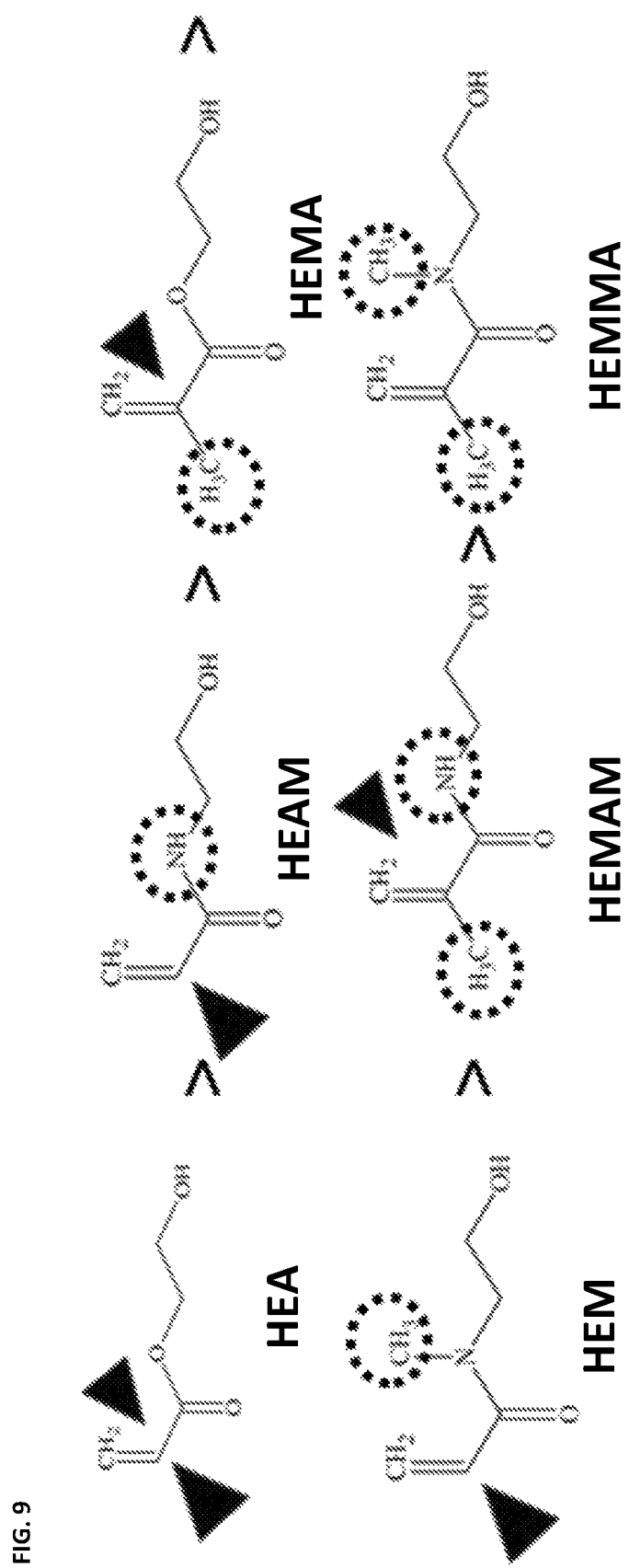
FIG. 9 provides a schematic representation of steric hindrance for six methacrylamides herein.

The monomers included in this study aimed at systematically evaluating the effect of steric hindrance on kinetics of polymerization and final conversion, as well as on the monomer's resistance to enzymatic degradation. Steric hindrance is defined as a physical impediment imposed by the chemical structure, which in this case, offered a progressively more challenging scenario for free radical generation on the vinyl group site (The Elements of Organic Chemistry—Gamini Gunawardena). Considering their molecular structure, we hypothesized that the reactivity of the tested monomers would increase in the same order as their steric hindrance: acrylate>secondary acrylamide>methacrylate>tertiary acrylamide>secondary methacrylamide>tertiary methacrylamide (FIG. 9). This order assumes that monomers with no bulky substitutions, such as methyl groups, and/or hydrogen bonding potential in the vicinity of the vinyl would be more reactive. The polymerization kinetics profiles showing the co-polymerization of these mono-functional monomers with BisGMA followed the same order of this hypothesis. In a simplified analysis, disregarding the initial viscosity of the mixtures, as well as the likelihood for co-polymerization between monomers with different radical-labile functionalities, these results suggest that steric hindrance played a major role in kinetics. Briefly, atoms and bonds next to the vinyl groups represent a physical impediment for free radicals to reach and convert double in single bonds. Therefore, monomers with easier vinyl groups access show higher maximum polymerization rate and higher final degree of conversion. On the other hand, monomers with methyl groups and hydrogens bonds next to vinyl groups would present slower reaction and lower final degree of conversion. Additionally, methacryl-versions presented lower reactivity than their analogous acryl versions (HEMA×HEA, HEMAM×HEAM, HEMMA×HEM). Likewise, this may be explained by the limitation on the degree of freedom imposed by methyl groups, which makes the monomer more stable thermally and photochemically, and consequently less reactive (Ref).

These same spatial limitations can be speculated to be responsible for the monomers greater resistance to hydrolytic and enzymatic attack and, therefore, for these monomers to be useful in the dental application, a balance must exist between their reactivity and susceptibility to degradation. FIG. 9 provides a schematic representation of the decreasing accessibility of the vinyl due to steric hindrance progression. All monofunctional monomers used in the study are depicted: a methacrylate (HEMA), acrylate (HEA), secondary acrylamide (HEAM) and methacrylamide (HEMAM), and tertiary acrylamide (HEM) and methacrylamide (HEMMA). Arrows indicate sites for easier radical access, while dashed circles representing steric impediments to radical access.

Even though the results for the kinetic profiles seems to indicate that the steric hindrance is an important aspect, other factors influencing the likelihood for co-polymerization of monomers with different functional groups also needs to be considered, as already mentioned. For example, there is evidence in the literature that the co-polymerization of methacrylates and acrylates can be challenging due to electronic rather than steric effects (Anseth et al. 1994). The same way, difficulties in co-polymerizations of methacrylates and methacrylamides can be envisioned (Kazyuka et al 2007). In the case of the present study, even though this does not rule out the possibility of IPN (interpenetrating polymer network) formation, the high levels of degree of conversion serve as strong indication of co-polymerization for HEMA (as expected), HEA, and other experimental monomers, but not for HEMMAM. Near-IR spectra were generated for each of one representative specimen for each co-polymerization tested, methacrylate (HEMA), acrylate (HEA), secondary acrylamide (HEAM) and methacrylamide (HEMAM), and tertiary acrylamide (HEM) and methacrylamide (HEMMA), at several stages of conversion. For acrylate, secondary and tertiary acrylamides, the vinyl peaks overlap that of BisGMA at (6165 cm$^{-1}$). In contrast, for the tertiary methacrylamide, a second, convoluted peak at 6135 cm$^{-1}$ is identified, and for the secondary methacrylamide, a shoulder at approximately the same region is identified. At least for the tertiary methacrylamide, this allows for the precise calculation of each vinyl's conversion, and from this calculation, it is apparent that the reactivity of the tertiary methacrylamide is minimal, which in turn explains the low degree of conversion obtained for this group, attributed mostly to the conversion of BisGMA. In this case, the low viscosity of the tertiary methacrylamide monomer allowed for relatively high conversion of the BisGMA monomer.

When comparing monomers with the same polymerizable functionality, such as HEM and DMAM—both tertiary acrylamides, different polymerization kinetics profiles are observed for the co-polymerizations with BisGMA. DMAM showed polymerization rate almost 4 times greater than HEM (31.2 versus 8.3%.sec$^{-1}$, respectively), as well as higher degree of conversion (90.2% versus 78.1%, respectively). This expressive difference can be explained by the much lower initial viscosity of DMAM (XXX Pa·s) compared to HEM (XXX Pa·s). BisGMA by itself is a very viscous monomer (1200 Pa·s), and does not reach conversions much higher than 30% in homopolymerizations due to early onset of diffusional limitations to propagation. The addition of lower viscosity diluents, such as TEGDMA, was demonstrated to increase BisGMA's conversion (REF: Peutzfeldt). In this study, the lower viscosity of DMAM contributed to delaying diffusional limitations (and the onset of autoacceleration/deceleration) to higher degrees of conversion, which increased both the maximum rate of reaction, but also the final conversion in relation to the more viscous HEM mixtures In terms of the co-polymerizations with UDMA, DMAM and HEM in general presented similar polymerization rates (24.6 and 26.1%.sec$^{-1}$, respectively) and final degrees of conversion (95.5% and 92.6%, respectively). This is likely due to the fact that the initial viscosity for UDMA is much lower than for BisGMA (1369 versus 28 Pa·s at 30° C. and 1 Hz) (Manufacturer's literature—Dickens S H, et al. Polymerization kinetics of methacrylate dental resins. Macromolecule, 2003), due to the weaker hydrogen bonding interaction provided by the urethane groups in comparison to the hydroxyl groups present in BisGMA (Singh, S. et al., Trans Faraday Soc, 1966, 62, 1056). In that case, the change in the base monomer's viscosity was not as marked, so the monofunctional diluent did not influence the onset of diffusional limitations to propagations (Dickens, 2003). It is also noteworthy that UDMA is more reactive than BisGMA to begin with, which relates to the presence of carbamates in its backbone, in turn making this monomer better able to produce higher polymerization rate and degree of conversion (Dickens, 2003).

However, even though the maximum rates of polymerization were similar for HEM and DMAM in co-polymerizations with UDMA, their kinetic profiles were markedly different. In the rate of polymerization as a function of conversion plot it is possible to identify a two-stage kinetic profile when DMAM is used. In fact, this was also the case in the co-polymerization of DMAM with BisGMA and HEMA with UDMA. This type of kinetic profile, though not conclusive, points to the formation of distinct phases in the material, and has been correlated with the formation of interpenetrating polymer networks (IPNs). IPNs, by definition, are constituted by two or more chemically distinct polymer networks held together by mutual entanglements (Sperling, 1995—Ref 13 Artigo 1 IPN). They can be formed when there is differential reactivity of two monomers, which does not favor co-polymerization, as has been demonstrated for methacrylates and acrylates. Since the reactivity of DMAM/HEMA (and monofunctional monomers in general) is very low in homopolymerizations, it can be speculated that the first stage in the kinetic profile corresponds to the faster polymerization of UDMA/BisGMA-rich phases, followed by the polymerization of DMAM/HEMA-rich phases. Moreover, when comparing the DMAM co-polymerizations with UDMA or BisGMA, the rates are much lower for the former. As mentioned before, this is likely related to the fact that the change in initial viscosity for BisGMA is much more dramatic than for UDMA. This led to much faster autoacceleration for BisGMA, which reached RPmax at lower conversion than UDMA and showed much faster deceleration as well. In other words, even though the presence of DMAM was able to more significantly affect the co-polymerization with BisGMA, the delay in the onset of diffusional limitations in relation to conversion is still much greater for UDMA, probably owing to its greater flexibility, lower Tg and weaker intermolecular interactions (Dean, 2001—Macromolecules, Dickens 2013), and that monomer pair ultimately reached higher conversion.

In relation to the secondary methacrylamides with different alpha-carbon substitutions, 2dMM showed polymerization rate almost twice as high as HEMAM (no substitution on the alpha carbon) and 2EM (12.3, 7.4, and 6.7%.sec$^{-1}$ respectively), although the final degrees of conversion were very similar, at 73.7, 75.9, and 72.6% respectively (FIG. 1C). This was somehow unexpected based on the fact that the presence of two bulky groups in 2dMM had been hypothesized to present greater challenge in terms of steric hindrance compared to the somewhat more flexible ethyl group in 2EM. These results seem to indicate that having the methyl groups one carbon away from the vinyl provides enough separation, and may actually further expose the double bond. The fact that the ethyl group provides no effect in the polymerization rate compared to the non-substituted HEMAM adds evidence to this argument. In addition, the higher polymerization rate of 2dMM in comparison to the other secondary methacrylamides may be due to the fact that its log P value is much similar to BisGMA's (log P: 2dMM=0.33, 2EM=0.60, HEMAM=−0.21, Bis-GMA=5.09). It can be speculated that this improves miscibility and facilitates co-polymerization.

Figure 10:
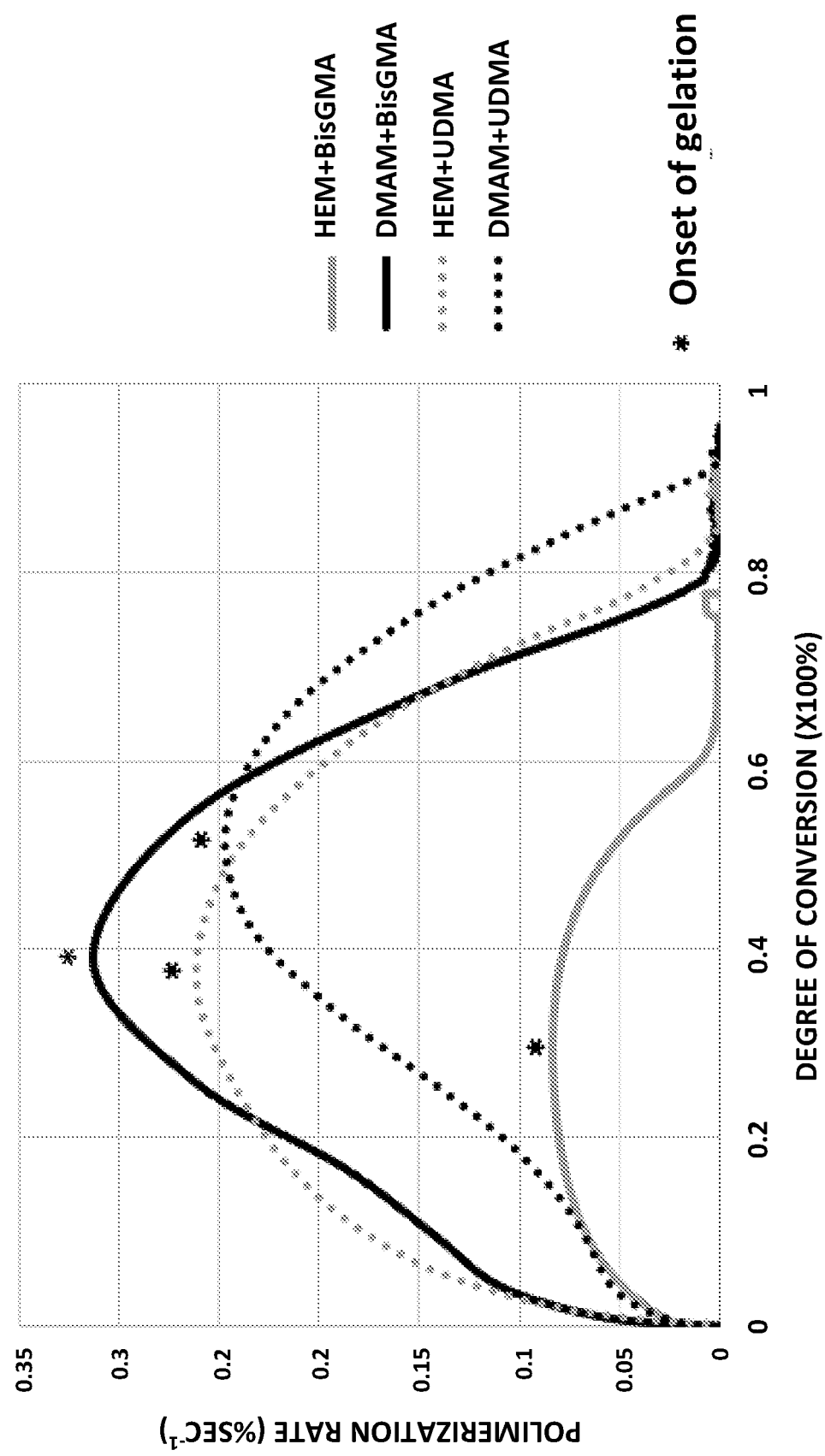
FIG. 10 represents polymerization rates for combinations of HEM and DMAM with BisGMA and UDM.

In general, the association between the secondary methacrylamides (HEMAM, 2dMM and 2EM) with UDMA led to more reactive mixtures than with BisGMA. Comparing the kinetics results, the final degree of conversion increased between 8 and 14%, and the polymerization rate increased by more than two-fold for HEMAM and 2EM, and 25% for 2dMM when combined with UDMA (FIG. 10). This was expected due to the difference of reactivity between UDMA and BisGMA (Dickens, 2003), as discussed above. Another interesting aspect is that the UDMA combinations followed exactly the same trend indicated by the steric hindrance, with HEMAM being slightly more reactive than 2EM and 2dMM. However, in BisGMA mixtures the hydrophobicity seems to have played a more crucial role than the steric hindrance When HEMA was combined with UDMA, a shoulder is observed in the polymerization kinetics curve, which was not the case for the BisGMA combination. It can be speculated that the shoulder is related to phase-separation or IPN formation (as discussed above) it is important to consider the determinant aspects involved on it. As the polymerization proceeds, the polymeric chains increase and hence the molecular weight of the IPN components, decreasing the entropy of mixing and reducing the miscibility (Dean and Cook, 2002—Artigo 2 IPN, Referencias 9 e 10 desse mesmo artigo). Therefore, the degree of mixing is controlled by the balance between kinetics and thermodynamics of cure because large-scale macro-molecular diffusion and subsequent phase-separation cannot occur after gelation (Dean and Cook, 2002 and Chen and Cook, 2008). If sufficient cross-linking of the components in the IPN occurs before diffusion of the components can occur, phase-separation will be prevented and high degree of mixing will be obtained. (Dean and Cook, 2002). Thus, the absence of phase-separation in HEMA+BisGMA combination may be due to the presence of higher amount of hydrogen bonding in BisGMA increasing the compatibility of the compounds and the miscibility between them (Lin and Chang, 1992).

Another hypothesis for this shoulder might be the formation of polymerization-induced phase separation (PIPS). In general, phase separation results of the increasing size of the growing polymer molecules. PIPS are characterized by gelation at low conversion and it may well precede phase separation (Serbutoviez C, et al. Polymerization-Induced Phase Separation. 2. Morphology of Polymer-Dispersed Liquid Crystal Thin Film, 1996—Macromolecules and Boots, et al. Polymerization-Induced Phase Separation. 1. Conversion-Phase Diagrams, 1996—Macromolecules). When the reaction starts there is only one phase containing a network, and at phase separation, conventionally, the polymer network deswells and a new phase containing only monomer appears (Boots et al, 1996). However, is some cases two phases, both containing polymer (as in our situation) may coexist and the polymerization rate will be different (Boots et al, 1996), explaining the shoulder presented on the kinetics curve. In free-radical cross-linking polymerization the initiation rate is low and the gel point is far below 1% conversion, even though of microgel particles formation tending to raise the gel point. One may increase the gel point by increasing the concentration of mono and divinyl monomers, by polymerization system diluting, by transfer agents addition, or by initiation rate increase (Boots et al, 1996).

It may happen because the reactivity difference between the monomers involved into the mixture does that one of them reacts faster, and highly internally cross-linked and loosely connected microgel particles are formed (Boots et al, 1996). Microgel can entrap pendant double bonds, unreacted monomer, and even radicals. Pendant double bonds, particularly those in the microgel regions, have reduced reactivity causing a delay in the gel point (Dickens, 2003). Considering that, especially for HEMA combined to UDMA it is possible to assume there is microgel particles formation associated to PIPS.

In relation to microtensile bond strength results, after 3 weeks almost all materials showed lower results than 24 hours, exception only for tertiary acrylamide which presented very stable behavior and numeric results comparable to tested commercial materials (FIG. 3). It may be associated to the great copolymerization between this acrylamide and BisGMA and low water sorption and solubility results (FIG. 2). Great polymerization is responsible for homogeneous polymer network, which makes water penetration and unreacted monomers leaching more difficult. Additionally, acrylates do not have ester groups making the compound more water degradation resistant and, consequently, microtensile bond strength more stable. On the other hand, tertiary methacrylamide showed the lowest microtensile bond strength results (FIG. 3). Assuming that there was no copolymerization between it and BisGMA, a heterogeneous polymer network is formed due to density differences. Heterogeneous polymeric network is associated to higher free space to accommodate water and easier leaching of unreacted monomers, which is in agreement to the highest water sorption and solubility showed by this group. In this case, even methacrylamides being ester-free the non-copolymerization was crucial for the poor microtensile bond strength performance.

Other groups showed intermediary water sorption and solubility results. The different performances between them may be associated to log P, which is partition coefficient and describes the solubility of the compound in an octanol-water solution. Therefore, higher log P is associated to higher hydrophobicity. Additionally, comparing acryl and methacryl versions, methyl groups increased the hydrophobicity which is expected because methyl groups have an apolar nature.

Additional Methods: Tertiary quaternary ammonium acrylamides (QAAM) and methacrylamides (QAMAM) with alkyl side chain lengths of 9 and 14 carbons (C9 and C14) were synthesized and incorporated at 10 wt % into experimental composites based on BisGMA:TEGDMA (1:1), camphorquinone/ethyl-4-dimethylaminobenzoate (0.2/0.8 wt %) and 70 wt % barium glass fillers. Analogous methacrylate versions (QAM) were used as controls. Degree of conversion (DC) and rate of polymerization (RP) during photoactivation (800 mW/cm2) were followed in real-time with near-IR. Flexural Strength (FS) and Modulus (E) were measured on 2×2×5 mm bars in 3-point bending after 24 h dry storage and 7-day storage in water at 37° C. Antimicrobial and antifouling properties were evaluated by bioluminescence (Luciferase Assay) and biofilm removal by water spray impingement test, respectively. Data were analyzed with one-way ANOVA/Tukey's test ($\alpha$=0.05).

Results: DC was similar for all groups tested. Both QAMAMs and C14QAAM presented significantly lower RP (Table 1). Under dry conditions, FS and E were similar for all groups. After water storage, all materials presented FS/E similar to the control, except for C14QAAM (for FS) and C14QAMAM (for E), which were lower. All C14 versions were strongly antibacterial, decreasing the titer counts of biofilm by more than two orders of magnitude in comparison to the control, which made it impossible to subject them to the impingement test. C9 monomers did not present significant antibacterial nor antifouling properties.

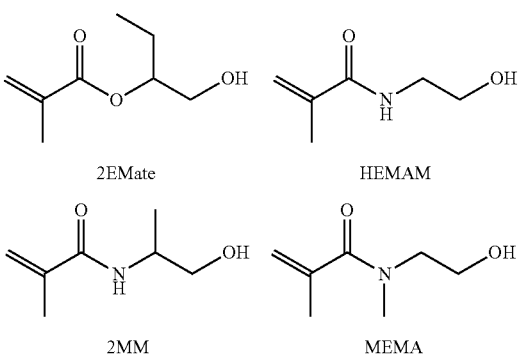

2EMate     HEMAM

2MM     MEMA

TABLE 1

Final degree of conversion, polymerization rate, mechanical properties and biofilm viability/attachment results for all varitions of quaternary ammonium monomers tested. Values followed by the same uppercase letter on the same column are statistically similar ($\alpha$ = 5%).

| Group | DC (%) | RP (% .s$^{-1}$) | FS (MPa) Dry | FS (MPa) Wet | E (GPa) Dry | E (GPa) Wet | Luciferase (ULR) | Biofilm Area Surface Removed (%) |
|---|---|---|---|---|---|---|---|---|
| Exp Control | 70.6 (0.3)A | 6.5 (0.14)B | 121.4 (11.9)A | 91.2 (18.7)AB | 9.4 (0.7)A | 6.7 (0.3)ABC | 3.06E+07 (6.28E+06)AB | 16.88 (3.74) B |
| C9QAM | 69.0 (0.3)B | 6.9 (0.08)A | 115.3 (15.6)A | 107.3 (21.4)A | 8.8 (1.1)A | 7.7 (1.2)A | 3.50E+07 (6.25e+06)A | 25.07 (7.14) A |
| C9QAAM | 68.9 (0.6)B | 6.2 (0.10)B | 109.8 (20.0)A | 76.1 (8.3)BC | 8.7 (0.8)A | 6.4 (0.1)BCD | 2.32E+07 (2.94E+06)B | 23.13 (3.52) AB |
| C9QAMAM | 69.8 (0.3)AB | 5.5 (0.19)C | 116.3 (11.3)A | 71.92 (5.9)BC | 8.6 (0.8)A | 6.4 (0.4)BCD | 3.04E+07 (6.23E+06)AB | 18.45 (3.20) AB |
| C14QAM | 69.8 (0.3)AB | 6.3 (0.23)B | 115.2 (10.2)A | 90.8 (15.6)AB | 9.1 (0.3)A | 7.2 (0.7)AB | 8.79E+03 (4.10E+03)C | NA |
| C14QAAM | 70.1 (0.2)AB | 4.3 (0.06)D | 106.1 (11.7)A | 77.7 (9.3)BC | 8.3 (0.8)A | 5.3 (0.2)D | 1.08E+04 (8.91E+03)C | NA |
| C14QAMAM | 69.4 (0.5)B | 5.5 (0.04)C | 114.2 (6.55)A | 63.6 (5.4)C | 8.8 (1.1)A | 5.9 (0.5)CD | 2.69E+04 (1.45E+04)C | NA |

Traditional dental methacrylate and of-interest experimental methacrylamide monomers were incubated in Millipore water and with cholinesterase (CE) and pseudocholinesterase (PCE), and matrix metalloproteinase 2 (MMP-2) enzymes and evaluated for potential use in dental composite materials.

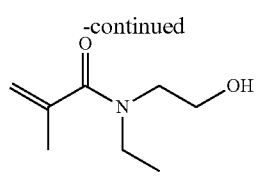

HEMA

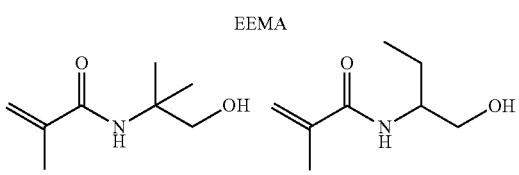

TEGDMA
Methacrylates

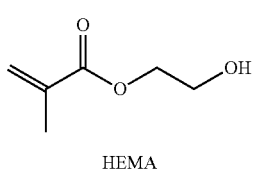

EEMA

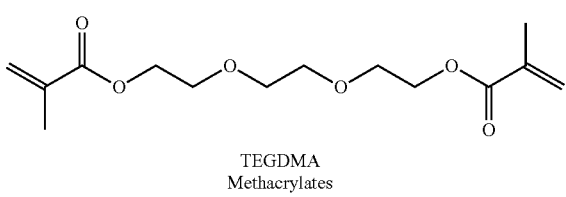

2dMM     2EM

2° Amides

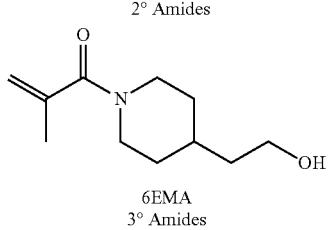

6EMA
3° Amides

Dental methacrylates and experimental methacrylamides were commercially obtained or synthesized in house.

Monomers were prepared to a concentration of 0.15 mM for water and CE/PCE incubations and incubated at 72 hours at 37° C.

Degradation from CE and PCE was monitored via high performance liquid chromatography (HPLC) and measured via initial and post incubation monomer area difference.

MMP-2 incubation was prepared at 0.02 mM monomer concentration and incubated at 24 hours at 37° C. and degradation from MMP was measured via a fluorometric assay utilizing a plate reader.

CE and PCE are enzymes found in saliva are responsible for breaking down ester functional groups. The methacrylate monomers demonstrate higher amounts of degradation compared to methacrylamides in both hydrolytic and enzymatic environments. This was calculated in the decrease in absorbance area measured by HPLC at 227 nm wavelength. Degradation was further verified by the detection of methacrylic acid.

Enzymatic degradation paralleled trends observed in water. Methacrylate monomers express greater degradation compared to methacrylamides. Bulkier substitutions generally exhibit less degradation. MMP-2 is a gelatinase enzyme that contributes to the breakdown of collagen in dentin. The breakdown of collagen can result in weaker bond strength of dental adhesives and ultimately lead to restoration failure. BB94 is a commercial, known inhibitor of MMP-2. Plate reader fluorescence was set at Ex/Em=490/525 nm. Lower fluorescence signal indicates enzyme inhibition. Initial study indicate HEMA and HEMAM inhibition of MMP-2. However, substituted monomers demonstrate no inhibition of the gelatinase.

Additional Work

Formulation of Experimental Adhesives

Experimental adhesive resins were formulated with 60 wt % BisGMA (Bisphenol A glycidyl dimethacrylate) or UDMA (urethane dimethacrylate) purchased from ESSTECH (Essington, Pa., USA), and 40 wt % of one of the monofunctional monomers listed in Table 1 (synthetic procedures and characterization of the monomers, including 1H-NMR spectra and log P calculations obtained with Chem Draw software). In all formulations, the photoinitiator system was composed of 0.2 wt % of the alpha-cleavage type, single component DMPA (2,2-dimethoxy-2-phenylacetophenone) and 0.4 wt % DPI-PF6 (diphenyliodonium hexafluorophosphate). This initiator composition was determined in a pilot study as providing the best compromise between adequate reactivity and high final conversion for the monomers tested. 0.1 wt % Butylated hydroxytoluene (BHT) was added to each formulation as an inhibitor for shelf life. 40 vol % ethanol was added only for the materials to be used for microtensile bond strength tests.

Polymerization Kinetics

Disk samples (10 mm diameter, 0.8 mm thick) sandwiched between glass slides were placed in the chamber of an infra-red spectrometer (Nicolet 6700, ThermoScientific, USA) and irradiated with a mercury arc lamp (Acticure, EXFO Acticure 4000 UV Cure; Mississauga, Canada) filtered to 320-500 nm for 300 s, delivering 630 mW/cm2 directly to the specimen. Spectra were collected in real-time during photoactivation, with 2 scans per spectrum at 4 cm−1 resolution. The degree of conversion was calculated based on the area of the vinyl overtone in near-IR at 6165 cm−1 for methacrylates and around 6130 cm−1 for (meth)acrylamides. Clear, distinct separation of the peaks was only possible for one group (BisGMA-HEMMA), whereas in the other groups the peaks were more severely convoluted. For BisGMA-HEMMA, the conversion of each peak was calculated as previously described [22, 23]. The rate of polymerization was calculated as the first derivative of the conversion vs. time curve [24].

Water Sorption and Solubility

The same samples used in the polymerization kinetics were tested for water sorption and solubility, according to [25]. Briefly, the mass of the disks was determined before (m1) and after immersion in distilled water for one week (m2). The disks were then stored in a desiccator until the mass stabilized (m3), which took around one week. Water sorption (WS) and solubility (SL) were calculated using the following equations:

$$WS = \left(\frac{M2 - M3}{V}\right) \text{ and } SL = \left(\frac{M1 - M3}{V}\right)$$

where V is the volume of the specimen.

2.4 Microtensile bond strength

Recently extracted caries-free human third molars (n=6) had the cusps removed to expose a flat dentin surface. This study was approved by the Oregon Health & Science University IRB (#IRB00012056). The dentin surface was etched with 35% phosphoric acid (3M ESPE, St. Paul, Minn., USA) for 15 s, rinsed and blotted dry. The adhesive materials were applied in two consecutive coats, photoactivated for 20 s. For this test only, Adper Single Bond (3M-ESPE) was included as a commercial control. A block of composite (Filtek Supreme, A2, 3M-ESPE) was built in 2 increments with 2 mm thickness, photoactivated for 20 s each at 700 mW/cm2 (Demi Plus, Dentsply-Sirona, Milford, Del., USA). The tip of the light guide (8 mm in diameter) was positioned 1 mm away from the composite, and the irradiance was checked daily at the same distance using a clinical grade radiometer (Demetron LED radiometer, Kerr Co., Orange, Calif., USA). The restored teeth were stored for 24 h in distilled water, then sectioned to produce 1×1 mm2 sticks. The sticks were then stored for an additional 24 h or 3 weeks in distilled water at 37° C., and then tested in tension (0.5 mm/min) until failure to determine microtensile bond strength using a custom-made jig (Odeme equipamentos, Luzerna, S. C., Brazil) attached to a universal testing machine (Criterion, MTS, Eden Prairie, Minn., USA). Selected groups were also tested after storing the sticks for 6 months in distilled water at 37° C.

Mechanical Properties

The yield strength (YS) and elastic modulus (E) were analyzed using three-point bending, according to ISO 4049. Twelve rectangular bars (2.0×2.0×25.0 mm) per group were produced in silicone molds placed between two glass slides. Specimens were polymerized with a single exposure at 630 mW/cm2 using a mercury arc lamp filtered to 320-500 nm (Acticure). The tip of the light guide was positioned 7 cm away from the specimen, creating a spot size large enough to expose the entire bar in one shot, and eliminating heating concerns from the light source. Half of them were stored dry for 24 hours, and the other half for 7 days in 20 ml Milli-Q water. Specimens were tested at 0.5 mm/min cross-head speed, with 20 mm between supports. Elastic modulus (GPa) was calculated according to:

$$E = 3LD3$$

$$2wdh3$$

where L is the maximum load (N), D the span between the supports (mm), w the specimen width (mm), h the specimen height (mm), and d the deflection corresponding to L (mm). Yield strength values (MPa) were obtained for all materials for accurate comparisons of material strength before any plastic deformation occurred. This was achieved by applying a 0.2% offset from the initial elastic region on a stress-strain curve.

Monomer Degradation in Low pH Environment

Aqueous solutions with pH values 1, 2, 4, 5 and 7 were prepared using deuterium oxide (D2O, pH 9.8) and adjusted by adding deuterium chloride (20 w/w % in D2O). 1.2 mL of 60 mM solutions of each of the 9 tested monomers were prepared at 5 different pH values (n=3). The aqueous solutions were stored in capped NMR tubes at 37° C. for 30 days. The pH was measured weekly to ensure that the potential production of acidic by-products (methacrylic acid) did not lead to pH changes. A 45-pulse was used for NMR observation, with accumulation and repetition times of 1000 and 3.8 s, respectively. Detailed procedures and calculations are described in the appendix materials Statistical Analysis After normality and homocedasticiy tests, data were analyzed with one-way ANOVA and Tukey's test ($\alpha=0.05$).

Results

Figure 16A:
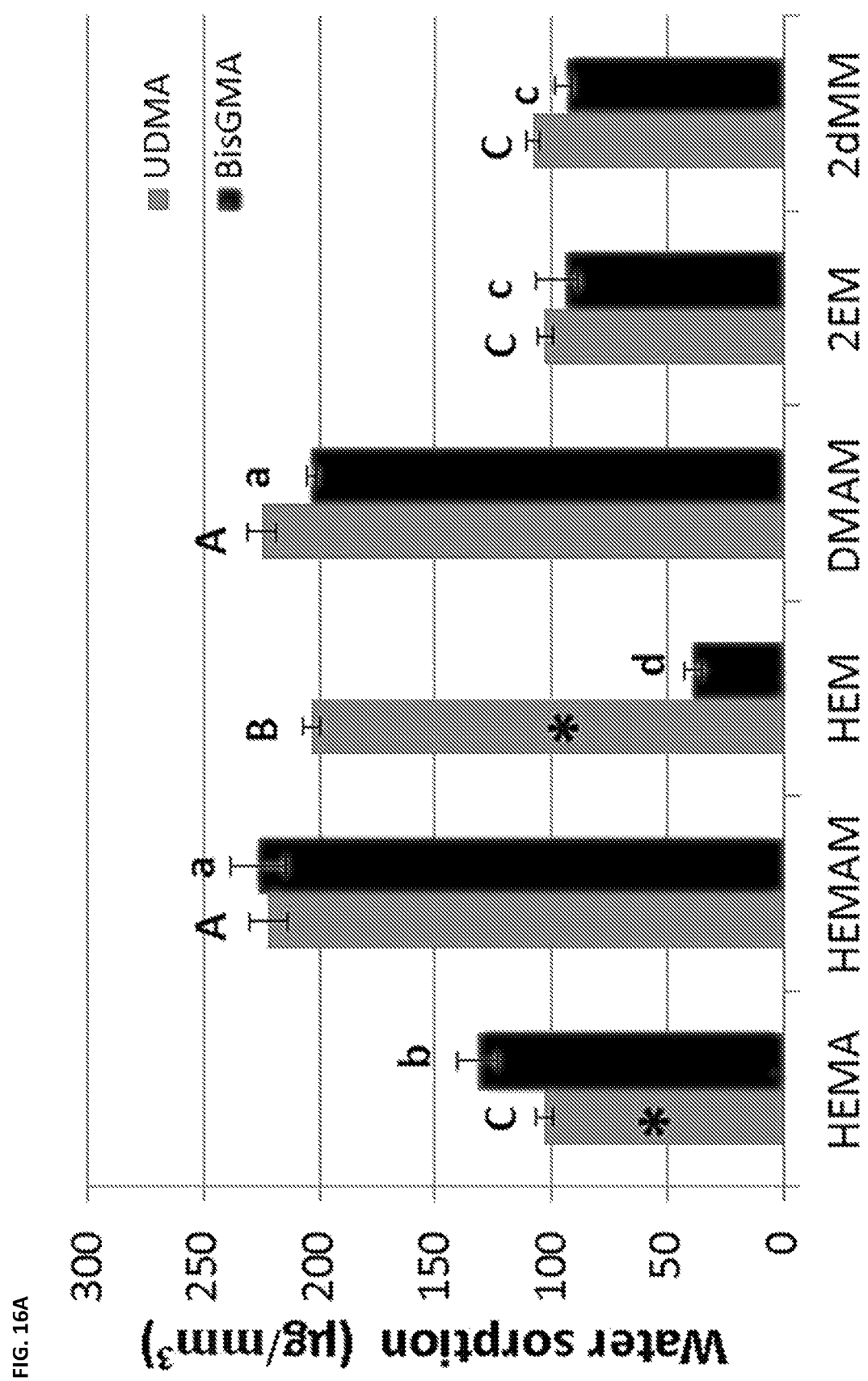
FIGS. 16A and B represent water sorption and solubility results obtained for all tested copolymerizations.
Figure 16B:
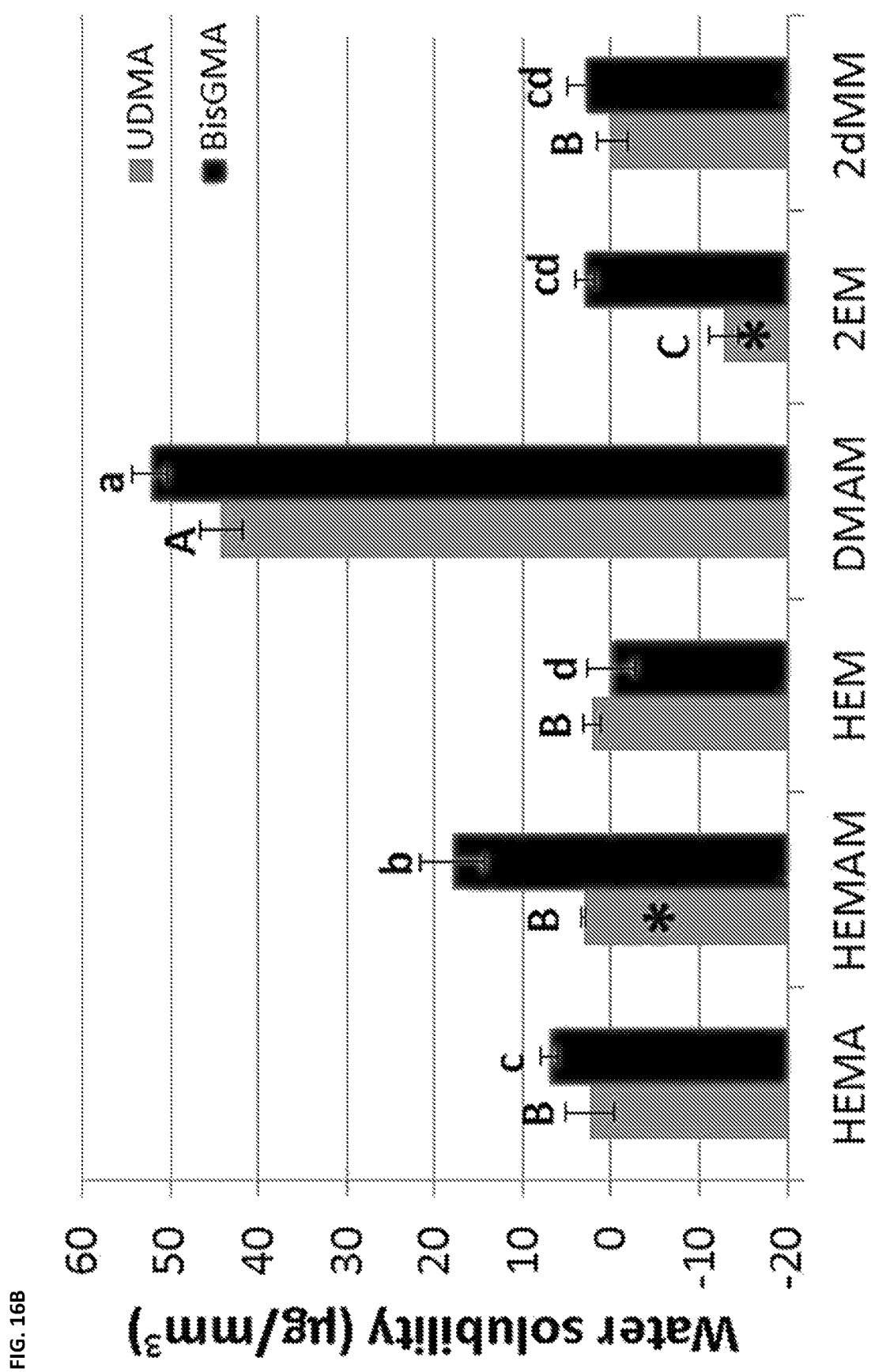

Polymerization kinetics (rate of polymerization as a function of conversion) for all experimental materials combined with BisGMA and with UDMA are presented in FIGS. 1A and 1B, respectively. Values of maximum rate of polymerization (RPmax), degree of conversion at the maximum rate/onset of deceleration (DC at RPmax, used to estimate the onset of vitrication) and the degree of conversion at 40 s (as an example of the conversion at clinically-relevant exposure times) are presented in Table 2. In general and as expected, the acryl versions of the monomers presented higher polymerization rates and conversions compared to the methacryl versions of the monomers. UDMA-containing mixtures also presented higher rates and conversion values compared to the BisGMA counterparts. Results for water sorption and solubility are shown in FIG. 16. For UDMA mixtures, in terms of water sorption, DMAM showed the highest results (224.7 µg/mm3), followed by HEM>HEMA=2dMM=2EM (203.5, 102.8, 102.7, and 102.7 µg/mm3, respectively). DMAM showed the highest solubility in both co-polymerizations (UDMA=44.3 and BisGMA 52.3 µg/mm3). The most solubility resistant monomers were HEMA, HEM and 2dMM. BisGMA co-polymerizations showed similar trend for water sorption results in comparison to UDMA mixtures (DMAM>HEMA>2EM=2dMM), except HEM that showed the lowest results (38.7 µg/mm3).

Figure 17A:
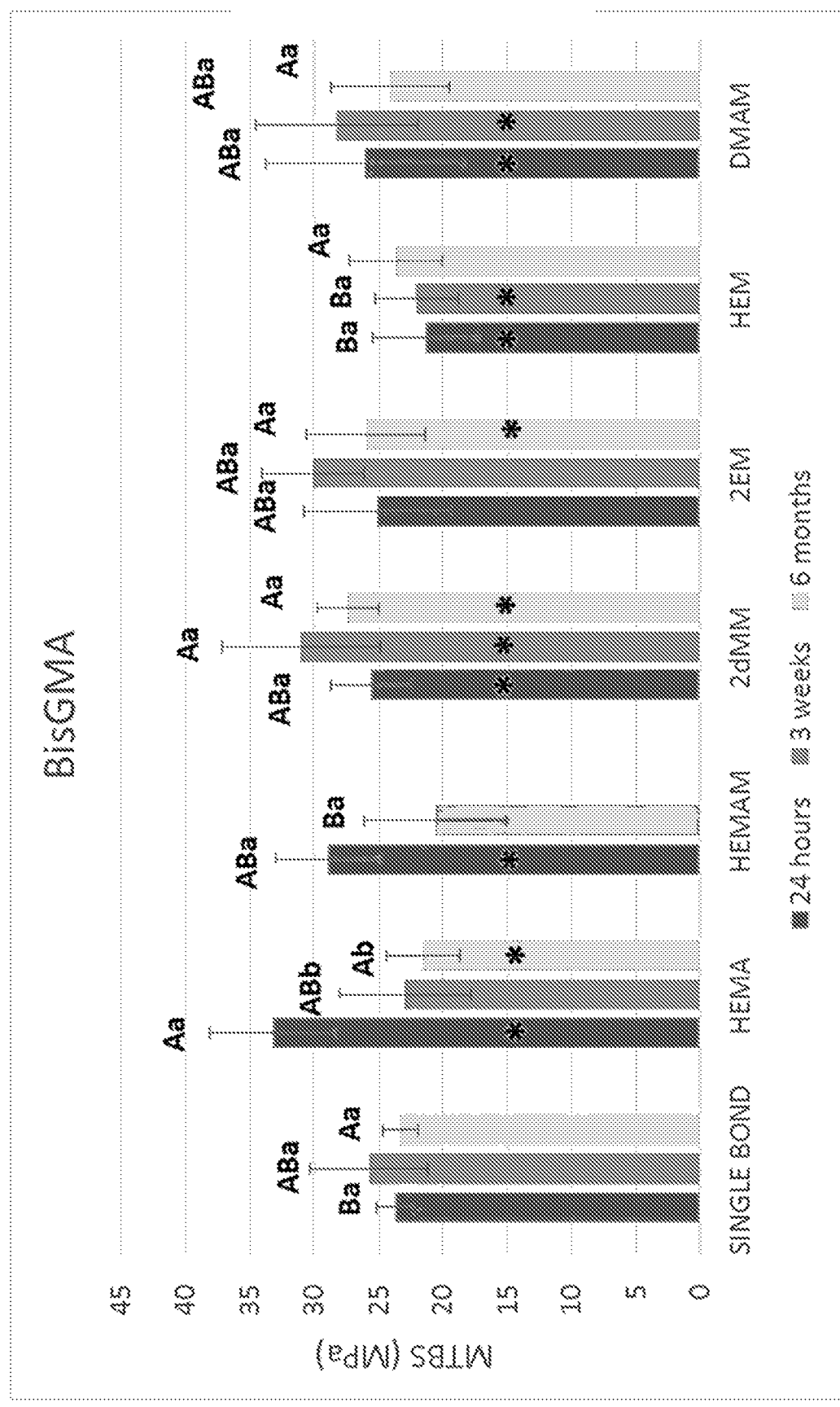
FIGS. 17A and B depict Dentin Microtensile Bond Strength for control groups and all mono-functional monomers copolymerized with BisGMA and UDMA.

Results for microtensile bond strength are shown in FIGS. 17A and B. Immediate µTBS results showed that highest values for BisGMA copolymerizations (HEMA=33.2, DMAM=26.0, 2dMM=25.6, and 2EM=25.1 MPa) (exception for HEM), and 2EM-U (26.0 MPa). After 3 weeks, DMAM-B, 2dMM-B, and 2EM-B showed the highest results (28.2, 31.0 and 30.0 MPa, respectively), and HEM-U, DMAM-U and 2dMM-U the lowest ones (16.5, 18.1, and 18.5 MPa, respectively). In 6 months, 2dMM-B presented the highest value (27.39 MPa) and HEMA-U the lowest one (12.5 MPa). In general, BiGMA mixtures had slightly better performance than UDMA copolymerizations. In terms of storage time, both methacrylate experimental controls showed significant bond strength reduction after 3 weeks (HEMA-B) or 6 months (HEMA-U). Among the methacrylamides and acrylamides, only 2EM-U presented some reduction over time (6 months); all other versions maintained constant bond strength, even after 6 months.

Results for mechanical properties are shown in Table 3. For UDMA mixtures, HEM, DMAM and 2dMM showed the highest yield strength results (125.5, 100.9, and 100.8 MPa, respectively). After 7 days water storage, 2EM and 2dMM showed the highest values (64.8 and 51.0 MPa, respectively), and HEM the lowest ones (11.84 MPa). The mechanical properties were reduced for all groups after water storage, with the least amount of reduction for 2EM (23.4%) and HEM being the most affected (reduction of 90.4%). For BisGMA mixtures, the highest values of dry yield strength were obtained when HEMA was used as the monofunctional monomer, statistically similar to all others, except for HEM, which showed roughly 50% lower YS compared to the HEMA group. After wet storage, this trend was maintained, with percent reductions in YS ranging from 51 (HEMA) to 64% (HEM). Except for HEMA formulations, there was no statistically significant difference between BisGMA and UDMA mixtures under dry storage ($p<0.001$). However, under wet conditions, in general, BisGMA mixtures showed higher results ($p<0.001$). In relation to the modulus, UDMA mixtures followed the same trend describe for the yield strength results for both storage conditions (Dry: DMAM (4.37) 2dMM (4.01) HEM (3.94) HEMA (3.46)=2EM (3.42)–Wet: 2dMM (2.50)=2EM (2.47) >HEMA (2.06)>DMAM (1.34)>HEM (0.48)). For BisGMA, the highest value for dry elastic modulus was obtained by BisGMA/HEMA mixtures, statistically greater than all other groups. The mixtures containing HEM presented statistically lower results than all other groups (except for 2dMM). All combinations were affected by the water storage ($p<0.001$).

TABLE 2

|  | BisGMA $Rp_{max}$ | BisGMA DC at $Rp_{max}$ | BisGMA DC at 40 s | UDMA $Rp_{max}$ | UDMA DC at $Rp_{max}$ | UDMA DC at 40 s |
| --- | --- | --- | --- | --- | --- | --- |
| HEMA | 10.9(0.6)B | 29.8(1.9)BC | 67.7(2.7)B | 17.1(0.1)B | 44.7(1.0)B | 75.3(1.2)B |
| HEMAM | 6.9(0.9)C | 26.1(0.2)C | 47.3(6.9)D | 16.9(0.2)B | 22.7(0.9)D | 65.4(1.5)C |
| HEM | 8.3(1.4)C | 29.6(0.6)BC | 60.3(0.7)C | 26.2(0.5)A | 36.5(2.3)C | 84.2(1.9)A |
| DMAM | 31.3(0.6)A | 39.1(2.9)A | 81.3(0.8)A | 24.6(2.0)A | 54.0(0.9)A | 91.0(1.5)A |
| 2dMM | 12.4(0.6)B | 14.5(3.0)D | 45.3(0.6)D | 15.9(0.2)B | 18.6(1.6)DE | 57.0(1.0)D |
| 2EM | 6.8(0.1)C | 18.5(0.7)D | 41.3(0.7)D | 14.7(0.6)B | 16.5(2.7)E | 58.4(1.6)CD |
| p | <0.001 | <0.001 | <0.001 | <0.001 | <0.001 | <0.001 |

TABLE 3

Yield Strength (MPa) and elastic modulus (E) for all tested co-polymerizations after 48 hours dry and 1 week wet storage. Different uppercase letters indicate statistically significant differences between the monofunctional monomers copolymerized with the same base monomer and under the same storage condition. Different lowercase letters indicate statistically significance differences BisGMA versus UDMA co-polymerizations. Asterisks indicate statistically significant differences within each material between the storage conditions (meaning all materials were statistically affected by water storage). Overall level of significance for statistical analysis: 95% (α <5%).

| Base | Monofunctional Monomer | Yield Strength (MPa) Dry | Yield Strength (MPa) Wet | Reduction (%) | Modulus (GPa) Dry | Modulus (GPa) Wet | Reduction (%) |
|---|---|---|---|---|---|---|---|
| BisGMA | HEMA | 155.2 (20.7)Aa* | 76.6 (7.3)An | 51 | 5.9 (0.2)Aa* | 2.8 (0.3)Aa | 53 |
|  | HEM | 77.1 (9.4)Bb* | 27.5 (4.3)Ca | 64 | 23 (0.3)Cb* | 1.7 (0.3)Aa | 26 |
|  | DMAM | 124.6 (19.8)ABa* | 51.2 (6.4)Ba | 59 | 4.6 (0.2)Ba* | 2.8 (0.4)Aa | 39 |
|  | 2EM | 100 9 (19.9)ABa* | 42.0 (3.7)BCa | 58 | 4.0 (0.5)Ba* | 2.58 (0.6)Aa | 35 |
|  | 2dMM | 109.4 (6.0)ABa* | 51.3 (5.2)Ba | 53 | 3.6 (0.2)BCa* | 2.22 (0.2)Aa | 38 |
| UDMA | HEMA | 85.3 (6.0)Bb* | 58.9 (8.0)Bb | 31 | 3.46 (0.3)Bb* | 106 (0.1)Bb | 40 |
|  | HEM | 123.5 (18.2)Aa* | 11.84 (2.37)Db | 91 | 3.94 (0.3)ABa* | 0.48 (0.01)Db | 87 |
|  | DMAM | 100.9 (15.2)ABa* | 31.8 (10.8)Cb | 69 | 4,37 (0.5)Aa* | 1.34 (0.2)Cb | 69 |
|  | 2EM | 84.6 (12.3)Ba* | 64.8 (8.5)Aa | 23 | 3.42 (0.2)Bb* | 2.47 (0.2)Aa | 28 |
|  | 2dMM | 100.8 (21.6)ABa* | 51.0 (6.0)Aa | 49 | 4.01 (0.2)ABa* | 2.50 (0.3)Aa | 38 |

Figure 18:
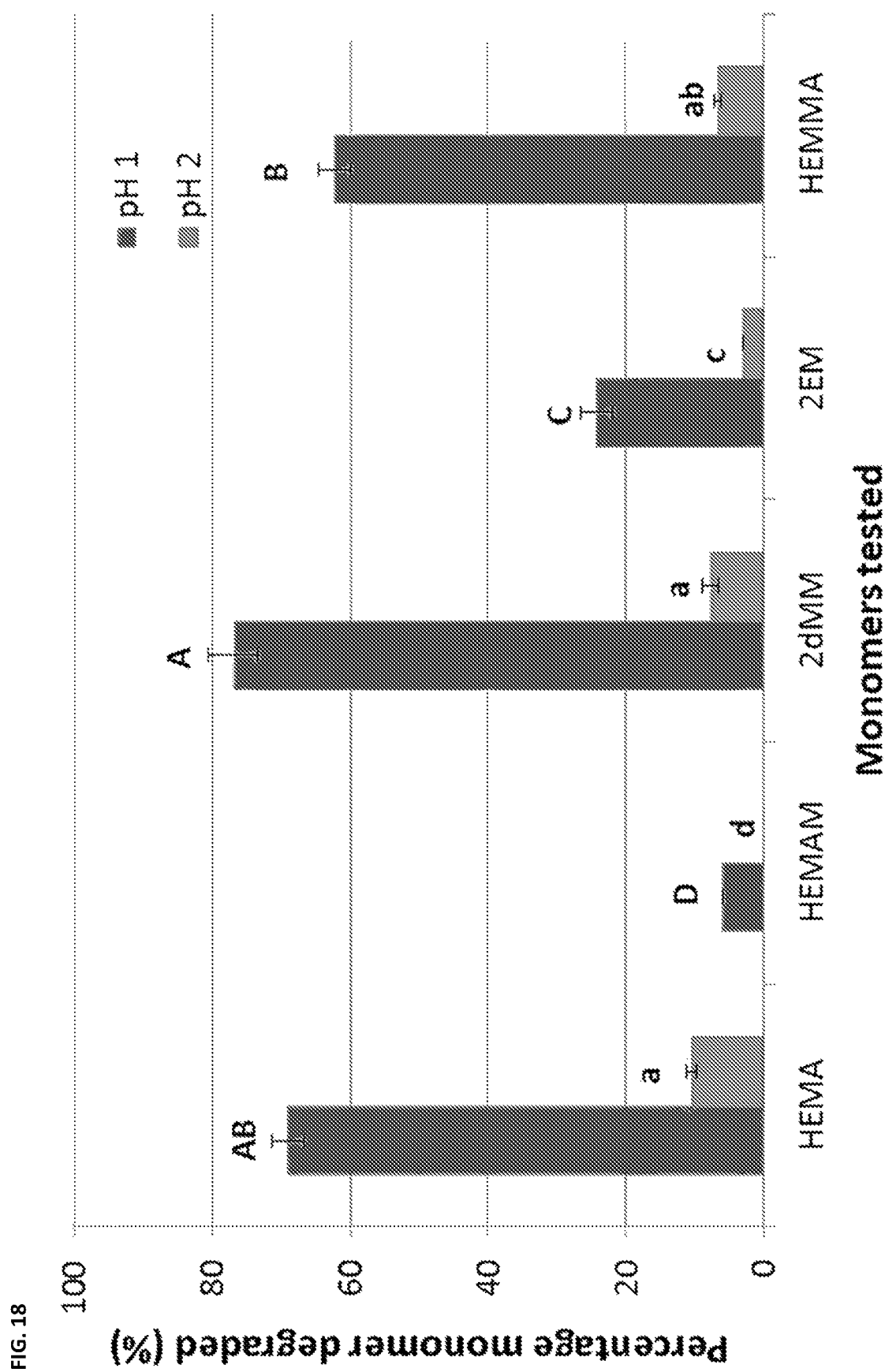
FIG. 18 represents percentage of remaining monomer following hydrolytic degradation at pH 1 and 2.

Neat monomer degradation results are shown in FIG. 18. No degradation was observed at pH 4, 5 or 7 after 30 days incubation for any of the monomers tested. At pH 1 and 2, the degree of degradation for each monomer increased with time. HEMAM showed one order of magnitude greater stability than HEMA at pH=1, with 6.0 (0)% degradation compared to 69.0 (2.3)% for HEMA. At pH 2, HEMAM did not show any significant amount of degradation products, compared to 10.5 (0.7)% degradation for HEMA. For the alpha substituted methacrylamides in relation to HEMAM, the degree of degradation of the monomers followed the order: HEMAM<2EM<2dMM. The tertiary methacrylamide presented degradation statistically similar to HEMA.

Discussion

Figure 15A:
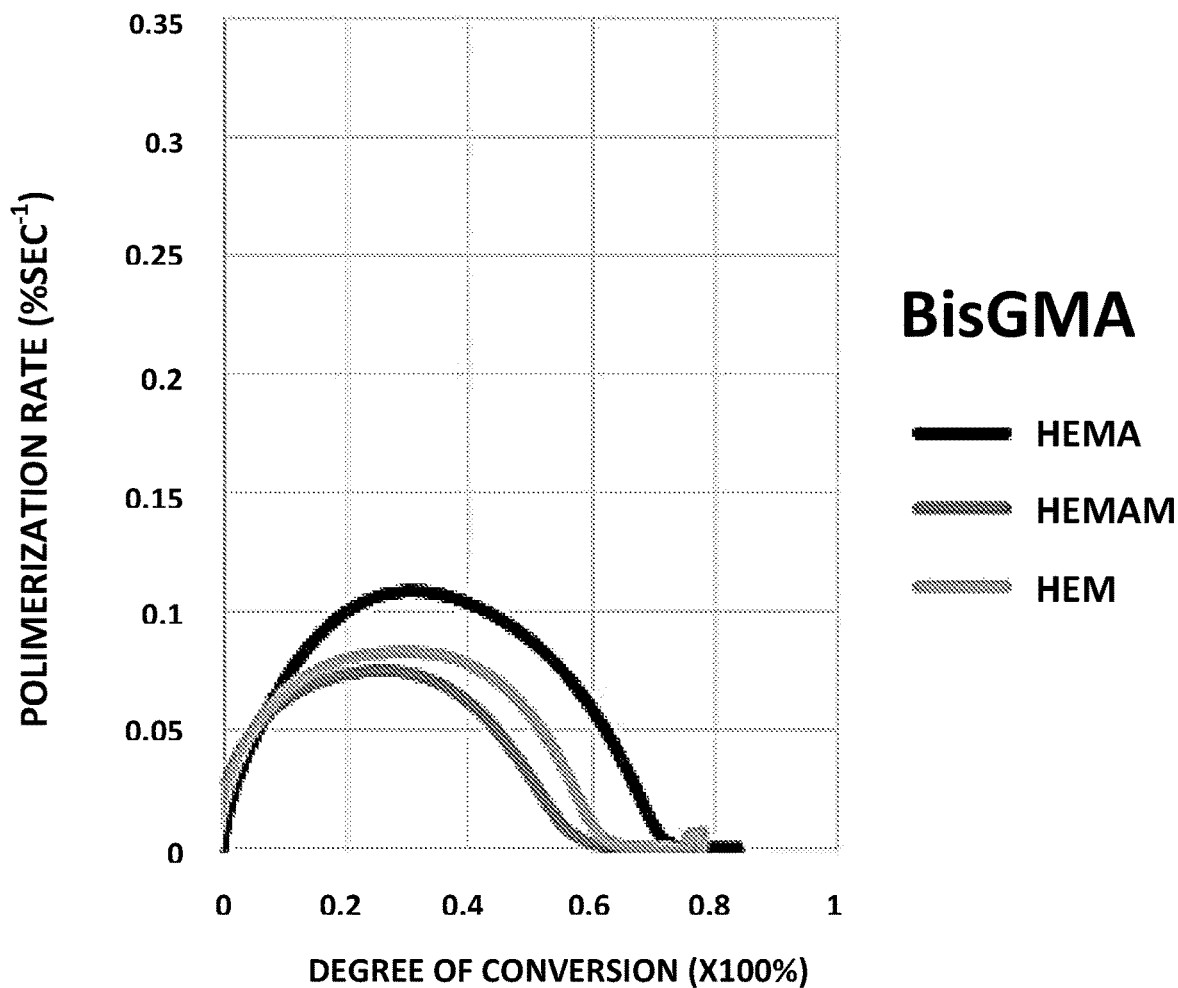
FIGS. 15A, 15B, 15C, 15D, 15E, and 15F represent polymerization rates as a function of conversion for non-solvated BisGMA and UDMA-containing adhesives.

Most commercial adhesive systems are based on ester-containing methacrylate polymers, making them susceptible to hydrolysis and enzymatic degradation [26]. (Meth)acrylamides lack ester bonds and are more hydrolytically stable [27], which makes their use for adhesive applications a logical alternative to overcome intraoral degradation issues. However, for these monomers to be useful in dental applications, a balance must exist between their reactivity and susceptibility to degradation. In this study, this was evaluated in terms of water sorption and solubility and degradation potential as a function of pH, and correlated to the short- to medium-term microtensile bond strength. BisGMA presents a few limitations as a base monomer, including the potential for BPA contamination (though the risk is low, and many studies have failed to demonstrate its presence from commercial materials containing BisGMA—[28]), the high viscosity, which precludes the inclusion of larger amounts of filler in composites, and the potentially decreased diffusion of adhesive formulations in the dentin tubules [29]. For these reasons, UDMA was also tested as a potential base monomer. When comparing monomers with the same polymerizable functionality, such as HEM and DMAM, both tertiary acrylamides, different polymerization kinetic profiles can be observed for the copolymerizations with BisGMA (FIG. 15A). DMAM had a polymerization rate almost four times greater than HEM (31.2 vs. 8.3%-sec-1, respectively), as well as higher degree of conversion (90.2% vs. 78.1%, respectively). This dramatic difference can be explained by the much lower initial viscosity of DMAM compared to HEM. BisGMA is a very viscous monomer (1400 Pa·s) and does not reach conversions much higher than 30% in homopolymerizations, due to early onset of diffusional limitations to propagation [30]. The addition of lower viscosity diluents, such as TEGDMA, has been shown to significantly increase the conversion of BisGMA [31]. In this study, the lower viscosity of DMAM contributed to delaying diffusional limitations (and the onset of autoacceleration/deceleration) to higher degrees of conversion, which increased both the maximum rate of reaction as well as the final conversion in relation to the more viscous HEM mixtures.

Figure 15B:
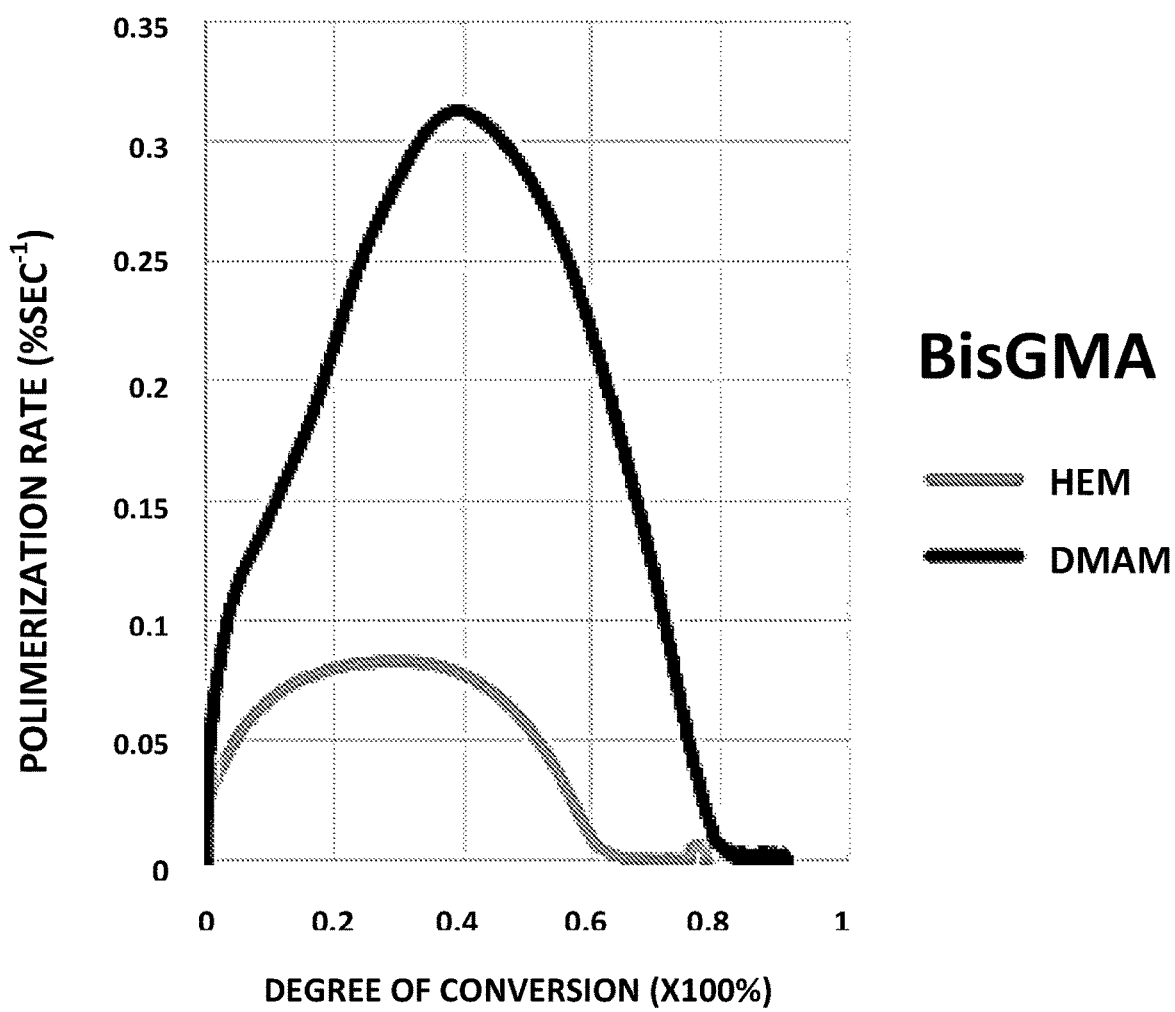
Figure 15C:
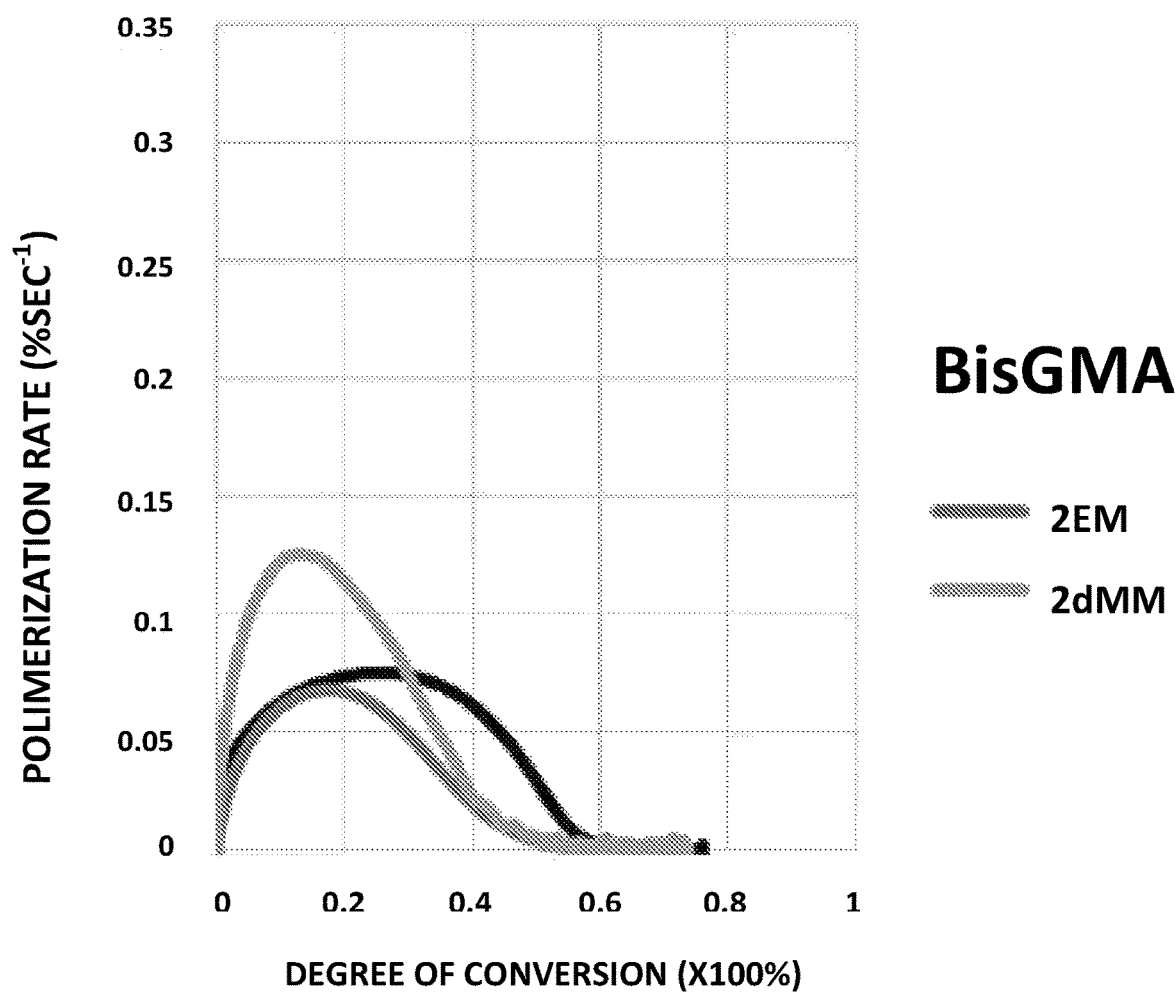
Figure 15D:
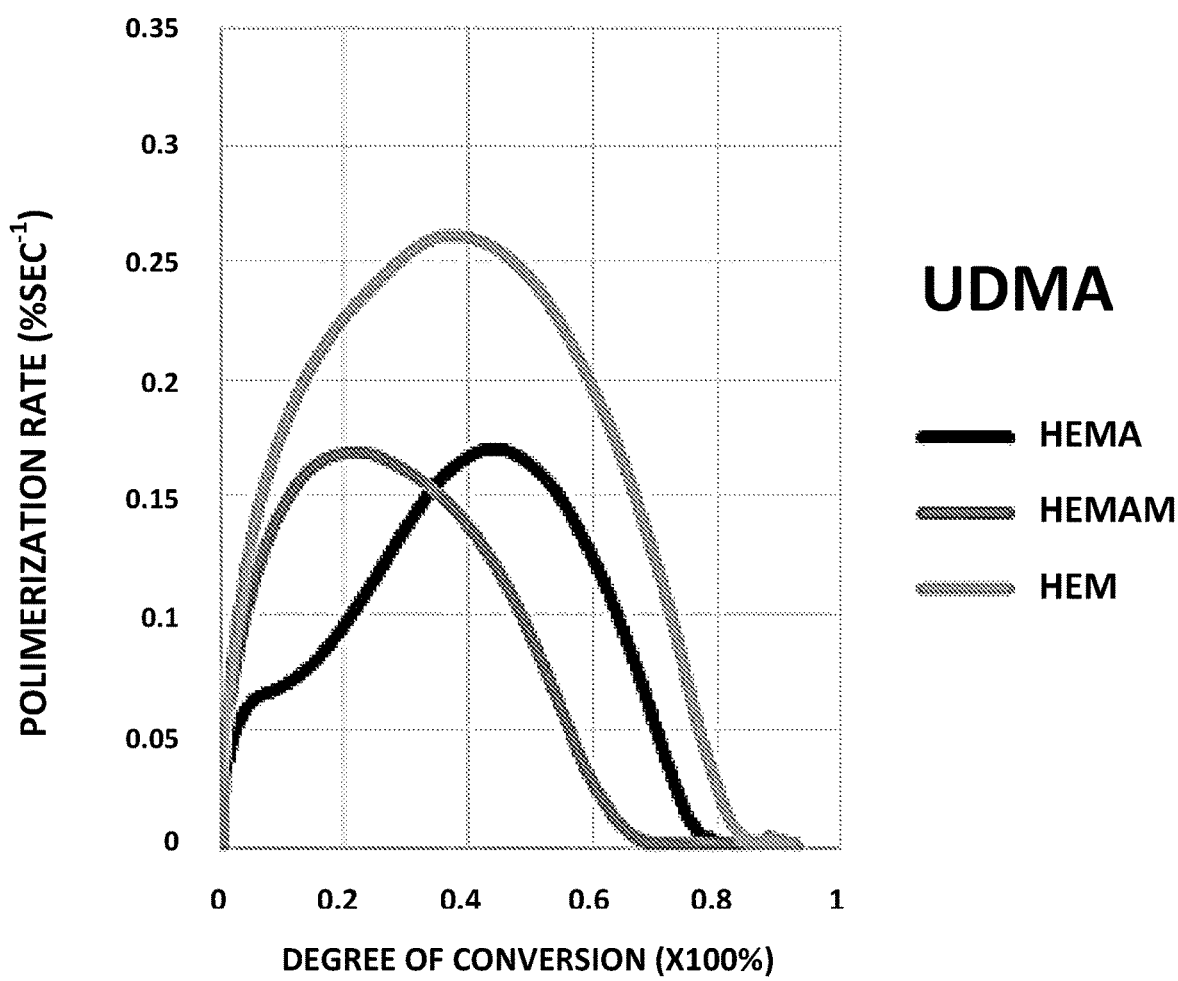
Figure 15E:
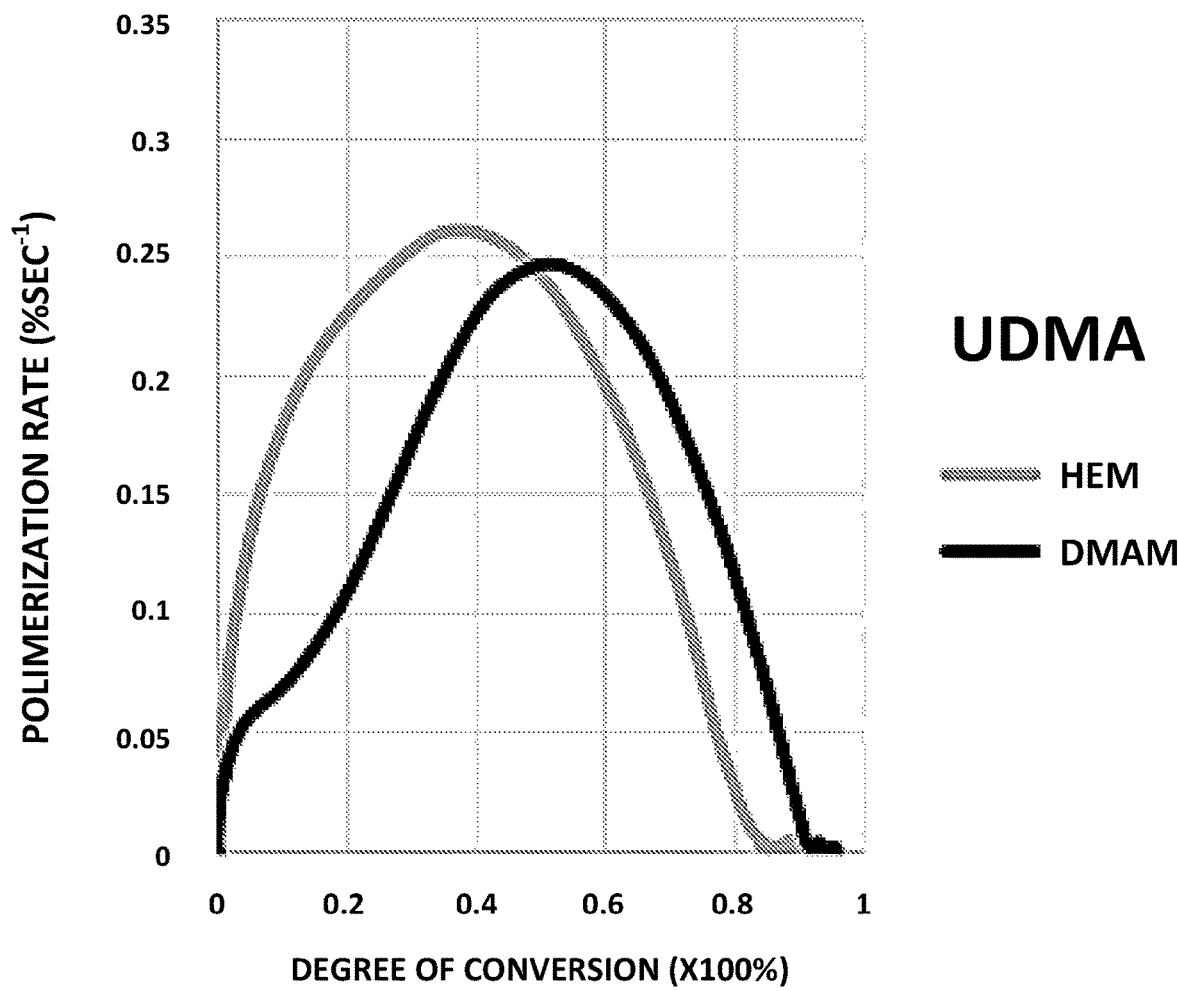
Figure 15F:
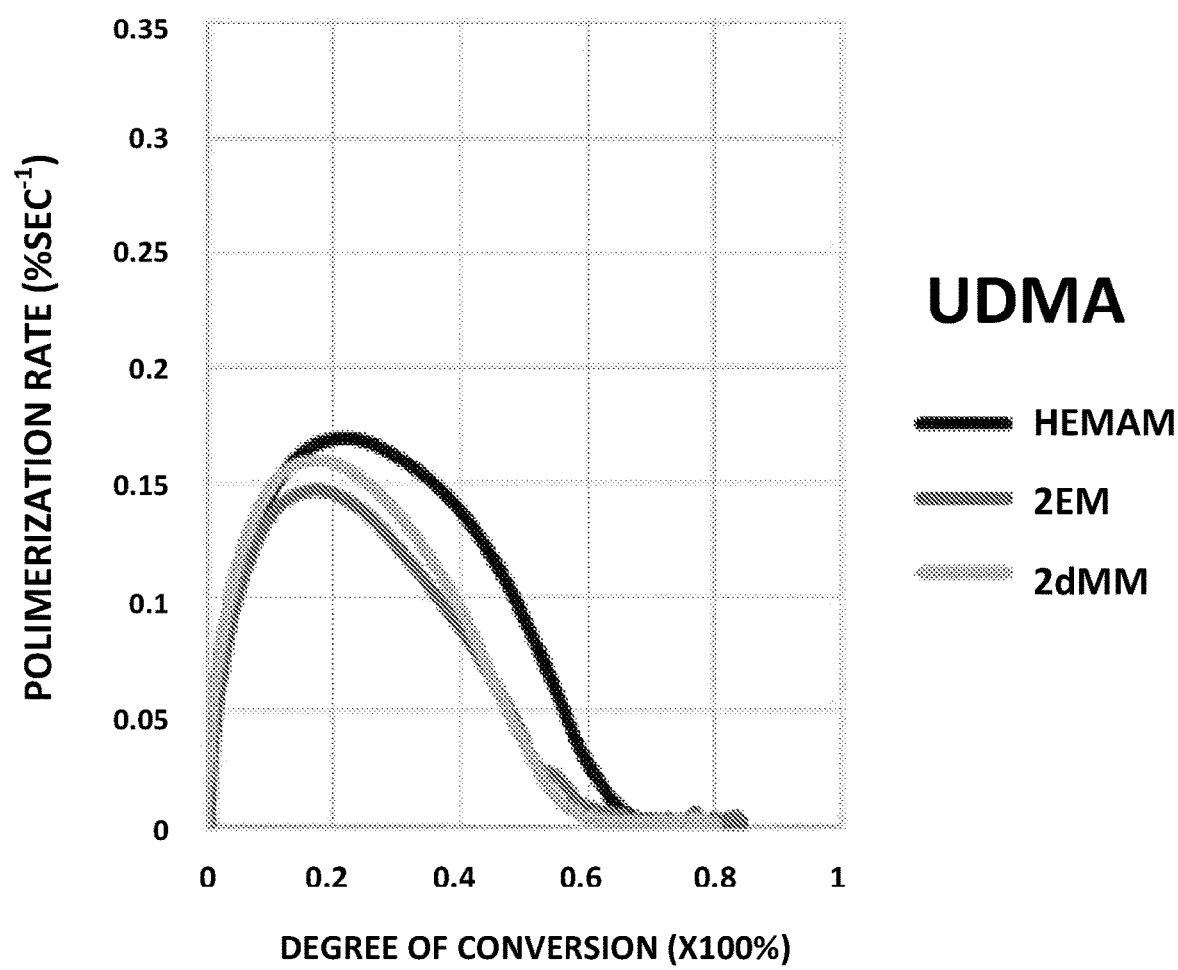

However, although the maximum rates of polymerization were similar for HEM and DMAM in copolymerizations with UDMA, their kinetic profiles were markedly different (FIG. 15B), with a two-stage kinetic profile ("shoulder") when DMAM is used (this was also the case in the copolymerization of DMAM with BisGMA and of HEMA with UDMA, discussed later). This kinetic profile, although not conclusive, points to the formation of distinct phases within the material, either via polymerization-induced phase-separation or the formation of interpenetrating polymer networks (IPNs). IPN formation, rather than copolymerization, is common when monomers with differential reactivity are polymerized together [32]. Since the reactivity of DMAM/HEMA, and monofunctional monomers in general [33], is very low in homopolymerizations, it can be speculated that the first stage in the kinetic profile corresponds to the faster polymerization of UDMA or BisGMA-rich phases, followed by the polymerization of DMAM or HEMA-rich phases [34]. Moreover, when comparing the DMAM copolymerizations with UDMA or BisGMA, the rates are much lower for the former (FIG. 5), likely due to the much greater initial viscosity for BisGMA. This led to much faster autoacceleration for BisGMA, which reached Rpmax at lower conversion and much faster deceleration than UDMA. Therefore, the mixture of DMAM/UDMA ultimately reached higher conversion than the DMAM/BisGMA mixture.

It is also possible that the miscibility of the different monomers both prior and during polymerization has influenced the results. All monomers were completely miscible at room temperature, and presented as a single phase before curing. It is possible that the mixture is only metastable, however [35]. As the polymerization proceeds, the polymeric chains increase in length and molecular weight, decreasing the entropy of mixing and reducing the miscibility [32, 36, 37]. Therefore, the degree of mixing is controlled by the balance between the kinetics and thermodynamics of cure, because large-scale macro-molecular diffusion and subsequent phase-separation are not usually observed after gelation [16, 38], with notable exceptions including liquid crystal systems, which are not relevant to the present study [35]. If sufficient cross-linking takes place before substantial diffusion of the components can occur, phase-separation is prevented and a high degree of mixing will be obtained [38, 39]. For UDMA+HEMA, the DC at Rpmax was much higher (44.7±1.0%), as compared to 29.8±1.9% for BisGMA/HEMA, indicating that the system preserved its mobility to much higher stages in conversion. This could have allowed for the diffusion of monomers in a state of meta-stability [40, 41], leading to the formation of two (or more) types of domains with different compositions [40]. The reactivity difference between the monomers involved in the mixture causes one of them to react faster, thereby forming both highly internally crosslinked and loosely connected microgel particles, and explaining the shoulder present on the kinetics curve [40].

In relation to the secondary methacrylamides with α-carbon substitutions, 2dMM showed polymerization rate that was almost twice as high as that of HEMAM (no substitution in the α-carbon) and 2EM (12.3, 7.4, and 6.7% sec-1, respectively), although the final degrees of conversion were very similar, at 73.7, 75.9, and 72.6%, respectively. This was unexpected, based on the fact that the presence of two bulky groups in 2dMM had been hypothesized to impose greater steric hindrance compared to the somewhat more flexible ethyl group in 2EM. One possible explanation is the electron-donating nature of alkyl chains, which creates a partial negative charge on the carbon they are attached to [42]. In the case of 2dMM, it is possible that partial charge was twice as strong as in 2EM. Since the amide bond is an even stronger electron-donating group [42, 43], those partial charges may have combined to provide separation from the electron-rich vinyl group, further exposing the double bond. In addition, the higher polymerization rate of 2dMM in comparison to the other secondary methacrylamides may be due to the fact that its calculated log P value is much more similar to that of BisGMA (log P: 2dMM=0.33, 2EM=0.60, HEMAM=−0.21, BisGMA=5.09)—Table 1. It can be speculated that this improves miscibility and facilitates copolymerization. In general, the association between the secondary methacrylamides with UDMA led to more reactive mixtures than with BisGMA. Comparing the kinetic results, the final degree of conversion increased between 8 and 14%, and the polymerization rate increased by more than two-fold for HEMAM and 2EM, and 25% for 2dMM when combined with UDMA (FIG. 1B). This was expected due to the difference of reactivity between UDMA and BisGMA [44], as discussed above. Another interesting aspect is that the UDMA combinations followed exactly the same trend indicated by the steric hindrance, with HEMAM being slightly more reactive than 2EM and 2dMM. However, in BisGMA mixtures, the miscibility seems to have played a more crucial role than the steric hindrance [43].

Water uptake leads to deterioration of the mechanical properties due to the increasing free volume as the water swells the polymer and disrupts intermolecular interactions between polymeric chains [45, 46]. Amides are known to be more hydrolytically stable than acrylates [47], but they have also been demonstrated to be more hydrophilic [48]. Water uptake in the amides is maximized by the fact that the electron-withdrawing oxygen of the carbonyl group decreases the nitrogen electronic density more markedly than for the oxygen-containing methacrylate, making the former slightly more polar. Interestingly, these same factors increase the resonance stability of the methacrylamide monomer, and make it less prone to hydrolysis compared to methacrylates [21]. In this study, these effects were further compounded by the fact that the mono-functional monomers were co-polymerized with dimethacrylates, which made up for 60 wt % of the overall formulation. Therefore, it was expected that the absolute values for dry and wet mechanical properties would be largely influenced by the dimethacrylate structure.

As far as the stability of the neat monomers, no degradation was observed at pH 4, 5 or 7, even after 30 days of incubation. The lack of degradation of all the monomers at pH 4 and 5, which are still acidic environments, is in agreement with the results of others [49]. At pH 1 and 2, as expected, the degree of degradation for each monomer increased with time. The results for two structurally similar monomers, methacrylamide HEMAM and methacrylate HEMA, agreed with previous reports stating that methacrylamides are more stable to hydrolysis than the analogous methacrylates [49]. This is due to the stronger character of the amide bond due to its inherent double bond component, derived from the electron donation of the nitrogen lone pair into the N—C bond. At pH 2, HEMAM did not show any significant amount of degradation products, which compared favorably to the 10.5 (0.7)% degradation for HEMA. The systematic addition of alkyl groups at the α-carbon to the nitrogen in HEMAM led to secondary methacrylamides 2dMM and 2EM. It was hypothesizes that the addition of electron-donating alkyl chains to the alpha-carbon on the methacrylamides would contribute to the stabilization of the amide bond. However, there is a clear increase of the degree of degradation as the steric bulkiness at the α-carbon increased, thus leading to a rejection of this hypothesis. These results indicate that the steric demand imparted by the substituents at that position creates strain in the amide bond, weakening it.

For BisGMA, the (meth)acrylamides had similar percent reduction in yield strength (YS) compared to the methacrylate control (HEMA). The reduction in YS values was 51% for HEMA and varied between 53-59% for the remainder groups. HEM, the tertiary acrylamide containing a terminal hydroxyl group, showed a much greater reduction in yield strength, of 64%. The reduction in modulus for the BisGMA groups was actually greater for HEMA (53%) as compared to the (meth)acrylamide groups (35-39%). Regardless, the YS and E values after storage in water were statistically similar for all groups. Interestingly, contrary to what was expected, the water sorption and solubility results did not seem to correlate with the drop in mechanical properties for the BisGMA groups. For example, DMAM had the highest WS/SL values, and yet the drop in mechanical properties was similar or less than its counterparts with much lower WS/SL values. This points to the complexity of structure-property relationships in polymer networks. At least two factors need to be considered: the partition coefficient (log P) and final degree of conversion (Table 1). Among the monofunctional monomers tested, DMAM is the second most hydrophilic (log P=0.2), and the one with the smallest molecular weight. This only partially explains why its WS was the highest. However, if the partition coefficient was the only or most important factor, then HEM (log P=−0.32) should have presented the highest WS, and at least for BisGMA copolymerizations, the opposite was observed. This was possibly related to the formation of IPNs, as already explained, which, under certain conditions, can be more prone to solvation [50]. This allied with the low log P value, helps explain the high WS observed. For UDMA based materials, the correlation between WS/SL and mechanical properties is clearer. The materials with the greatest WS were also the ones to present the highest percent reductions in both YS and E. For DMAM, the drop in YS/E after water storage was 70%, while for HEM, the reduction was 91 and 99% for YS and E, respectively. DMAM still had the statistically highest WS/SL, likely also explained by the formation of interpenetrating networks [50]. It is noteworthy that in co-polymerizations with HEMA, BisGMA (log P=5.09) presented higher WS/SL than UDMA (log P=3.64), in spite of BisGMA's higher log P and therefore, greater hydrophobic character [46, 51]. Again, this is explained based on the much greater conversion value achieved in the co-polymerization with UDMA. Finally, the secondary methacrylamides with substitution on the α-carbon (2dMM and 2EM) were the most stable compounds, with either base monomer, both in terms of WS/SL (among the lowest values achieved) and of percent mechanical property reduction (according to values calculated in Table 2). This was expected based on their relatively higher log P values (0.33 and 0.25, respectively), and also on the conversion values, which indicate co-polymerization with the base monomers. This is significant in light of the bond strength results discussed in the following paragraphs.

In terms of immediate μTBS results, formulations containing BisGMA as the base monomer presented slightly higher values compared to UDMA-based ones, in general, though the differences were not statistically significant for all groups. This is in general agreement with the mechanical properties, as already discussed. Within BisGMA groups, except for HEM formulation, all materials showed similar results (p>0.05) at 48 h. The lowest values for HEM were not completely unexpected, due to the sharp decrease in yield strength after water storage (64%) and the initially much lower modulus (60% lower than HEMA-containing materials) shown by this tertiary acrylamide. After 3 weeks and 6 months water storage, the MTBS values presented by all groups were statistically similar to the methacrylate control (HEMA). The reduction in MTBS for the HEMA containing material was about 30%, observed at 3 weeks storage and maintained at 6 months. For all other groups, no reduction in MTBS was observed. For the UDMA-based formulations, at 48 h and 3 weeks all experimental materials were statistically similar to the control, and no drop in bond strength was observed for any of the groups. After 6 months storage, all (meth)acrylamide-containing formulations had statistically higher MTBS values than the methacrylate control. While the methacrylate presented a drop of roughly 40% in MTBS after 6 months, no drop was observed for the (meth)acrylamide-containing formulations. In summary, two interesting findings need to be highlighted: 1. within a given base monomer, the (meth)acrylamides led to more stable bonds after 6 months; 2. when (meth)acrylamides were used as the monofunctional monomer, the base monomer did not affect bond strengths. This indicates that the use of these novel monomers can lead to more stable bonds, and may allow for the use of BisGMA-free formulations.

One explanation for the unstable bonding presented by the methacrylates and the consistent performance of the acrylamides and methacrylamides is based on the different enzymatic and hydrolytic degradation susceptibilities shown by these compounds, as already discussed. The fact that methacrylates are based on ester bonding makes these compounds highly prone to hydrolysis [46]. It has been well established that pendant and unreacted methacrylate monomers, in the presence of water, are hydrolyzed to produce alcohol and methacrylic acid intermediates after storage in distilled water. It is also possible for methacrylamides to undergo hydrolysis under specific conditions, but the substitution of the ester group with an amide significantly decreases this susceptibility, since this functional group is more resistant to nucleophilic attack due to resonance stabilization and the donating of non-bonded electrons from the nitrogen to the carbonyl carbon. This delocalization reduces the carbonyl carbon electrophilicity and, consequently, reduces its susceptibility to nucleophilic attack [20]. Since the oxygen in the methacrylates is more electronegative than nitrogen, this atom is less likely to donate its non-bonded electrons to the adjacent carbonyl, which results in a lower degree of resonance delocalization through the ester carbonyl than in the amide carbonyl, and makes ester carbonyl carbons more electrophilic than amide carbonyl carbons. In summary, amides undergo hydrolysis but at a slower rate than esters, which may partially explain the stable μTBS results even after a long-term storage [20].

In this study, to further improve the stability of methacrylamides, the monomers were designed to take advantage of potential steric mechanisms to curtail the hydrolysis process. Bulk substitutions were added to the carbon alpha to the carbonyl in an attempt to reduce the hydrolysis rate [20], which, allied to the other factors related to log P already discussed, may have contributed to the greater bonding strength performance of the alpha-substituted monomers 2EM and 2dMM compared to the two acrylamides. In the dentin, however, other than the presence of water, the hydrolysis may be enhanced by the presence of enzymes. At least for salivary enzymes such as cholesterol esterase and pseudocholesterol esterase, the direct hydrolysis of methacrylates has been convincingly demonstrated [46, 52]. The two monomers with the best microtensile bond strength performance (as defined by maintenance of the bond strengths value after 6 months storage) were subjected to incubation in water or in the presence of cholinesterase as neat compounds, and the percent intact monomer remaining was quantified with HPLC. The results show that under aqueous conditions, HEMA showed 8% of degradation, while 2EM and 2dMM presented virtually no degradation. Under enzymatic conditions the difference between the methacrylate and the alpha-substituted secondary methacrylamides was even more marked, with HEMA showing 52% of degraded monomers, compared to 22 and 8% for 2EM and 2dMM, respectively. In both tested conditions the methacrylamides were significantly more stable than the methacrylate, which may help explain the μTBS results, in spite of the significant drop in mechanical properties observed for those networks.

These results highlight the fact that the bonding strength is not only a product of the materials mechanical properties, but is highly dependent on the quality of the interaction between the adhesive layer and the dental substrate, complicated by temperature and chemical challenges by acids and enzymes. Several studies have shown that amides can form hydrogen-bonded interactions with the carboxylic acids of the side-chain of aspartic and/or glutamic acids in the macromolecule of the dentinal collagen [21, 48]. This occurs due to the presence of a triple helix structure associated with a hydrogen bond between the >C=O of the proline residue and the >NH of the glycine residue on the dentinal collagen [49, 53, 54]. These hydrogen bonds between the amides and the collagen fibrils would translate to stronger and more stable bond strength, besides potentially working as metalloproteinase (MMP) inhibitors [55].

In conclusion, the results of the present study indicate that the alpha-substituted secondary methacrylamides led to more stable bonds after 6 months, which was true regardless of the base monomer (BisGMA or UDMA). Steric hindrance influenced the polymerization kinetics of the monomer mixtures. However, copolymerization is a complex reaction affected by many additional factors, such as initial viscosity, partition coefficient, intermolecular interactions, and reactivity. Overall, UDMA copolymerizations were faster and progressed to a greater extent than BisGMA. These novel monomers may be a viable alternative for dental adhesives, including BisGMA-free formulations.

Synthesis Procedures for the Designed Monofunctional Monomers

General considerations: Unless otherwise stated, all reagents and solvents were purchased from commercial suppliers (Sigma-Aldrich, Fisher Scientific) and used without further purification. All reactions were conducted in standard, dry glassware and under an inert atmosphere of nitrogen. 13C-NMR and 1H-NMR spectra were recorded at room temperature on a Bruker AMX-400 MHz spectrometer using acetone-d6 or CDCl3 (Supporting Information). Chemical shifts are reported as δ values in parts per million (ppm) and coupling constants (J) are reported in Hertz. When required, a Buchi Reveleris X2 flash chromatography system was used for purification, with 20 μm particle size, 40 g silica cartridges at a flow rate of 40 mL/min, with peak detection programmed to 254 nm. The partition coefficient, log P, was calculated for all monomers used in this study using ChemBioDraw softwared (v14.2, Cambridge Soft., PerkinElmer) and is shown in Table 1.

1. N-(2-hydroxyethyl)-N-methylacrylamide (HEM): Freshly distilled acryloyl chloride (24.7 mmol, 1 equiv.) in anhydrous DCM (10 mL) was added dropwise to a stirred solution of 2-methylaminoethanol (25.94 mmol, 1.05 equiv.), trimethylamine (24.7 mmol, 1 equiv.) and 2 mg of 4-methoxyphenol in anhydrous DCM (20 mL) at −10° C. After the addition was complete, the mixture was allowed to stir at room temperature for 36 h. The mixture was then filtered and the liquid portion was washed with 0.1 M HCl solution. The organic layer was dried over MgSO4, filtered, and the solvent removed in vacuo to give the title compound as a pale yellow oil (20% yield). 1H NMR (400 MHz, acetone-d6) δ 6.68-6.86 (m, 1H), 6.12-6.22 (m, 1H), 5.54-5.68 (m, 1H), 3.96-4.40 (m, 2H), 3.68 (dt, J=10.1, 5.7 Hz, 2H), 3.52 (dt, J=6.9, 5.7 Hz, 2H), 2.91-3.22 (m, 3H). 13C NMR (101 MHz, CDCl3): δ 166.8, 129.4, 126.8, 60.6, 51.9, 35.5. HRMS (TOF-ESI): m/z calcd for C6H12NO2+ [M+H]+: 130.0863; found: 130.0856.

N-(1-hydroxy-2-methylpropan-2-yl)methacrylamide (2dMM): Freshly distilled methacryloyl chloride (51.2 mmol, 1 equiv.) in anhydrous DCM (40 mL) was added dropwise to a stirred solution of 2-amino-2-methyl-1-propanol (53.55 mmol, 1.05 equiv.), trimethylamine (51.2 mmol, 1 equiv.) and 5 mg of 4-methoxyphenol in anhydrous DCM (80 mL) at −10° C. After the addition was complete, the mixture was allowed to stir at room temperature for 36 h. The mixture was then filtered and the liquid portion was washed in turn with 60 mL of 0.1 M HCl solution, 5% NaHCO3, and brine. The organic layer was dried over MgSO4, filtered, and reduced in vacuo to give the crude product as a pale yellow oil. The crude product was purified using a Buchi Reveleris X2 flash chromatography system (mobile phase A was hexanes and mobile phase B (MPB) was EtOAc, with a gradient program of 11% MPB for 1 min, 11% MPB to 47% MPB over 14.3 min and hold at 47% for 7.2 min). The fractions were collected and the solvent removed in vacuo, yielding the final product as a colorless oil (30% yield). 1H NMR (400 MHz, CDCl3): δ 5.86 (b, 1H), 5.65 (s, 1H), 5.32 (s, 1H), 4.77 (b, 1H), 3.60 (s, 2H), 1.96-1.92 (m, 3H), 1.32 (s, 6H). 13C NMR (101 MHz, CDCl3): δ 169.5, 140.2, 119.8, 70.6, 56.0, 24.4, 18.7. HRMS (TOF-ESI): m/z calcd for C8H16NO2+ [M+H]+: 158.1176; found: 158.1170.

N-(1-hydroxybutan-2-yl)methacrylamide (2EM): Freshly distilled methacryloyl chloride (51.2 mmol, 1 equiv.) in anhydrous DCM (40 mL) was added dropwise to a stirred solution of 2-amino-1-butananol (53.55 mmol, 1.05 equiv.), trimethylamine (51.2 mmol, 1 equiv.) and 5 mg of 4-methoxyphenol in anhydrous DCM (80 mL) at −10° C. under inert atmosphere (nitrogen gas). After the addition was complete, the mixture was allowed to stir at room temperature for 36 h. The mixture was then filtered and the liquid portion was washed in turn with 60 mL of 0.1 M HCl solution, 5% NaHCO3, and brine. The organic layer was dried over MgSO4, filtered and reduced in vacuo to give the crude product as a pale yellow oil. The crude product was purified using a Buchi Reveleris X2 flash chromatography system (mobile phase A was hexanes and mobile phase B (MPB) was EtOAc, with a gradient program of 29% MPB for 1 min, 29% MPB to 74% MPB over 14.3 min, hold at 74% for 7.3 min). The fractions were collected and the solvent removed in vacuo, yielding the final product as a colorless oil (12% yield). δ 6.06 (b, 1H), 5.71 (s, 1H), 5.34 (s, 1H), 3.94-3.86 (m, 1H), 3.72-3.60 (m, 2H), 3.19 (b, 1H), 1.96 (s, 3H), 1.70-1.48 (m, 2H), 0.96 (t, J=7.5 Hz, 3H). 13C NMR (101 MHz, CDCl3) δ 169.4, 140.0, 120.0, 65.2, 53.5, 24.3, 18.8, 10.7. HRMS (TOFESI):

m/z calcd for C8H16NO2+ [M+H]+: 158.1176; found: 158.1186.

Calculation of the degree of degradation. The percentage degradation values were calculated from the integrals of the vinylic protons, where ∫ Hz1 is the integral of the vinylic protons of the monomer (HEMA) and ∫ Hy1 is the integral of the vinylic protons of the methacrylic acid formed from the hydrolysis of the monomer as shown in Figure A10 (reaction 1). These values were then entered into Eq. 1 to give the percentage degradation value, X. The degree of degradation for monomers 1, 2 and 3a was initially calculated using this equation.

$$X = \left( \frac{\{\int Hy1\}}{(\{\int Hy1 + \int Hz1\})} \right) \times 100 \quad \text{Eq. 1}$$

Reaction Schemes for the Degradation of HEMA and One Representative Alpha-Substituted Methacrylamide.
Reaction Hydrolysis of HEMA

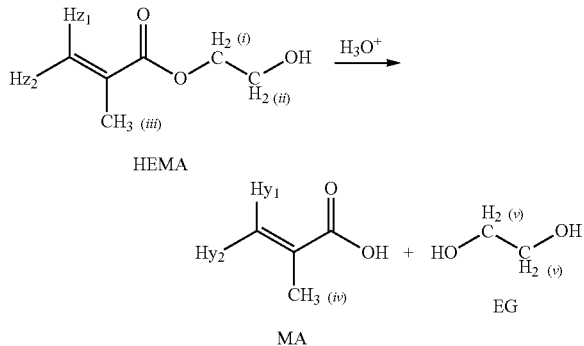

HEMA

MA

Reaction 2: Hydrolysis of One Alpha-Substituted Methacrylamide and Recombination of Degradation Products

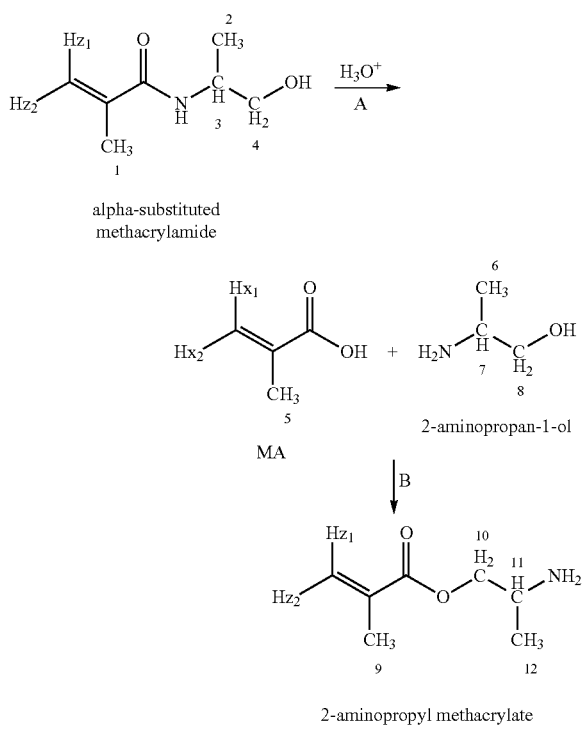

alpha-substituted methacrylamide

MA 2-aminopropan-1-ol 2-aminopropyl methacrylate

Figure 11:
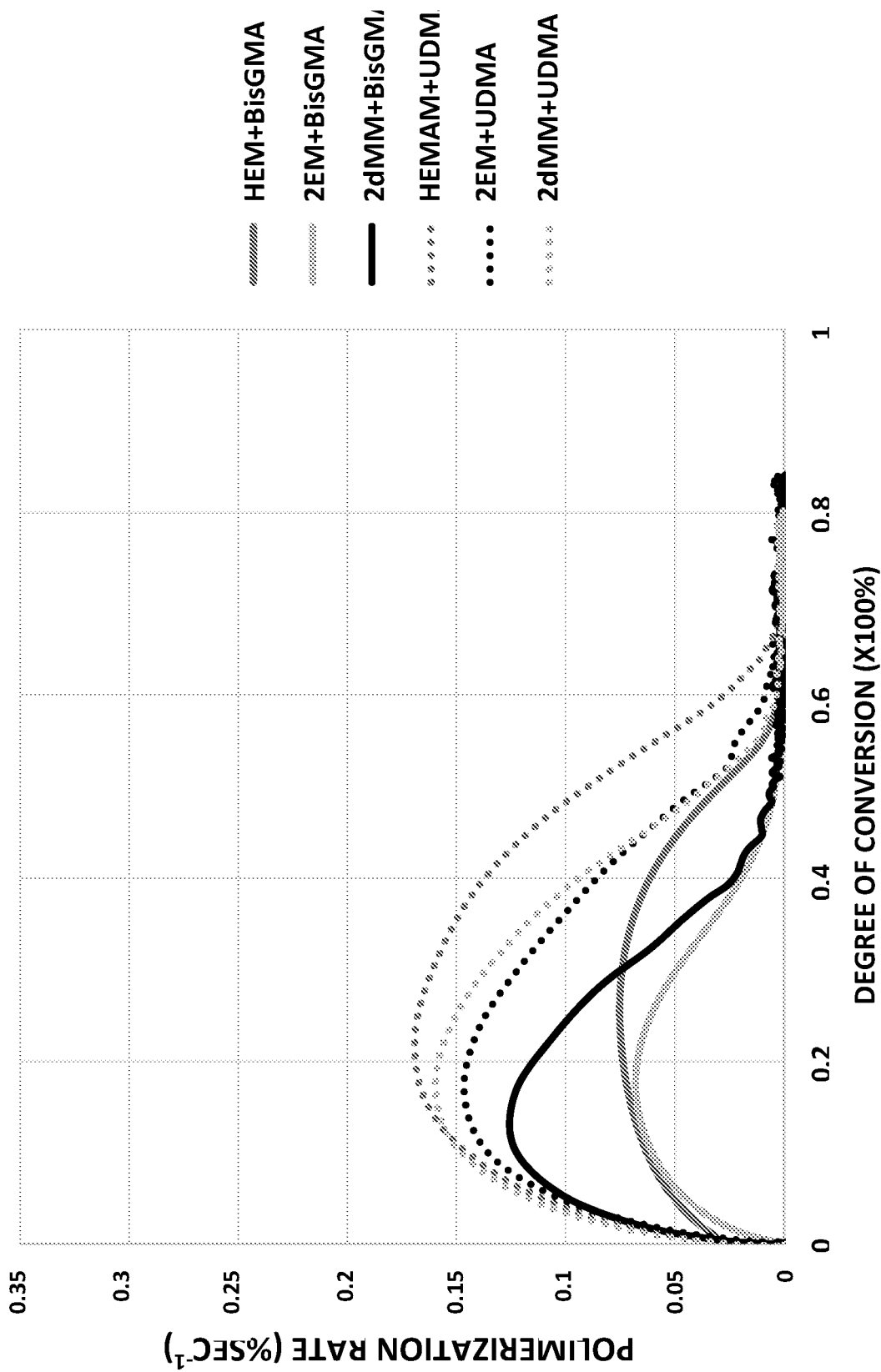
FIG. 11 represents polymerization rates for combinations of HEMAM, 2EM, and 2dMM with BisGMA and UDM.

1H NMR peak assignments for methacrylates. The hydrolytic cleavage on HEMA leads to the formation of methacrylic acid (MA) and ethylene glycol (EG) (Appendix FIG. 10, Reaction 1). Appendix FIG. 11 shows the 1H NMR spectra in D2O at pH 1 for EG, with a peak at 3.66 ppm for the methylene proton (v), and MA, with vinyl proton peaks Hy1 and Hy2 (6.10-6.09 and 5.70-5.71 ppm, respectively) and the methyl protons (iv) appearing at 1.89 ppm. On day 0 of the hydrolysis process of HEMA at pH=1, only the signals for the three different protons i through iii and the vinyl peaks Hz1 (6.14-6.13 ppm) and Hz2 (5.71-5.70 ppm) were observed. On day 5, new peaks appeared in the vinyl region (Hy1, 6.11 ppm) and in the methylene region (1.89 ppm), which were both attributed to MA. The intensity of the peak at 6.71-6.70 ppm increased as a result of overlap of two vinyl peaks (Hz2 and Hy2 from HEMA and MA, respectively). The new peak at 3.66 ppm was attributed to the appearance of EG. After storage for 30 days, the intensity of the peaks corresponding to the degradation products peaks (Hy2, Hz2, iv and v) increased while the intensity of HEMA peaks (Hz1, i, ii and iii) decreased.

Figure 12:
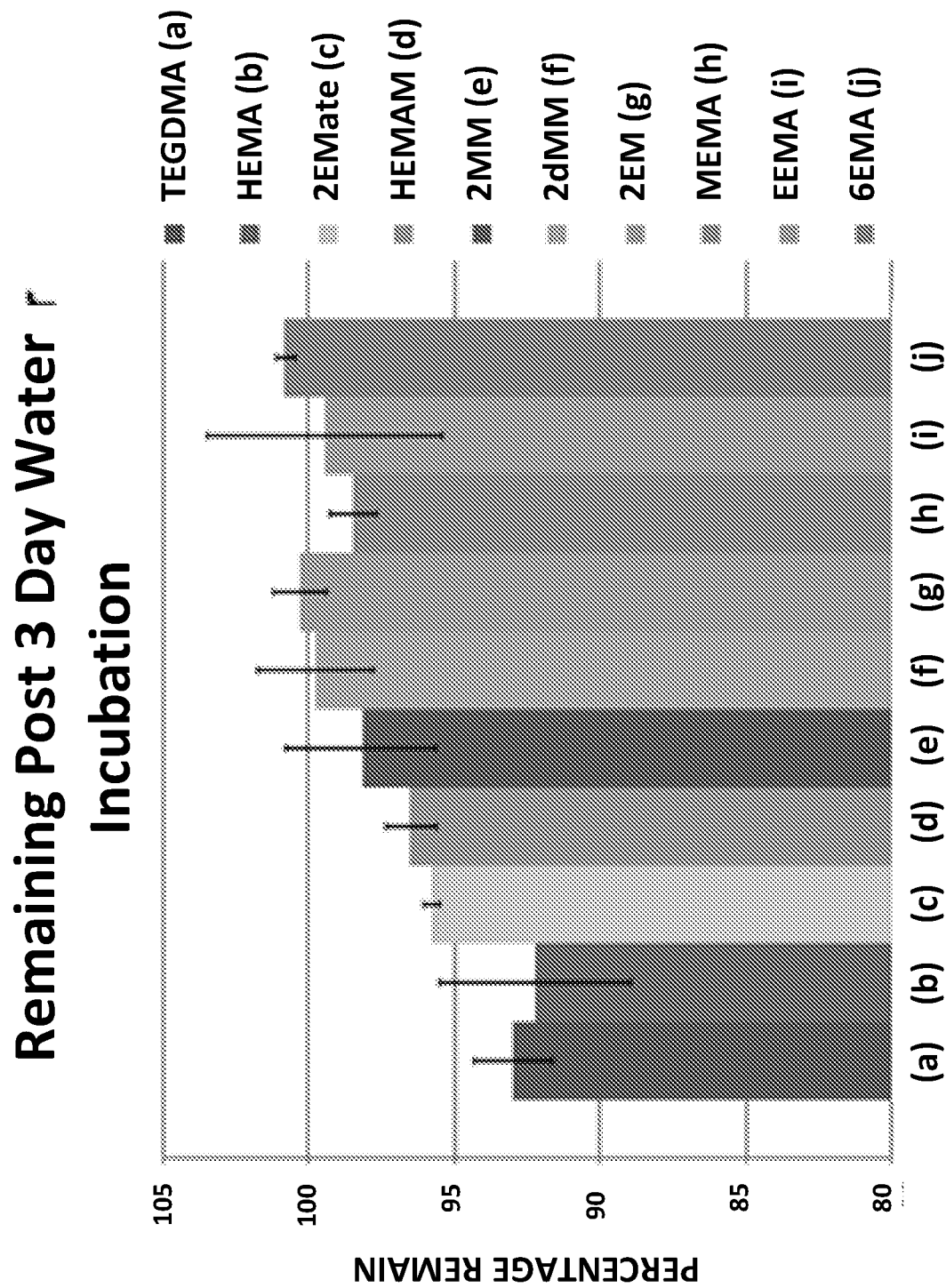
FIG. 12 represents remaining monomers post 3 days of water incubation.
Figure 13:
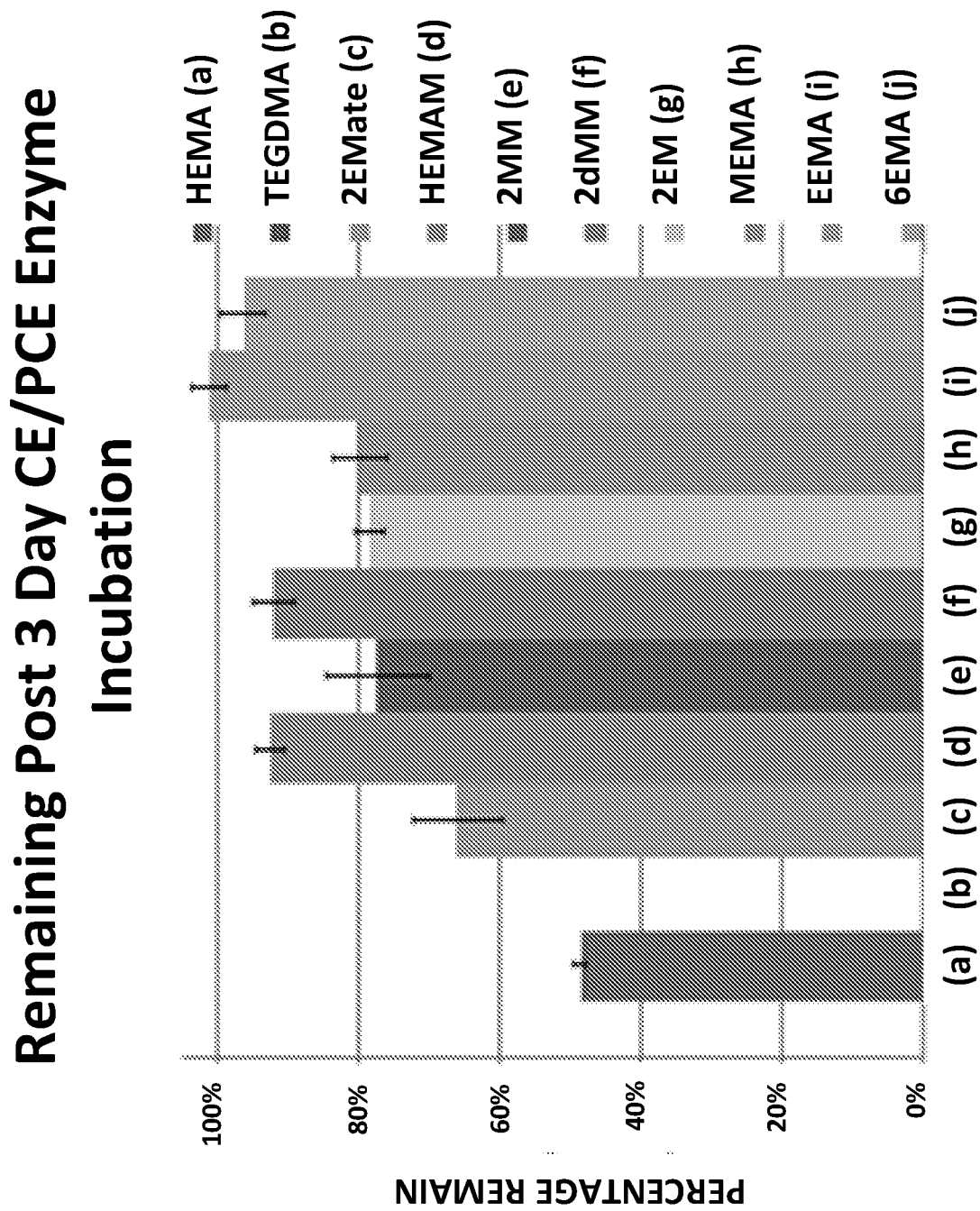
FIG. 13 represents remaining monomers post 3 days of incubation in cholinesterase (CE) and pseudocholinesterase (PCE).
Figure 14:
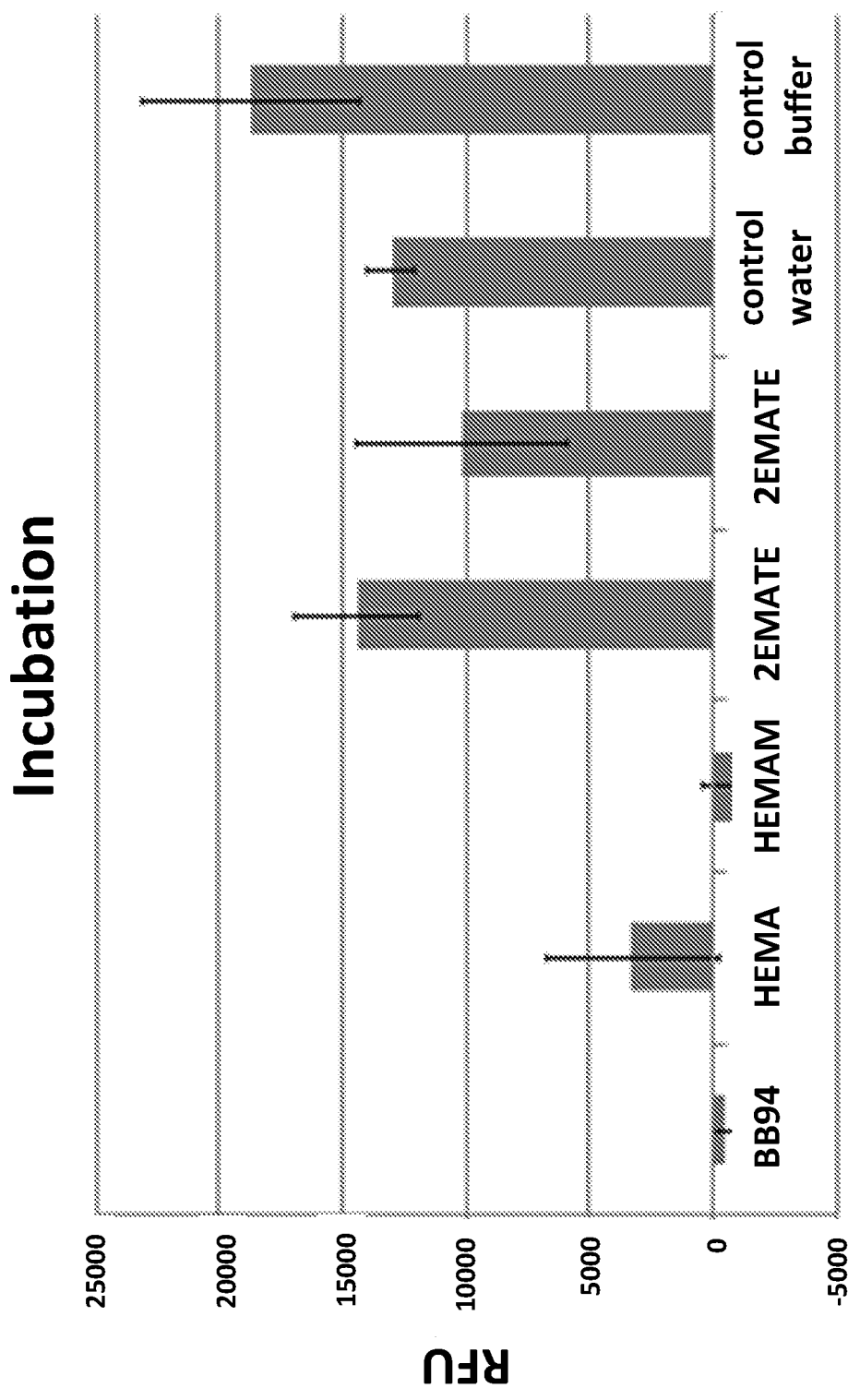
FIG. 14 represents remaining monomers post 24 hour MMP-2 incubation.

Modified 1H-NMR peak assignments. The degradation of the novel methacrylamides (2dMM and 2EM) produced additional peaks for identification. At pH 1, we observed the appearance of a series of new, unidentified peaks in both vinylic and alkylic regions. We tentatively assigned these peaks to a new methacrylate being formed from the acid-catalyzed esterification of MA with the alcohol terminus of the amino-alcohol. As a representative example of this process, Appendix FIG. 10, Reaction 2 distinguishes between reaction A, which is the acid-catalyzed amide hydrolysis pathway, showing the cleavage of the C—N bond to give MA and 2-aminopropan-1-ol, and reaction B, which is the acid-catalyzed acylation of the alcohol group in 2-aminopropanol, forming a new methacrylate monomer. Appendix FIG. 12 shows the 1H NMR spectra of 2dMM in a pH=1 aqueous solution for days 0, 5 and 30. In day 0, only the 1H NMR peaks for the four proton regions (peaks 1-4) and the vinyl peaks Ha1 (5.66-5.60 ppm) and Ha2 (5.40 ppm) were detected. On day 5, new peaks appeared in the methylene region (Hx1, 6.09 ppm) and Hx2, 5.69 ppm) and in the alkyl region (5, 1.87 ppm), which were attributed to MA, and peaks 6-8 which were assigned to 2-aminopropano-1-ol. However, on day 30 the intensity of the peaks of the hydrolysis products had decreased and new peaks had appeared. These peaks were labelled Hb1 and Hb2 in the methylene region and peaks 9-12 in alkyl region. We tentatively assigned these new peaks to 2-aminopropyl methacrylate which could be formed as a product of the esterification of the hydrolysis products.

In contrast to the case of HEMA, there was no overlapping of the vinyl protons of the monomers and MA for any of the methacrylamides. As a result, Eq. 1 was modified to include all vinylic protons. The percentage degradation values were calculated from the integrals of the vinylic protons, where $\int$ Ha1 and $\int$ Ha2 are the integrals of the vinylic protons of the monomers and $\int$ Hx1 and $\int$ Hx2 are the integrals of vinylic protons of the methacrylic acid formed from the hydrolysis of the monomer. These values were then entered into Eq. 2 to give the percentage degradation value, X.

$$X = \left( \frac{\{\int Hx1 + \int Hx2\}}{(\{\int Hx1 + \int Hx2 + \int Ha1 + \int Ha2\})} \right) \times 100 \quad \text{Eq. 2}$$

Equation 2 was then simplified to Equation 3, where $\int$ HA is the sum of $\int$ Ha1 and $\int$ Ha2 and $\int$ HX the sum of $\int$ Hx1 and $\int$ Hx2.

$$X = \left( \frac{\{\int HX\}}{(\int HA + \int HX)} \right) \times 100 \quad \text{Eq. 3}$$

In order to account for the in situ formation of the new methacrylate, a further modification of Equation 3 was made by introducing $\int$ HB, which is the sum of the methacrylate vinyl protons ∫ Hb1 and ∫ Hb2. Equation 4 was therefore used to calculate the degree of degradation the monomers in which this phenomenon was observed.

$$X = \left( \frac{\{\int HX\} + \int HB}{(\int HA + \int HX + \int HB)} \right) \times 100 \qquad \text{Eq. 4}$$

FIG. 15: Polymerization rate (%·s−1) as a function of conversion (%) for non-solvated BisGMA and UDMA-containing adhesives are shown in FIGS. 15A and B, respectively. Vinyl conversion was followed in real-time as the materials were photocured (630 mW/cm2 for 300 seconds). (A1 and B1) Comparison of methacrylate, secondary methacrylamide and tertiary acrylamide. (A2 and B2) Comparison of the two tertiary acrylamides. (A3 and B3) Comparison of the secondary methacrylamides.

FIG. 16. Water sorption and Solubility results for all tested copolymerizations. Different uppercase letters indicate statistically significant differences among the monofunctional monomers copolymerized with BisGMA (p≤0.05). Different lowercase letters indicate statistically significant differences among the monofunctional monomers copolymerized with UDMA copolymerizations (p≤0.001). Significant differences between BisGMA and UDMA within the same monofunctional monomer are indicated by asterisks (p<0.05).

Figure 17B:
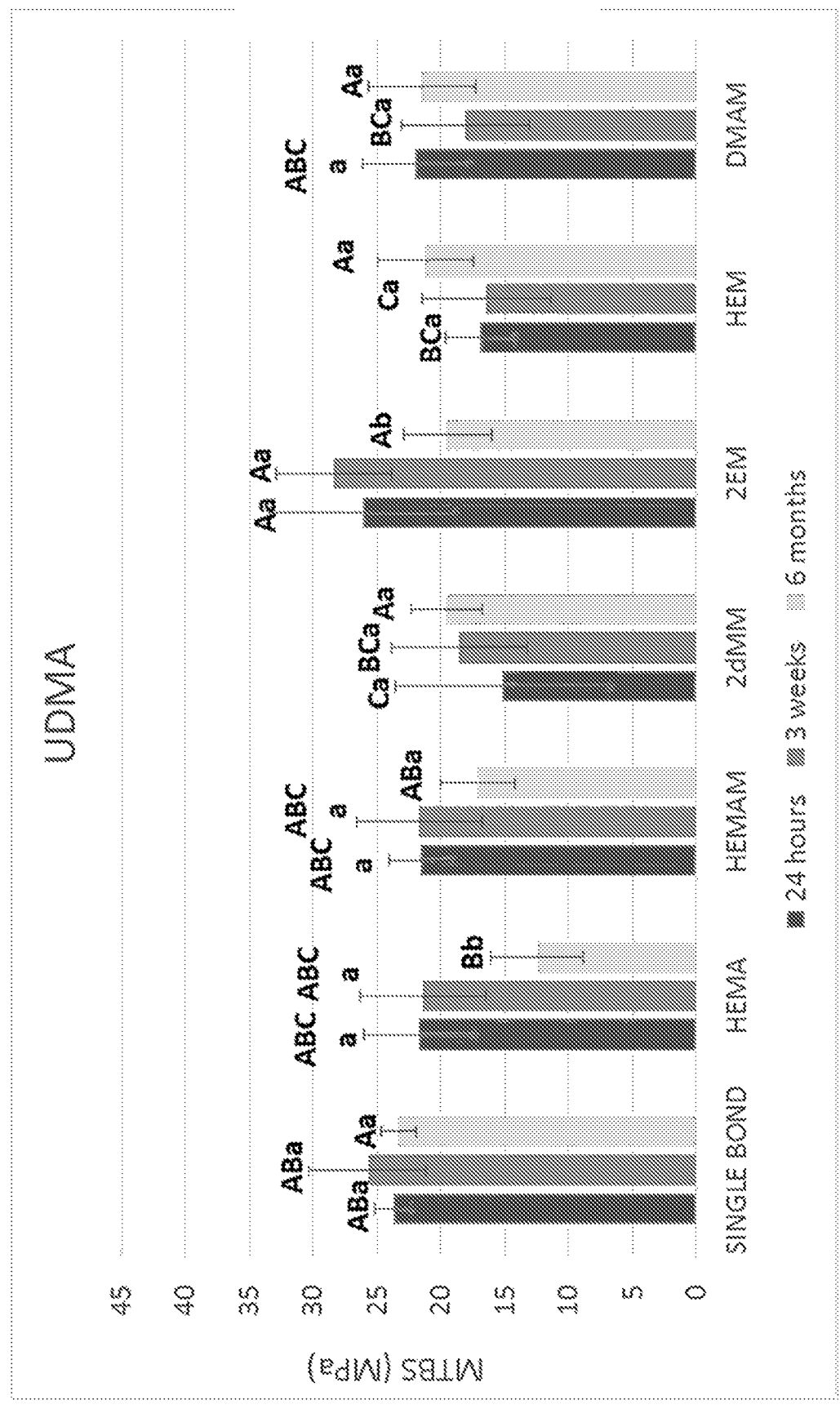

FIG. 17. Dentin Micro-tensile Bond Strength (MPa) for control groups and all monofunctional monomers copolymerized with BisGMA and UDMA after 24 hours (blue), 3 weeks (orange) and 6 months (grey) water storage. Different uppercase letters indicate statistically significant differences between the groups within the same storage time (p<0.05). Different lowercase letters indicate statistically significance difference between the storage times within the same group. Significant differences between BisGMA and UDMA within the same monofunctional monomer are indicated by asterisks (p<0.05). The BisGMA/HEMAM materials were not tested at 6 months.

FIG. 18. Percentage of remaining monomer after hydrolytic degradation at pH 1 and 2, as determined by the 1H-NMR experiments (described in detail in the appendix). Different uppercase letters indicated statistical difference among neat monomers incubated at pH 1 and different lowercase letters indicated statistical difference among neat monomers incubated at pH 2 (p≤0.001). Note: the tertiary methacrylamide (HEMMA) was tested instead of the tertiary acrylamide (HEM). DMAM was not tested.

Figure 19A:
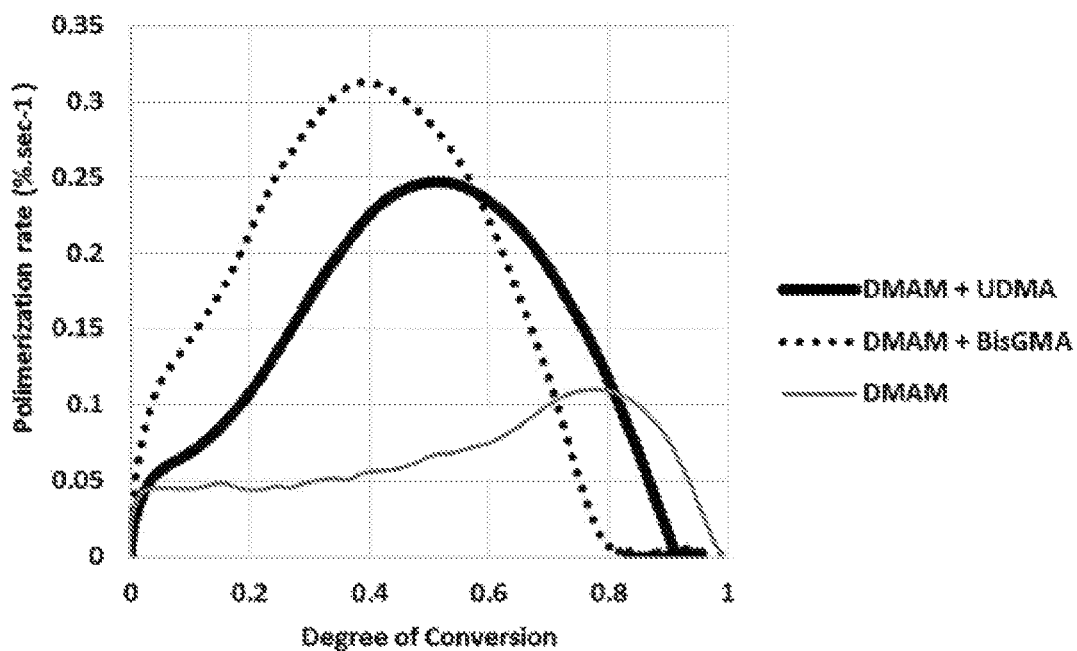
FIGS. 19A and B present (A) polymerization curves of DMAM alone and combined with UDMA and BisGMA and (B) comparison of UDMA and BisGMA mixed with secondary methacrylamides.
Figure 19B:
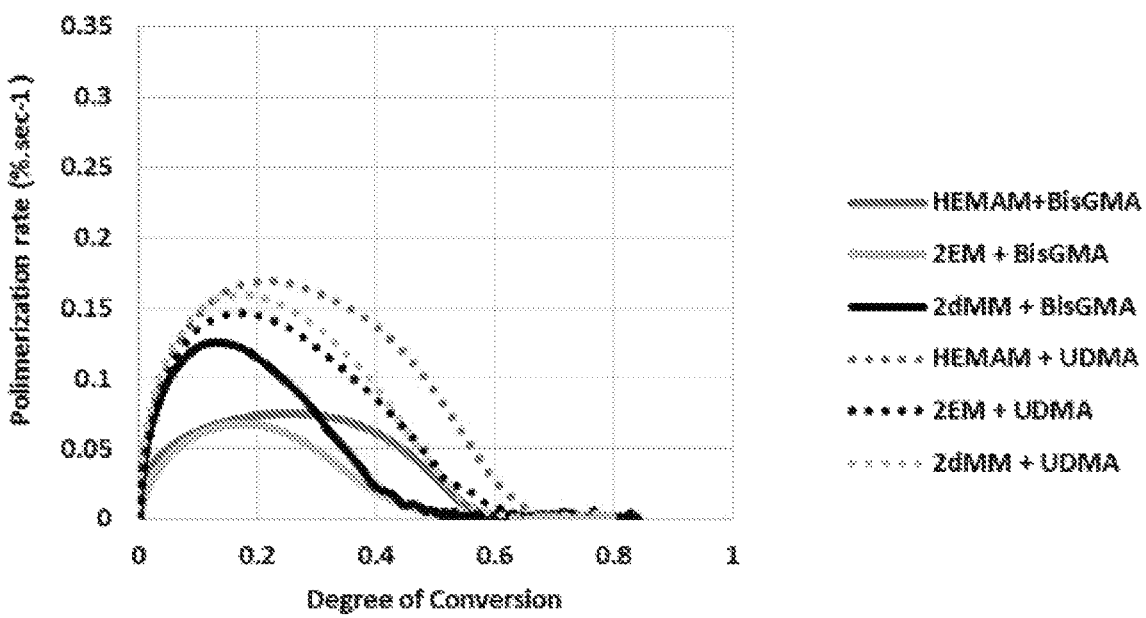

FIG. 19: (A) Kinetics polymerization curves of pure DMAM and combined with UDMA and BisGMA. (B) Comparison between UDMA and BisGMA when mixed with the secondary methacrylamides.

REFERENCES

[1] Nakabayashi N, Takarada K. Effect of HEMA on bonding to dentin. Dental Materials. 1992; 8:125-30.
[2] Van Landuyt K L, Snauwaert J, De Munck J, Peumans M, Yoshida Y, Poitevin A, et al. Systematic review of the chemical composition of contemporary dental adhesives. Biomaterials. 2007; 28:3757-85.
[3] Burrow M F, Inokoshi S, Tagami J. Water sorption of several bonding resins. American Journal of Dentistry. 1999; 12:295-8.
[4] Tanaka J, Ishikawa K, Yatani H, Yamashita A, Suzuki K. Correlation of dentin bond durability with water absorption of bonding layer. Dent Mater J. 1999; 18:11-8.
[5] Tay F R, Pashley D H. Water treeing—A potential mechanism for degradation of dentin adhesives. American Journal of Dentistry. 2003; 16:6-12.
[6] Pashley D H, Tay F R, Yiu C, Hashimoto M, Breschi L, Carvalho R M, et al. Collagen degradation by host-derived enzymes during aging. Journal of Dental Research. 2004; 83:216-21.
[7] Moszner N, Zeuner F, Fischer U K, Rheinberger V. Monomers for adhesive polymers, 2: Synthesis and radical polymerisation of hydrolytically stable acrylic phosphonic acids. Macromolecular Chemistry and Physics. 1999; 200:1062-7.
[8] Rodrigues S B, Petzhold C L, Gamba D, Leitune V C B, Collares F M. Acrylamides and methacrylamides as alternative monomers for dental adhesives. Dental Materials. 2018; 34:1634-44.
[9] Aykor A, Ozel E. Five-year clinical evaluation of 300 teeth restored with porcelain laminate veneers using total-etch and a modified self-etch adhesive system. Operative Dentistry. 2009; 34:516-23.
[10] Can Say E, Yurdaguven H, Ozel E, Soyman M. A randomized five-year clinical study of a two-step self-etch adhesive with or without selective enamel etching. Dental Materials Journal. 2014; 33:757-63.
[11] Xu X, Wang Y, Liao S, Wen Z T, Fan Y. Synthesis and characterization of antibacterial dental monomers and composites. Journal of Biomedical Materials Research—Part B Applied Biomaterials. 2012; 100 B:1151-62.
[12] Miyake G, Caporaso L, Cavallo L, Chen E Y X. Coordination addition polymerization and kinetic resolution of methacrylamides by chiral metallocene catalysts. Macromolecules. 2009; 42:1462-71.
[13] Yokota K, Oda J. Kogyo Kagaku Zasshi. 1970; 70.
[14] Kelsch A, Tomcin S, Rausch K, Barz M, Mailänder V, Schmidt M, et al. HPMA copolymers as surfactants in the preparation of biocompatible nanoparticles for biomedical application. Biomacromolecules. 2012; 13:4179-87.
[15] Moszner N, Zeuner F, Angermann J, Fischer U K, Rheinberger V. Monomers for adhesive polymers, 4: Synthesis and radical polymerization of hydrolytically stable crosslinking monomers. Macromolecular Materials and Engineering. 2003; 288:621-8.
[16] Chen F, Cook W D. Curing kinetics and morphology of IPNs from a flexible dimethacrylate and a rigid epoxy via sequential photo and thermal polymerization. European Polymer Journal. 2008; 44:1796-813.
[17] Tauscher S, Angermann J, Catel Y, Moszner N. Evaluation of alternative monomers to HEMA for dental applications. Dental Materials. 2017; 33:857-65.
[18] Catel Y, Fischer U K, Moszner N. Monomers for adhesive polymers: 11. Structure adhesive properties relationships of new hydrolytically stable acidic monomers. Polymer International. 2013; 62:1717-28.
[19] Catel Y, Fischer U K, Moszner N. Monomers for adhesive polymers, 13.1 Synthesis, radical photopolymerization and adhesive properties of polymerizable 2-substituted 1,3-propylidenediphosphonic acids. Designed Monomers and Polymers. 2014; 17:286-99.
[20] Ruiter J D. Principles of Drug Action 1: Springer; 2005.
[21] Otsu T, Inoue M, Yamada B, Mori T. Structure and reactivity of vinyl monomers: Radical reactivities of N-substituted acrylamides and methacrylamides. J Polym Sci, Polym Lett Ed. 1975; 13.

[22] Rueggeberg F A, Craig R G. Correlation of Parameters used to Estimate Monomer Conversion in a Light-cured Composite. Journal of Dental Research. 1988; 67:932-7.

[23] Rueggeberg F A, Hashinger D T, Fairhurst C W. Calibration of FTIR conversion analysis of contemporary dental resin composites. Dental materials: official publication of the Academy of Dental Materials. 1990; 6:241-9.

[24] Stansbury J W, Dickens S H. Determination of double bond conversion in dental resins by near infrared spectroscopy. Dental Materials. 2001; 17:71-9.

[25] ISO-4049. ISO 4049:2009—Dentistry—Polymer-based restorative materials. 2009.

[26] Finer Y, Santerre J P. Biodegradation of a dental composite by esterases: Dependence on enzyme concentration and specificity. Journal of Biomaterials Science, Polymer Edition. 2003; 14:837-49.

[27] Xu X, Wang R, Ling L, Burgess J O. Synthesis and stability study of dental monomers containing methacrylamidoethyl phosphonic acids. Journal of Polymer Science, Part A: Polymer Chemistry. 2007; 45:99-110.

[28] Macaulay M, Tam L E, Santerre J P, Finer Y. In vivo biodegradation of bisGMA and urethane-modified bisGMA-based resin composite materials. JDR Clinical and Translational Research. 2017; 2:397-405.

[29] Sakaki T, Fukushima T, Kawai S, Matsumoto M. Effect of physical properties of direct bonding adhesives on bonding to etched enamel. The Journal of Prosthetic Dentistry. 1994; 71:552-9.

[30] Gajewski V E S, Pfeifer C S, Froes-Salgado N R G, Boaro L C C, Braga R R. Monomers used in resin composites: Degree of conversion, mechanical properties and water sorption/solubility. Brazilian Dental Journal. 2012; 23:508-14.

[31] Lovell L G, Stansbury J W, Syrpes D C, Bowman C N. Effects of composition and reactivity on the reaction kinetics of dimethacrylate/dimethacrylate copolymerizations. Macromolecules. 1999; 32:3913-21.

[32] Dean K M, Cook W D. Azo initiator selection to control the curing order in dimethacrylate/epoxy interpenetrating polymer networks. Polymer International. 2004; 53:1305-13.

[33] Hild G, Rempp P. Mechanism of network formation by radical copolymerization. Pure and Applied Chemistry. 1981; 53:1541-56.

[34] Pfeifer C S, Shelton Z R, Braga R R, Windmoller D, MacHado J C, Stansbury J W. Characterization of dimethacrylate polymeric networks: A study of the crosslinked structure formed by monomers used in dental composites. European Polymer Journal. 2011; 47:162-70.

[35] Kloosterboer J G, Serbutoviez C, Touwslager F J. Monitoring of polymerization-induced phase separation by simultaneous photo-d.s.c./turbidity measurements. Polymer. 1996; 37:5937-42.

[36] Ali S A M, Hourston D J. Advances in Interpenetrating Polymer Networks: Technomic Publishing Company; 1994.

[37] Utracki L A. interpenetrating Polymer Networks: American Chemical Society; 1994.

[38] Dean K, Cook W D. Effect of curing sequence on the photopolymerization and thermal curing kinetics of dimethacrylate/epoxy interpenetrating polymer networks. Macromolecules. 2002; 35:7942-54.

[39] Suthar B, Xiao H X, Klempner D, Frisch K C. IPNs around the world: Science and Engineering.: Wiley: New York; 1997.

[40] Boots H M J, Kloosterboer J G, Serbutoviez C, Touwslager F J. Polymerization-induced phase separation. 1. Conversion-phase diagrams. Macromolecules. 1996; 29:7683-9.

[41] Serbutoviez C, Kloosterboer J G, Boots H M J, Touwslager F J. Polymerization-induced phase separation. 2. Morphology of polymer-dispersed liquid crystal thin films. Macromolecules. 1996; 29: 7690-8.

[42] Bruice P Y. Organic Chemistry. 8th ed. Santa Barbara: Pearson; 2016.

[43] Casis N, Luciani C V, Estenoz D A, Martinelli M, Strumia M, Meira G R. Partition of tertdodecyl mercaptan in systems containing styrene, polystyrene, and polybutadiene. Its effect on the macromolecular characteristics of high-impact poly styrene. E-Polymers. 2007.

[44] Dickens S H, Stansbury J W, Choi K M, Floyd C J E. Photopolymerization kinetics of methacrylate dental resins. Macromolecules. 2003; 36:6043-53.

[45] Hodge R M, Bastow T J, Edward G H, Simon G P, Hill A J. Free Volume and the Mechanism of Plasticization in Water-Swollen Poly(vinyl alcohol). Macromolecules. 1996; 29:8137-43.

[46] Santerre J P, Shajii L, Leung B W. Relation of dental composite formulations to their degradation and the release of hydrolyzed polymeric-resin-derived products. Critical Reviews in Oral Biology and Medicine. 2001; 12:136-51.

[47] Delaviz Y, Finer Y, Santerre J P. Biodegradation of resin composites and adhesives by oral bacteria and saliva: A rationale for new material designs that consider the clinical environment and treatment challenges. Dental Materials. 2014; 30:16-32.

[48] Dušek K, Janáček J. Hydrophilic gels based on copolymers of 2-hydroxyethyl methacrylate with methacrylamide and acrylamide. Journal of Applied Polymer Science. 1975; 19:3061-75.

[49] Nishiyama N, Suzuki K, Asakura T, Komatsu K, Nemoto K. Adhesion of Nmethacryloyl-ω-amino acid primers to collagen analyzed by 13C NMR. Journal of Dental Research. 2001; 80:855-9.

[50] Soman S, Chacko A S, Prasad V S. Semi-interpenetrating network composites of poly(lactic acid) with cis-9-octadecenylamine modified cellulose-nanofibers from *Areca catechu* husk. Composites Science and Technology. 2017; 141:65-73.

[51] Venz S, Dickens B. NIR-spectroscopic investigation of water sorption characteristics of dental resins and composites. Journal of Biomedical Materials Research. 1991; 25:1231-48.

[52] Santerre J P, Shajii L, Tsang H. Biodegradation of commercial dental composites by cholesterol esterase. J Dent Res. 1999; 78:1459-68.

[53] Nishiyama N, Asakura T, Suzuki K, Komatsu K, Nemoto K. Bond strength of resin to acid-etched dentin studied by 13C NMR: Interaction between N-methacryloyl-w-amino acid primer and dentinal collagen. Journal of Dental Research. 2000; 79:806-11.

[54] Nishiyama N, Asakura T, Suzuki K, Sato T, Nemoto K. Adhesion mechanisms of resin to etched dentin primed with N-methacryloyl glycine studied by 13C-NMR. Journal of Biomedical Materials Research. 1998; 40:458-63.

[55] Halawa A H, Abd E I-Gilil S M, Bedair A H, Eliwa E M, Frese M, Sewald N, et al. Synthesis of diverse amide linked bis-indoles and indole derivatives bearing coumarin-based moiety: cytotoxicity and molecular docking investigations. Medicinal Chemistry Research. 2018; 27:796-806.

What is claimed:

1. A composition comprising:
   i) a polymerizable bifunctionalized methacrylate base monomer;
   ii) a polymerization initiator;
   iii) a polymerization inhibitor or a polymerization stabilizer; and
   iv) a methacrylamide compound of Formula (I):

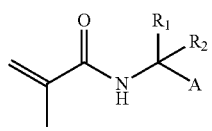
(I)

wherein:
A is selected from —$R_3$—OH; —$CO_2R_4$, and —$R_3$—$CO_2R_4$;
$R_1$ is selected from:
a) $C_1$-$C_6$ alkyl;
b) $C_3$-$C_6$ cycloalkyl;
c) —$CH_2$-$C_3$-$C_6$ cycloalkyl;
d) $C_3$-$C_6$ cycloalkenyl substituted by 0, 1, 2, 3, or 4 $C_1$-$C_4$ alkyl substituents;
e) —$CH_2$-$C_3$-$C_6$ cycloalkenyl substituted by 0, 1, 2, 3, or 4 $C_1$-$C_4$ alkyl substituents;
f) phenyl substituted by 0, 1, 2, 3, or 4 $C_1$-$C_4$ alkyl substituents; and
g) benzyl substituted by 0, 1, 2, 3, or 4 $C_1$-$C_4$ alkyl substituents;
$R_2$ is selected from H and $C_1$-$C_6$ alkyl; and
$R_3$ is selected from the group of:
a) $C_1$-$C_{16}$ linear or branched alkylene;
b) $C_2$-$C_{16}$ linear or branched alkenylene;

c)
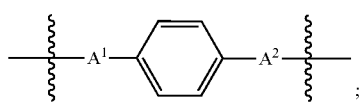
;

d)
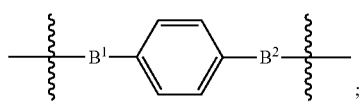
;

e)
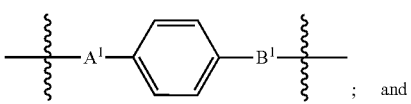
; and f)
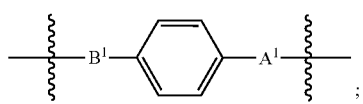
;

$A^1$ and $A^2$ in each instance is independently a $C_1$-$C_{12}$ alkylene chain optionally substituted by 1, 2, 3, or 4 $C_1$-$C_4$ alkyl substituents;
$B^1$ and $B^2$ in each instance is independently a $C_2$-$C_{12}$ alkenylene optionally substituted by 1, 2, 3, or 4 $C_1$-$C_4$ alkyl substituents;

each wavy line

represents a bond through which the indicated $A^1$ or $A^2$ alkylene chain or $B^1$ or $B^2$ alkenylene chain is attached;
with the proviso that the combined number of carbon atoms in the alkylene and/or alkenylene chains of the pairings $A^1$-$A^2$, $B^1$-$B^2$, $A^1$-$B^1$, and $B^1$-$A^1$ does not exceed 16;
$R_4$ is selected from the group of H, $C_1$-$C_6$ alkyl, $C_3$-$C_6$ cycloalkyl, $C_3$-$C_6$ cycloalkenyl, —$(CH_2)$q-cycloalkyl, —$(CH_2)$q-cycloalkenyl, phenyl, benzyl, and naphthyl; and
q is an integer selected from the group of 1, 2, 3, and 4.

2. The composition of claim 1, wherein $R_3$ is selected from the group of:
   a) $C_{10}$-$C_{16}$ linear or branched alkylene;
   b) $C_{10}$-$C_{16}$ linear or branched alkenylene;

c)
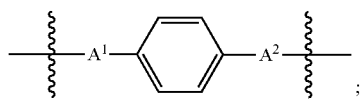
;

d)
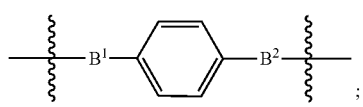
;

e)
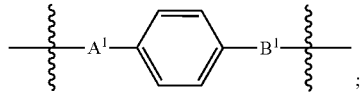
;

f)
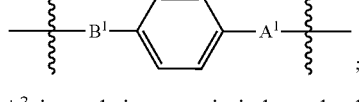
;

$A^1$ and $A^2$ in each instance is independently a $C_1$-$C_{12}$ alkylene chain optionally substituted by 1, 2, 3, or 4 $C_1$-$C_4$ alkyl substituents;
$B^1$ and $B^2$ in each instance is independently a $C_2$-$C_{12}$ alkenylene optionally substituted by 1, 2, 3, or 4 $C_1$-$C_4$ alkyl substituents;
with the proviso that the combined number of carbon atoms in the alkylene and/or alkenylene chains of the pairings $A^1$-$A^2$, $B^1$-$B^2$, $A^1$-$B^1$, and $B^1$-$A^1$ is an integer selected from the group of 10, 11, 12, 13, 14, 15, and 16.

3. The composition of claim 1, wherein the compound of Formula (I) is selected from the group of a compound of Formula (II), Formula (II), Formula (III), Formula (IV), Formula (V), Formula (VI), and Formula (VII), in each of which A is selected from the group of —$R_3$—OH; —$CO_2R_4$, and —$R_3$—$CO_2R_4$:

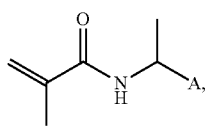
(II)

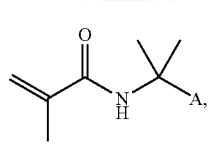
(III)

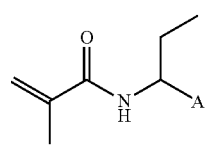
(IV)

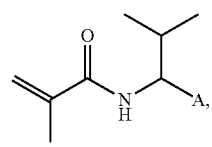
(V)

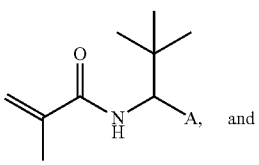
(VI), and

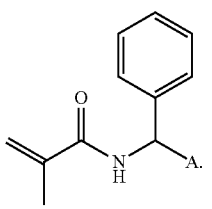
(VII)

4. The composition of claim 1, wherein A is selected from the group of —$R_3$—OH; —$CO_2R_4$, and —$R_3$—$CO_2R_4$;
$R_1$ is selected from the group of $C_1$-$C_6$ alkyl; phenyl substituted by 0, 1, 2, 3, or 4 $C_1$-$C_4$ alkyl substituents; and benzyl substituted by 0, 1, 2, 3, or 4 $C_1$-$C_4$ alkyl substituents;
$R_2$ is selected from the group of H and $CH_3$; and
$R_3$ is $C_1$-$C_{16}$ linear or branched alkylene or $C_2$-$C_{16}$ linear or branched alkenylene.

5. The composition of claim 1, wherein A is selected from the group of —$R_3$—OH; —$CO_2R_4$, and —$R_3$—$CO_2R_4$;
$R_1$ is $C_1$-$C_6$ alkyl;
$R_2$ is selected from the group of H and $CH_3$; and
$R_3$ is $C_1$-$C_{16}$ alkylene or $C_2$-$C_{16}$ linear or branched alkenylene.

6. The composition of claim 1, wherein A is selected from the group of —$R_3$—OH; —$CO_2R_4$, and —$R_3$—$CO_2R_4$;
$R_1$ is phenyl;
$R_2$ is H; and
$R_3$ is $C_1$-$C_{16}$ alkylene or $C_2$-$C_{16}$ linear or branched alkenylene.

7. The composition of claim 1, wherein A is —$R_3$—OH.

8. The composition of claim 1, wherein A is —$CO_2R_4$; $R_4$ is selected from the group of H, $C_1$-$C_6$ alkyl, $C_3$-$C_6$ cycloalkyl, $C_3$-$C_6$ cycloalkenyl, —$(CH_2)q$-cycloalkyl, —$(CH_2)q$-cycloalkenyl, phenyl, benzyl, and naphthyl; and q is an integer selected from the group of 1, 2, 3, and 4.

9. The composition of claim 1, wherein A is —$CO_2R_4$; $R_4$ is selected from the group of H and $C_1$-$C_6$ alkyl.

10. The composition of claim 1 wherein A is —$R_3$—$CO_2R_4$; $R_4$ is selected from the group of H, $C_1$-$C_6$ alkyl, $C_3$-$C_6$ cycloalkyl, $C_3$-$C_6$ cycloalkenyl, —$(CH_2)q$-cycloalkyl, —$(CH_2)q$-cycloalkenyl, phenyl, benzyl, and naphthyl; and q is an integer selected from the group of 1, 2, 3, and 4.

11. The composition of claim 1, wherein A is —$R_3$—$CO_2R_4$; $R_4$ is selected from the group of H and $C_1$-$C_6$ alkyl.

12. The composition of claim 1, wherein the methacrylate base monomer is selected from the group of:
(2-Hydroxyethyl methacrylate);
(2-Hydroxyethyl acrylate);
2-hydroxyethyl methacrylate phosphate;
2-methacryloyloxyethylphenyl hydrogen phosphate;
10-(phosphonooxy)decyl methacrylate;
4-((2-(methacryloyloxy)ethoxy)carbonyl)phthalic acid;
4-(2-methacryloyloxyethyl)trimellitic anhydride;
2-[10-[(2-methyl-1-oxo-2-propen-1-yl)oxy]decyl]-propanedioic acid;
N-(2-hydroxy-3-(methacryloyloxy)propyl)-N-(p-tolyl) glycine;
((propane-2,2-diylbis(4,1-phenylene))bis(oxy))bis(2-hydroxypropane-3,1-diyl) bis(2-methylacrylate);
7,7,9-trimethyl-4,13-dioxo-3,14-dioxa-5,12-diazahexadecane-1,16-diyl bis(2-methylacrylate); and
(ethane-1,2-diylbis(oxy))bis(ethane-2,1-diyl) bis(2-methylacrylate).

13. The composition of claim 1, wherein the polymerization initiator is one or more agents selected from the group consisting of 2,2-Dimethoxy-2-phenylacetophenone/diphenyliodonium hexafluorophosphate, camphorquinone/Ethyl-4-dimethylamino benzoate, camphorquinone/2-(dimethylamino)ethyl methacrylate, camphorquinone/1-Phenyl-1,2-propanedione, camphorquinone/2-(dimethylamino)ethyl methacrylate/diphenyliodonium hexafluorophosphate, camphorquinone/Ethyl-4-dimethylamino benzoate/diphenyliodonium hexafluorophosphate, Ethyl-4-dimethylamino benzoate, Bisacylphosphine oxide; 1-Phenyl-1,2-propanedione, naphthacene, 9-anthracene, diphenyliodonium hexafluorophosphate, and 2,2-Dimethoxy-2-phenylacetophenone.

14. The composition of claim 1, wherein the polymerization inhibitor or polymerization stabilizer is one or more agents selected from the group of 2,6-di(tert-butyl)-4-methylphenol; tertbutyl hydroquinone; 2,5-di-tert-butylhydroquinone; monomethyl ether hydroquinone; 3,5-di-tert-butyl-4-hydroxyanisole (2,6-di-tert-butyl-4-ethoxyphenol); 2,5-di-tert-butyl hydroquinone; 2-(2'-hydroxy-5'-methylphenyl)-2H-benzotriazole; 2-(2'-hydroxy-5'-t-octylphenyl)-2H-benzotriazole; 2-hydroxy4-methoxybenzophenone (UV-9); 2-(2'-hydroxy-4',6'-di-tertpentylphenyl)-2H-benzotriazole; 2-hydroxy-4-n-octoxybenzophenone; and 2-(2'-hydroxy-5'-methacryloxyethylphenyl)-2H-benzotriazole.

15. The composition of claim 1, further comprising a dental filler.

16. The composition of claim 1, further comprising an organic solvent acceptable for dental use.

17. The composition of claim 1, wherein $R_3$ is selected from the group of:
a) $C_1$-$C_{16}$ linear or branched alkylene;
b) $C_2$-$C_{16}$ linear or branched alkenylene;
c)
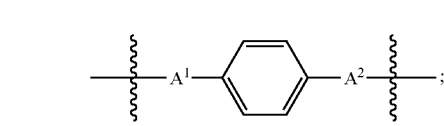
d)

-continued e) 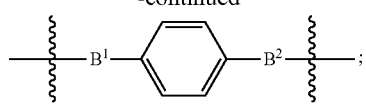

f) 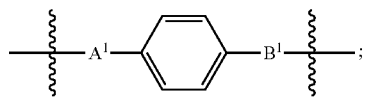

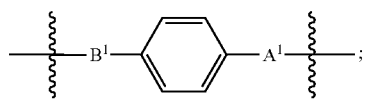

A¹ and A² in each instance is independently a $C_1$-$C_8$ alkylene chain optionally substituted by 1, 2, 3, or 4 $C_1$-$C_4$ alkyl substituents; and B¹ and B² in each instance is independently a $C_2$-$C_8$ alkenylene optionally substituted by 1, 2, 3, or 4 $C_1$-$C_4$ alkyl substituents;

with the proviso that the combined number of carbon atoms in the alkylene and/or alkenylene chains of the pairings A¹-A², B¹-B², A¹-B¹, and B¹-A¹ does not exceed 10.

18. The composition of claim 15, wherein the dental filler is one or more agents selected from the group of aluminum oxide, titanium dioxide, zinc oxide, zirconium oxide, calcium oxide, phosphorus oxides, barium glass, strontium glass, quartz, barium aluminum silicate glass, barium borosilicate, lithium aluminum silicate, strontium aluminum silicate glass, and silicon dioxide.

* * * * *